United States Patent
Aston et al.

(10) Patent No.: US 7,572,790 B2
(45) Date of Patent: Aug. 11, 2009

(54) BIPHENYL CARBOXYLIC AMIDE P38 KINASE INHIBITORS

(75) Inventors: Nicola Mary Aston, Stevenage (GB); Paul Bamborough, Stevenage (GB); Katherine Louise Jones, Stevenage (GB); Vipulkumar Kantibhai Patel, Stevenage (GB); Stephen Swanson, Stevenage (GB); Ann Louise Walker, Stevenage (GB)

(73) Assignee: SmithKline Beecham Corporation, Philadelphia, PA (US)

(*) Notice: Subject to any disclaimer, the term of this patent is extended or adjusted under 35 U.S.C. 154(b) by 323 days.

(21) Appl. No.: 10/551,502

(22) PCT Filed: Apr. 7, 2004

(86) PCT No.: PCT/EP2004/003774

§ 371 (c)(1),
(2), (4) Date: Jun. 28, 2006

(87) PCT Pub. No.: WO2004/089874

PCT Pub. Date: Oct. 21, 2004

(65) Prior Publication Data

US 2007/0129354 A1    Jun. 7, 2007

(30) Foreign Application Priority Data

Apr. 9, 2003  (GB)  ................ 0308186.6

(51) Int. Cl.
- A61K 31/54 (2006.01)
- A61K 31/5377 (2006.01)
- A61K 31/495 (2006.01)
- A61K 31/445 (2006.01)
- A61K 31/426 (2006.01)
- A61K 31/421 (2006.01)
- A61K 31/4164 (2006.01)
- A61K 31/40 (2006.01)
- A61K 31/165 (2006.01)

(52) U.S. Cl. ............ 514/227.5; 514/237.8; 514/252.12; 514/317; 514/365; 514/374; 514/396; 514/408; 514/602; 514/616; 544/59; 544/162; 544/399; 546/229; 548/577; 564/86; 564/152

(58) Field of Classification Search .............. 514/227.5, 514/237.8, 252.12, 317, 365, 374, 396, 408, 514/602, 616; 544/59, 162, 399; 546/229; 548/577; 564/86, 152

See application file for complete search history.

(56) References Cited

U.S. PATENT DOCUMENTS

| | | | |
|---|---|---|---|
| 4,200,750 A | 4/1980 | Warner et al. |
| 5,236,934 A | 8/1993 | VanAtten |
| 5,246,943 A | 9/1993 | Blankley et al. |
| 5,521,213 A | 5/1996 | Prasit et al. |
| 5,534,518 A | 7/1996 | Henrie et al. |
| 5,658,903 A | 8/1997 | Adams et al. |
| 5,858,995 A | 1/1999 | Kawai et al. |
| 5,932,576 A | 8/1999 | Anantanarayan et al. |
| 5,945,418 A | 8/1999 | Bemis et al. |
| 5,977,103 A | 11/1999 | Adams et al. |
| 6,087,496 A | 7/2000 | Anantanarayan et al. |
| 6,130,235 A | 10/2000 | Mavunkel et al. |
| 6,147,080 A | 11/2000 | Bemis et al. |
| 6,174,887 B1 | 1/2001 | Haruta et al. |
| 6,251,914 B1 | 6/2001 | Adams et al. |
| 6,277,989 B1 | 8/2001 | Chakravarty et al. |
| 6,436,925 B1 | 8/2002 | Lubisch et al. |
| 6,451,794 B1 | 9/2002 | Beswick et al. |
| 6,498,166 B1 | 12/2002 | Campbell et al. |
| 6,509,361 B1 | 1/2003 | Weier et al. |
| 6,509,363 B2 | 1/2003 | Salituro et al. |
| 6,579,872 B1 | 6/2003 | Brown et al. |
| 6,638,980 B1 | 10/2003 | Su et al. |

(Continued)

FOREIGN PATENT DOCUMENTS

EP    0 533 266    9/1992

(Continued)

OTHER PUBLICATIONS

Salituro et al. "Inhibitors of p38 MAP Kinase: Therapeutic Intervention in Cytokine-Mediated Diseases" Current Medicinal Chemistry, 1999, vol. 6, pp. 807-823.*

(Continued)

*Primary Examiner*—Rei-Tsang Shiao
*Assistant Examiner*—Joseph R Kosack
(74) *Attorney, Agent, or Firm*—Dara L. Dinner; Charles M. Kinzig

(57) ABSTRACT

Compound of formula (I):

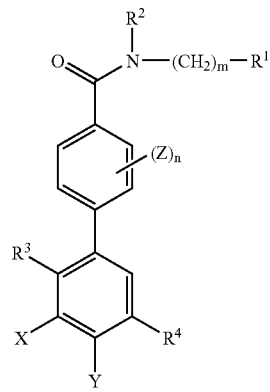

or pharmaceutically acceptable derivatives thereof, and their use as pharmaceuticals, particularly as p38 kinase inhibitors.

15 Claims, No Drawings

U.S. PATENT DOCUMENTS

| | | | |
|---|---|---|---|
| 6,696,464 | B2 | 2/2004 | McClure et al. |
| 6,774,127 | B2 | 8/2004 | Adams et al. |
| 6,821,965 | B1 | 11/2004 | Brown et al. |
| 6,855,719 | B1 | 2/2005 | Thomas et al. |
| 7,056,942 | B2 * | 6/2006 | Hildesheim et al. ......... 514/411 |
| 2001/0011135 | A1 | 8/2001 | Reidl et al. |
| 2004/0038858 | A1 | 2/2004 | Dorsch et al. |
| 2004/0176446 | A1 | 9/2004 | Alonso-Alija et al. |
| 2004/0242868 | A1 | 12/2004 | Angell et al. |
| 2004/0249161 | A1 | 12/2004 | Angell et al. |
| 2004/0266839 | A1 | 12/2004 | Angell et al. |
| 2004/0267012 | A1 | 12/2004 | Angell et al. |
| 2005/0020540 | A1 | 1/2005 | Angell et al. |
| 2005/0020590 | A1 | 1/2005 | Lang et al. |
| 2005/0038014 | A1 | 2/2005 | Angell et al. |
| 2005/0065195 | A1 | 3/2005 | Angell et al. |
| 2005/0090491 | A1 | 4/2005 | Angell et al. |

FOREIGN PATENT DOCUMENTS

| | | |
|---|---|---|
| EP | 0 533 268 | 9/1992 |
| EP | 0 346 841 | 6/2003 |
| EP | 0 430 033 | 4/2004 |
| GB | 2 276 161 | 3/1993 |
| GB | 2 276 162 | 3/1993 |
| GB | 2 273 930 | 12/1993 |
| GB | 2 295 387 | 5/1996 |
| WO | WO 94/15920 | 7/1994 |
| WO | WO 95/06636 | 3/1995 |
| WO | WO 95/06644 | 3/1995 |
| WO | WO 95/11243 | 4/1995 |
| WO | WO 95/15954 | 6/1995 |
| WO | WO 95/17401 | 6/1995 |
| WO | WO 95/29907 | 11/1995 |
| WO | WO 95/30675 | 11/1995 |
| WO | WO 96/31508 | 10/1996 |
| WO | WO 96/31509 | 10/1996 |
| WO | WO 97/03034 | 1/1997 |
| WO | WO 99/32463 | 7/1999 |
| WO | WO 00/12074 | 3/2000 |
| WO | WO 00/12497 | 3/2000 |
| WO | WO 00/26216 | 5/2000 |
| WO | WO 00/56738 | 9/2000 |
| WO | WO 00/71493 | 11/2000 |
| WO | WO 00/71509 | 11/2000 |
| WO | WO 00/71510 | 11/2000 |
| WO | WO 00/71511 | 11/2000 |
| WO | WO 01/27089 | 4/2001 |
| WO | WO 01/34605 | 5/2001 |
| WO | WO 01/70695 | 9/2001 |
| WO | WO 01/87875 | 11/2001 |
| WO | WO 02/09648 A2 * | 2/2002 |
| WO | WO 02/40486 | 5/2002 |
| WO | WO 03/032970 | 4/2003 |
| WO | WO 03/068747 | 8/2003 |
| WO | WO 03/093248 | 11/2003 |
| WO | WO 2004/010995 | 2/2004 |
| WO | WO 2004/089875 | 10/2004 |
| WO | WO 2004/089876 | 10/2004 |
| WO | WO 2005/014550 | 2/2005 |
| WO | WO 2005/061465 | 7/2005 |

OTHER PUBLICATIONS

Boehm et al., *Expert Opinion of Therapeutic Patents*, vol. 10 (1) pp. 25-37 (2000).

Boehm, et al, *Journal of Medicinal Chemistry*, vol. 39(20) pp. 3929-3937 (1996).

Ceccarelli et al., *European Journal of Medicinal Chemistry*, vol. 33 (12) pp. 943-955 (1998).

Gabriele et al., *European Journal of Organic Chemistry*, vol. 2001 (24) pp. 4607-4613 (2001).

Han et al., *Biohemica et Biophysica Acta—Molecular Cell Research*, vol. 1265 (2-3) pp. 224-227 (1995.

Hanson, *Expert Opinion on Therapeutic Patents*, vol. 7(7) pp. 729-733 (1997).

Henry et al., *Drugs of the Future*, vol. 24 (12) pp. 1345-1354 (1999).

Jiang et al, *Journal of Biological Chemistry*, vol. 271 (30) pp. 17920-17926 (1996).

Li et al., *Biochemical and Biophysical Research Communications*, vol. 228 (2) pp. 334-340 (1996).

Liebeskind et al., *Organic Letters*, vol. 4 (6) pp. 979-981 (2002).

Moreland et al., *Annals of Internal Medicine*, vol. 130 (6) pp. 478-486 (1999).

Murali Dhar et al., *Bioorganic and Medicinal Chemistry Letters*, vol. 12 (21) pp. 3125-3128 (2002).

Rankin et al., *British Journal of Rheumatology*, vol. 34 pp. 334-342 (1995).

Salituro et al., *Current Medicinal Chemistry*, vol. 6 pp. 807-823 (1999).

Wang et al., *Journal of Biological Chemistry*, vol. 272 (38) pp. 23668-23674 (1997).

* cited by examiner

BIPHENYL CARBOXYLIC AMIDE P38 KINASE INHIBITORS

This application claims the benefit of §371 application of PCT/EP2004/003774, filed 7 Apr. 2004.

This invention relates to novel compounds and their use as pharmaceuticals, particularly as p38 kinase inhibitors, for the treatment of certain diseases and conditions.

We have now found a group of novel compounds that are inhibitors of p38 kinase.

According to the invention there is provided a compound of formula (I):

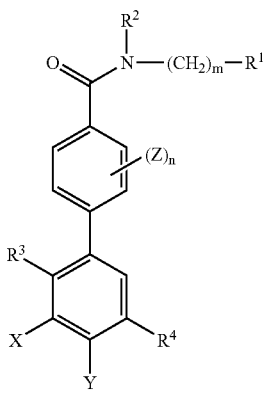

wherein $R^1$ is selected from hydrogen, $C_{1-6}$alkyl optionally substituted by up to three groups independently selected from $C_{1-6}$alkoxy, halogen and hydroxy, $C_{2-6}$alkenyl, $C_{3-7}$cycloalkyl optionally substituted by one or more $C_{1-6}$alkyl groups, phenyl optionally substituted by up to three groups independently selected from $R^5$ and $R^6$, and heteroaryl optionally substituted by up to three groups independently selected from $R^5$ and $R^6$, $R^2$ is selected from hydrogen, $C_{1-6}$alkyl and —$(CH_2)_p$—$C_{3-7}$cycloalkyl optionally substituted by one or more $C_{1-6}$alkyl groups, or $(CH_2)_m R^1$ and $R^2$, together with the nitrogen atom to which they are bound, form a four- to six-membered heterocyclic ring optionally substituted by up to three $C_{1-6}$alkyl groups;

$R^3$ is chloro or methyl;

$R^4$ is the group —NH—CO—$R^7$ or —CO—NH—$(CH_2)_p$—$R^8$;

$R^5$ is selected from $C_{1-6}$alkyl, $C_{1-6}$alkoxy, —$(CH_2)_p$—$C_{3-7}$cycloalkyl optionally substituted by one or more $C_{1-6}$alkyl groups, —$CONR^9R^{10}$, —$NHCOR^{10}$, —$SO_2NHR^9$, —$(CH_2)_q NHSO_2R^{10}$, halogen, CN, OH, —$(CH_2)_q NR^{11}R^{12}$, and trifluoromethyl;

$R^6$ is selected from $C_{1-6}$alkyl, $C_{1-6}$alkoxy, halogen, trifluoromethyl and —$(CH_2)_q NR^{11}R^{12}$;

$R^7$ is selected from hydrogen, $C_{1-6}$alkyl, —$(CH_2)_p$—$C_{3-7}$cycloalkyl optionally substituted by one or more $C_{1-6}$alkyl groups, trifluoromethyl, —$(CH_2)_r$heteroaryl optionally substituted by $R^{13}$ and/or $R^{14}$, and —$(CH_2)_r$phenyl optionally substituted by $R^{13}$ and/or $R^{14}$;

$R^8$ is selected from hydrogen, $C_{1-6}$alkyl, $C_{3-7}$cycloalkyl optionally substituted by one or more $C_{1-6}$alkyl groups, $CONHR^9$, phenyl optionally substituted by $R^{13}$ and/or $R^{14}$, and heteroaryl optionally substituted by $R^{13}$ and/or $R^{14}$;

$R^9$ and $R^{10}$ are each independently selected from hydrogen and $C_{1-6}$alkyl, or $R^9$ and $R^{10}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two $C_{1-6}$alkyl groups;

$R^{11}$ is selected from hydrogen, $C_{1-6}$alkyl and —$(CH_2)_p$—$C_{3-7}$cycloalkyl optionally substituted by one or more $C_{1-6}$alkyl groups, $R^{12}$ is selected from hydrogen and $C_{1-6}$alkyl, or $R^{11}$ and $R^{12}$, together with the nitrogen atom to which they are bound, form a five or six-membered heterocyclic ring optionally containing one additional heteroatom selected from oxygen, sulfur and N—$R^{15}$;

$R^{13}$ is selected from $C_{1-6}$alkyl, $C_{1-6}$alkoxy, —$(CH_2)_p$—$C_{3-7}$cycloalkyl optionally substituted by one or more $C_{1-6}$alkyl groups, —$CONR^9R^{10}$, —$NHCOR^{10}$, halogen, CN, —$(CH_2)_q NR^{11}R^{12}$, trifluoromethyl, phenyl optionally substituted by one or more $R^{14}$ groups and heteroaryl optionally substituted by one or more $R^{14}$ groups;

$R^{14}$ is selected from $C_{1-6}$alkyl, $C_{1-6}$alkoxy, halogen, trifluoromethyl and —$NR^{11}R^{12}$;

$R^{15}$ is selected from hydrogen and methyl;

X and Y are each independently selected from hydrogen, methyl and halogen;

Z is selected from —$(CH_2)_s OR^{16}$, —$(CH_2)_s NR^{16}R^{17}$, —$(CH_2)_s CH_2 CH_2 R^{16}$, —$(CH_2)_s COOR^{16}$, —$(CH_2)_s CONR^{16}R^{17}$, —$(CH_2)_s NHCOR^{16}$, —$(CH_2)_s NHCONR^{16}R^{17}$, —$(CH_2)_s SO_2 R^{16}$, —$(CH_2)_s SO_2 NR^{16}R^{17}$ and —$(CH_2)_s NHSO_2 R^{16}$;

$R^{16}$ is selected from hydrogen, $C_{1-6}$alkyl optionally substituted by up to two hydroxy groups, —$(CH_2)_t OR^{18}$, —$(CH_2)_t NR^{18}R^{19}$, —$(CH_2)_t NHSO_2 R^{18}$, —$(CH_2)_t CONR^{18}R^{19}$, —$(CH_2)_t COOR^{18}$, —$(CH_2)_t$heteroaryl optionally substituted by up to two groups independently selected from halogen, $C_{1-6}$alkyl and oxo, and —$(CH_2)_t$phenyl optionally substituted by up to two groups independently selected from halogen, $C_{1-6}$alkyl and $C_{1-6}$alkoxy, $R^{17}$ is selected from hydrogen and $C_{1-6}$alkyl, or $R^{16}$ and $R^{17}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two groups independently selected from oxo, halogen and $C_{1-6}$alkyl;

$R^{18}$ and $R^{19}$ are each independently selected from hydrogen and $C_{1-6}$alkyl optionally substitued by up to two hydroxy groups, or $R^{18}$ and $R^{19}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two groups independently selected from oxo, halogen and $C_{1-6}$alkyl;

m is selected from 0, 1, 2, 3 and 4, wherein each carbon atom of the resulting carbon chain may be optionally substituted with up to two groups independently selected from $C_{1-6}$alkyl and halogen;

n is 1;

p is selected from 0, 1 and 2;

q is selected from 0, 1, 2 and 3;

r is selected from 0 and 1;

s is selected from 0, 1, 2, 3 and 4; and t is selected from 1, 2, 3 and 4;

or a pharmaceutically acceptable derivative thereof.

According to a further embodiment of the invention there is provided a compound of formula (IA):

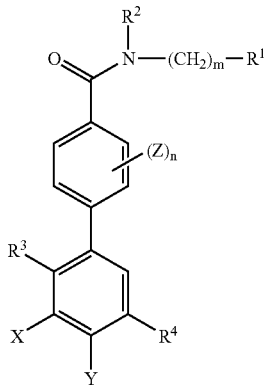

(IA)

wherein $R^1$ is selected from hydrogen, $C_{1-6}$alkyl optionally substituted by up to three groups independently selected from $C_{1-6}$alkoxy, halogen and hydroxy, $C_{2-6}$alkenyl, $C_{3-7}$cycloalkyl optionally substituted by one or more $C_{1-6}$alkyl groups, phenyl optionally substituted by up to three groups independently selected from $R^5$ and $R^6$, and heteroaryl optionally substituted by up to three groups independently selected from $R^5$ and $R^6$, $R^2$ is selected from hydrogen, $C_{1-6}$alkyl and —$(CH_2)_p$—$C_{3-7}$cycloalkyl optionally substituted by one or more $C_{1-6}$alkyl groups, or $(CH_2)_m R^1$ and $R^2$, together with the nitrogen atom to which they are bound, form a four- to six-membered heterocyclic ring optionally substituted by up to three $C_{1-6}$alkyl groups;

$R^3$ is chloro or methyl;

$R^4$ is the group —NH—CO—$R^7$ or —CO—NH—$(CH_2)_p$—$R^8$;

$R^5$ is selected from $C_{1-6}$alkyl, $C_{1-6}$alkoxy, —$(CH_2)_p$—$C_{3-7}$cycloalkyl optionally substituted by one or more $C_{1-6}$alkyl groups, —$CONR^9R^{10}$, —$NHCOR^{10}$, —$SO_2NHR^9$, —$(CH_2)_q NHSO_2R^{10}$, halogen, CN, OH, —$(CH_2)_q NR^{11}R^{12}$, and trifluoromethyl;

$R^6$ is selected from $C_{1-6}$alkyl, $C_{1-6}$alkoxy, halogen, trifluoromethyl and —$(CH_2)_q NR^{11}R^{12}$;

$R^7$ is selected from hydrogen, $C_{1-6}$alkyl, —$(CH_2)_p$—$C_{3-7}$cycloalkyl optionally substituted by one or more $C_{1-6}$alkyl groups; trifluoromethyl, —$(CH_2)_r$heteroaryl optionally substituted by $R^{13}$ and/or $R^{14}$, and —$(CH_2)_r$phenyl optionally substituted by $R^{13}$ and/or $R^{14}$;

$R^8$ is selected from hydrogen, $C_{1-6}$alkyl, $C_{3-7}$cycloalkyl optionally substituted by one or more $C_{1-6}$alkyl groups, $CONHR^9$, phenyl optionally substituted by $R^{13}$ and/or $R^{14}$, and heteroaryl optionally substituted by $R^{13}$ and/or $R^{14}$;

$R^9$ and $R^{10}$ are each independently selected from hydrogen and $C_{1-6}$alkyl, or $R^9$ and $R^{10}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two $C_{1-6}$alkyl groups;

$R^{11}$ is selected from hydrogen, $C_{1-6}$alkyl and —$(CH_2)_p$—$C_{3-7}$cycloalkyl optionally substituted by one or more $C_{1-6}$alkyl groups, $R^{12}$ is selected from hydrogen and $C_{1-6}$alkyl, or $R^{11}$ and $R^{12}$, together with the nitrogen atom to which they are bound, form a five or six-membered heterocyclic ring optionally containing one additional heteroatom selected from oxygen, sulfur and N—$R^{15}$;

$R^{13}$ is selected from $C_{1-6}$alkyl, $C_{1-6}$alkoxy, —$(CH_2)_p$—$C_{3-7}$cycloalkyl optionally substituted by one or more $C_{1-6}$alkyl groups, —$CONR^9R^{10}$, —$NHCOR^{10}$, halogen, CN, —$(CH_2)_q NR^{11}R^{12}$, trifluoromethyl, phenyl optionally substituted by one or more $R^{14}$ groups and heteroaryl optionally substituted by one or more $R^{14}$ groups;

$R^{14}$ is selected from $C_{1-6}$alkyl, $C_{1-6}$alkoxy, halogen, trifluoromethyl and —$NR^{11}R^{12}$;

$R^{15}$ is selected from hydrogen and methyl;

X and Y are each independently selected from hydrogen, methyl and halogen;

Z is selected from —$(CH_2)_s OR^{16}$, —$(CH_2)_s NR^{16}R^{17}$, —$(CH_2)_s CH_2 CH_2 R^{16}$, —$(CH_2)_s COOR^{16}$, —$(CH_2)_s CONR^{16}R^{17}$, —$(CH_2)_s NHCOR^{16}$, —$(CH_2)_s NHCONR^{16}R^{17}$, —$(CH_2)_s SO_2R^{16}$, —$(CH_2)_s SO_2NR^{16}R^{17}$ and —$(CH_2)_s NHSO_2R^{16}$;

$R^{16}$ Is selected from hydrogen, $C_{1-6}$alkyl, —$(CH_2)_t OR^{18}$, —$(CH_2)_t NR^{18}R^{19}$, —$(CH_2)_t COOR^{18}$, —$(CH_2)_t$heteroaryl optionally substituted by up to two groups independently selected from halogen and $C_{1-6}$alkyl, and —$(CH_2)_t$phenyl optionally substituted by up to two groups independently selected from halogen, $C_{1-6}$alkyl and $C_{1-6}$alkoxy, $R^{17}$ is selected from hydrogen and $C_{1-6}$alkyl, or $R^{16}$ and $R^{17}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two groups independently selected from oxo, halogen and $C_{1-6}$alkyl;

$R^{18}$ and $R^{19}$ are each independently selected from hydrogen and $C_{1-6}$alkyl, or $R^{18}$ and $R^{19}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two groups independently selected from oxo, halogen and $C_{1-6}$alkyl;

m is selected from 0, 1, 2, 3 and 4, wherein each carbon atom of the resulting carbon chain may be optionally substituted with up to two groups Independently selected from $C_{1-6}$alkyl and halogen;

n is 1;

p is selected from 0, 1 and 2;

q is selected from 0, 1, 2 and 3;

r is selected from 0 and 1;

s Is selected from 0, 1, 2, 3 and 4; and t is selected from 2, 3 and 4;

or a pharmaceutically acceptable derivative thereof.

In one embodiment, the compound of formula (I) is a compound of formula (IB)

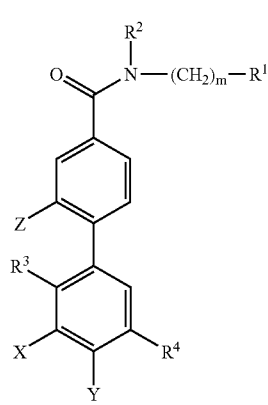

(IB)

in which $R^1$, $R^2$, $R^3$, $R^4$, X, Y, Z and m are as hereinbefore defined.

In a preferred embodiment, the molecular weight of a compound of formula (I) does not exceed 1000, more preferably 800, even more preferably 600.

In one embodiment, $R^1$ is selected from $C_{1-4}$alkyl, $C_{2-6}$alkenyl, $C_{3-7}$cycloalkyl, phenyl optionally substituted by up to three groups selected from $R^5$ and $R^6$, and heteroaryl optionally substituted by up to three groups selected from $R^5$ and $R^6$. In another embodiment, $R^1$ is selected from $C_{1-4}$alkyl, $C_{3-7}$cycloalkyl and phenyl optionally substituted by up to three groups selected from $R^5$ and $R^6$. A representative example of $R^1$ is $C_{3-6}$cycloalkyl, in particular cyclopropyl. Further representative examples of $R^1$ include $C_{1-4}$alkyl, in particular 2-methylpropyl, 1,2-dimethylpropyl, 2,2-dimethylpropyl and 1,2,2-trimethylpropyl, and phenyl optionally substituted by up to three groups, preferably one group, selected from $R^5$ and $R^6$.

In one embodiment, $R^2$ is selected from hydrogen, $C_{1-4}$alkyl and —$CH_2$—$C_{3-6}$cycloalkyl. A representative example of $R^2$ is hydrogen.

A representative example of $R^3$ is methyl.

A representative example of $R^4$ is —CO—NH—$(CH_2)_p$—$R^8$.

In one embodiment, $R^5$ is selected from $C_{1-4}$alkyl, $C_{1-4}$alkoxy, —$(CH_2)_q$NHSO$_2$R$^{10}$, halogen, —$(CH_2)_q$NR$^{11}$R$^{12}$ and trifluoromethyl. Representative examples of $R^5$ include $C_{1-4}$alkyl, in particular methyl, and $C_{1-4}$alkoxy, in particular methoxy.

In one embodiment, $R^6$ is selected from $C_{1-4}$alkyl, $C_{1-4}$alkoxy, halogen and trifluoromethyl. Representative examples of $R^6$ include $C_{1-4}$alkyl, in particular methyl, and $C_{1-4}$alkoxy, in particular methoxy.

In one embodiment, $R^7$ is selected from $C_{1-4}$alkyl, —$(CH_2)_p$—$C_{3-7}$cycloalkyl, trifluoromethyl, —$(CH_2)_r$heteroaryl optionally substituted by $R^{13}$ and/or $R^{14}$, and —$(CH_2)_r$phenyl optionally substituted by $R^{13}$ and/or $R^{14}$.

In one embodiment, $R^8$ is selected from hydrogen, $C_{3-7}$cycloalkyl optionally substituted by one or more $C_{1-6}$alkyl groups, CONHR$^9$, phenyl optionally substituted by $R^{13}$ and/or $R^{14}$, and heteroaryl optionally substituted by $R^{13}$ and/or $R^{14}$. In another embodiment, $R^8$ is selected from $C_{3-7}$cycloalkyl, CONHR$^9$, phenyl optionally substituted by $R^{13}$ and/or $R^{14}$ and heteroaryl optionally substituted by $R^{13}$ and/or $R^{14}$. A representative example of $R^8$ is $C_{3-6}$cycloalkyl, in particular cyclopropyl.

In one embodiment, $R^9$ and $R^{10}$ are each independently selected from hydrogen and $C_{1-4}$alkyl.

In one embodiment, $R^{11}$ and $R^{12}$, together with the nitrogen atom to which they are bound, form a five or six-membered heterocyclic ring optionally further containing one additional heteroatom N—$R^{15}$.

In one embodiment, $R^{13}$ is selected from $C_{1-4}$alkyl, $C_{1-4}$alkoxy, halogen, —$(CH_2)_q$NR$^{11}$R$^{12}$, phenyl optionally substituted by one or more $R^{14}$ groups, and heteroaryl optionally substituted by one or more $R^{14}$ groups.

In one embodiment, $R^{14}$ is selected from from $C_{1-4}$alkyl, $C_{1-4}$alkoxy and —NR$^{11}$R$^{12}$.

In one embodiment, $R^{15}$ is methyl.

In one embodiment, X and Y are each independently selected from hydrogen, chlorine and fluorine. A representative example of X is fluorine. A further representative example of X is hydrogen. A representative example of Y is hydrogen.

In one embodiment Z is selected from —$(CH_2)_s$OR$^{16}$, —$(CH_2)_s$NR$^{16}$R$^{17}$, —$(CH_2)_s$NHCOR$^{16}$, —$(CH_2)_s$NHCONR$^{16}$R$^{17}$ and —$(CH_2)_s$NHSO$_2$R$^{16}$. A representative example of Z is —$(CH_2)_s$OR$^{16}$. Further representative examples of Z are —$(CH_2)_s$NR$^{16}$R$^{17}$, —$(CH_2)_s$NHCOR$^{16}$, —$(CH_2)_s$NHCONR$^{16}$R$^{17}$ and —$(CH_2)_s$NHSO$_2$R$^{16}$.

In one embodiment, $R^{16}$ is selected from hydrogen, $C_{1-6}$alkyl, —$(CH_2)_t$OR$^{18}$, —$(CH_2)_t$NR$^{18}$R$^{19}$, —$(CH_2)_t$COOR$^{18}$, —$(CH_2)_t$heteroaryl optionally substituted by up to two groups independently selected from halogen and $C_{1-6}$alkyl, and —$(CH_2)_t$phenyl optionally substituted by up to two groups independently selected from halogen, $C_{1-6}$alkyl and $C_{1-6}$alkoxy. In another embodiment, $R^{16}$ is selected from hydrogen, $C_{1-6}$alkyl optionally substituted by up to two hydroxy groups, —$(CH_2)_t$OR$^{18}$, —$(CH_2)_t$NR$^{18}$R$^{19}$, —$(CH_2)_t$NHSO$_2$R$^{18}$, —$(CH_2)_t$CONR$^{18}$R$^{19}$, —$(CH_2)_t$COOR$^{18}$, and —$(CH_2)_t$heteroaryl optionally substituted by up to two groups independently selected from halogen, $C_{1-6}$alkyl and oxo. A representative example of $R^{16}$ is —$(CH_2)_t$NR$^{18}$R$^{19}$. Further representative examples of $R^{16}$ include hydrogen; $C_{1-6}$alkyl optionally substituted by up to two hydroxy groups, in particular methyl, ethyl, n-propyl, 2,3-dihydroxypropyl, 4-hydroxybutyl and 2,2-dimethylpropyl; —$(CH_2)_t$OR$^{18}$; —$(CH_2)_t$NR$^{18}$R$^{19}$; —$(CH_2)_t$NHSO$_2$R$^{18}$; —$(CH_2)_t$CONR$^{18}$R$^{19}$; —$(CH_2)_t$COOR$^{18}$; and —$(CH_2)_t$heteroaryl optionally substituted by up to two groups independently selected from halogen, $C_{1-6}$alkyl and oxo, in particular wherein the heteroaryl is a 5-membered ring containing up to three heteroatoms selected from oxygen, nitrogen and sulfur such as an oxadiazole.

In one embodiment, $R^{17}$ is selected from hydrogen and $C_{1-4}$alkyl. A representative example of $R^{17}$ is hydrogen.

In one embodiment, $R^{18}$ and $R^{19}$ are each independently selected from hydrogen and $C_{1-4}$alkyl. In another embodiment, $R^{18}$ and $R^{19}$ are each independently selected from hydrogen, methyl, ethyl, 2-hydroxyethyl and isopropyl. A representative example of $R^{18}$ and $R^{19}$ is methyl. Further representative examples of $R^{18}$ and $R^{19}$ include hydrogen, ethyl, 2-hydroxyethyl and isopropyl.

In a further embodiment, $R^{18}$ and $R^{19}$, together with the nitrogen atom to which they are bound, form a five- to six-membered heterocyclic ring optionally containing oxygen, for example pyrrolidinyl or morpholinyl.

In one embodiment, m is selected from 0, 1 and 2. In another embodiment, m is selected from 0 and 1. A representative example of m is 1. A further representative example of m is 0.

In one embodiment, p is selected from 0 and 1. A representative example of p is 0.

In one embodiment, q is selected from 0 and 1.

In one embodiment, r is 0.

In one embodiment, s is selected from 0 and 1. A representative example of s is 0. A further representative example of s is 1.

In one embodiment t is selected from 2, 3 and 4. In another embodiment, t is selected from 2 and 3. A representative example of t is 2. Further representative examples of t include 1, 3 and 4.

It is to be understood that the present invention covers all combinations of particular and preferred groups described hereinabove. It is also to be understood that the present invention encompasses compounds of formula (I) in which a particular group or parameter, for example $R^5$, $R^6$, $R^9$, $R^{10}$, $R^{11}$, $R^{12}$, $R^{15}$, p or q may occur more than once. In such compounds it will be appreciated that each group or parameter is independently selected from the values listed.

Particular compounds according to the invention include those mentioned in the examples and their pharmaceutically derivatives.

Specific examples which may be mentioned include:

$N^3$-cyclopropyl-5-fluoro-2'-hydroxy-6-methyl-$N^{4'}$-[(4-methylphenyl)methyl]-3,4'-biphenyldicarboxamide;

$N^3$-cyclopropyl-$N^{4'}$-(2,2-dimethylpropyl)-5-fluoro-6-methyl -2'-{[(methyloxy)methyl]oxy}-3,4'-biphenyldicarboxamide;

$N^3$-cyclopropyl-5-fluoro-6-methyl-2'-{[(methyloxy)methyl]oxy}-$N^{4'}$-(2-methylpropyl)-3,4'-biphenyldicarboxamide;

$N^3$-cyclopropyl-$N^{4'}$-(cyclopropylmethyl)-5-fluoro-6-methyl-2'-{[(methyloxy)methyl]oxy}-3,4'-biphenyldicarboxamide;

$N^3$-cyclopropyl-5-fluoro-6-methyl-2'-{[(methyloxy)methyl]oxy}-$N^{4'}$-{[4-(methyloxy)phenyl]methyl}-3,4'-biphenylidicarboxamide;

$N^3$-cyclopropyl-5-fluoro-6-methyl-2'-{[(methyloxy)methyl]oxy}-$N^{4'}$-[(1R)-1,2,2-trimethylpropyl]-3,4'-biphenyldicarboxamide;

$N^3$-cyclopropyl-$N^{4'}$-[(1R)-1,2-dimethylpropyl]-5-fluoro-6-methyl-2'-{[(methyloxy)methyl]oxy}-3,4'-biphenyldicarboxamide;

$N^3$-cyclopropyl-$N^{4'}$-(2,2-dimethylpropyl)-5-fluoro-2'-hydroxy-6-methyl-3,4'-biphenylidicarboxamide;

$N^3$-cyclopropyl-5-fluoro-2'-hydroxy-6-methyl-$N^{4'}$-(2-methylpropyl)-3,4'-biphenyldicarboxamide;

$N^3$-cyclopropyl-$N^{4'}$-(cyclopropylmethyl)-5-fluoro-2'-hydroxy-6-methyl-3,4'-biphenyldicarboxamide;

$N^3$-cyclopropyl-5-fluoro-2'-hydroxy-6-methyl-$N^{4'}$-{[4-(methyloxy)phenyl]methyl}-3,4'-biphenylidicarboxamide;

$N^3$-cyclopropyl-5-fluoro-2'-hydroxy-6-methyl-$N^{4'}$-[(1R)-1,2,2-trimethylpropyl]-3,4'-biphenyldicarboxamide;

$N^3$-cyclopropyl-$N^{4'}$-[(1R)-1,2-dimethylpropyl]-5-fluoro-2'-hydroxy-6-methyl-3,4'-biphenyldicarboxamide;

$N^3$-cyclopropyl-$N^{4'}$-(2,2-dimethylpropyl)-5-fluoro-6-methyl-2'-(methyloxy)-3,4'-biphenylidicarboxamide;

$N^3$-cyclopropyl-5-fluoro-6-methyl-2'-(methyloxy)-$N^{4'}$-(2-methylpropyl)-3,4'-biphenylidicarboxamide;

$N^3$-cyclopropyl-$N^{4'}$-(cyclopropylmethyl)-5-fluoro-6-methyl-2'-(methyloxy)3,4'-biphenylidicarboxamide;

$N^3$-cyclopropyl-5-fluoro-6-methyl-2'-(methyloxy)-$N^{4'}$-{[4-(methyloxy)phenyl]methyl}-3,4'-biphenylidicarboxamide;

$N^3$-cyclopropyl-5-fluoro-6-methyl-2'-(methyloxy)-$N^{4'}$-[(1R)-1,2,2-trimethylpropyl]-3,4'-biphenyldicarboxamide;

$N^3$-cyclopropyl-$N^{4'}$-[(1R)-1,2-dimethylpropyl]-5-fluoro6-methyl-2'-(methyloxy)-3,4'-biphenylidicarboxamide;

$N^3$-cyclopropyl-$N_4$'-(2,2-dimethylpropyl)-5-fluoro-6-methyl-2'-(propyloxy)-3,4'-biphenylidicarboxamide;

$N^3$-cyclopropyl-2'-{[3-(dimethylamino)propyl]oxy}-$N^{4'}$-(2,2-dimethylpropyl)5-fluoro-6-methyl-3,4'-biphenylidicarboxamide;

$N^3$-cyclopropyl-$N^{4'}$-(2,2-dimethylpropyl)-5-fluoro-6-methyl-2'-({2-[(methylsulfonyl)amino]ethyl}oxy)-3,4'-biphenylidicarboxamide;

4-[(5'-[(cyclopropylamino)carbonyl]-4-{[(2,2-dimethylpropyl)amino]carbonyl}-3'-fluoro-2'-methyl-2-biphenylyl)oxy]butanoic acid;

2'-[(4amino-4-oxobutyl)oxyl]-$N^3$-cyclopropyl-$N^{4'}$-(2,2-dimethylpropyl)-5-fluoro-6-methyl-3,4'-biphenylidicarboxamide;

$N^3$-cyclopropyl-$N^{4'}$-(2,2-dimethylpropyl)-5-fluoro-6-methyl-2'-{[4-(methylamino)-4-oxobutyl]oxy}-3,4'-biphenylidicarboxamide;

$N^3$-cyclopropyl-$N^{4'}$-(2,2-dimethylpropyl)-5-fluoro-2'-[(4-hydroxybutyl)oxy]-6-methyl-3,4'-biphenylidicarboxamide;

$N^3$-cyclopropyl-$N^{4'}$-(2,2-dimethylpropyl)-5-fluoro-6-methyl-2'-{[3-(1,3,4-oxadiazol-2-yl)propyl]oxy}-3,4'-biphenyldicarboxamide; and $N^3$-cyclopropyl-$N^{4'}$-(2,2-dimethylpropyl)-5-fluoro-2'-(hydroxymethyl)-6-methyl-3,4'-biphenyldicarboxamide;

and pharmaceutically acceptable derivatives thereof.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate or prodrug e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1:Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters, in particular salts.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Salts of the compounds of the present invention may, for example, comprise acid addition salts resulting from reaction of an acid with a nitrogen atom present in a compound of formula (I). Salts encompassed within the term "pharmaceutically acceptable salts" refer to non-toxic salts of the compounds of this invention. Suitable addition salts are formed from acids which form non-toxic salts and examples are acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanesulphonate, formate, fumarate, gluceptate, gluconate, glutamate, glycollylarsanilate, hexylresorcinate, hydrabamine, hydrobromide, hydrochloride, hydrogen phosphate, hydroiodide, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmitate, pantothenate, phosphate/diphosphate, piruvate, polygalacturonate, saccharate, salicylate, stearate, subacetate, succinate, sulphate, tannate, tartrate, teoclate, tosylate, triethiodide, trifluoroacetate and valerate.

Pharmaceutically acceptable base salts include ammonium salts such as a trimethylammonium salt, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Those skilled in the art of organic chemistry will appreciate that many organic compounds can form complexes with solvents in which they are reacted or from which they are precipitated or crystallized. These complexes are known as "solvates". As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceytically acceptable solvents include water, ethanol and acetic acid. Most preferably the solvent used is water. A complex with water is known as a "hydrate". Solvates of the compound of the invention are within the scope of the invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series; Edward B. Roche, ed., Bioreversible Carriers in Drug Design, American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy or amine groups are bonded to any group that, when administered to a patient, cleaves to form the hydroxy or amine groups. Thus, representative examples of prodrugs include (but are not limited to) acetate, formate and benzoate derivatives of alcohol and amine functional groups of the compounds of formula (I). Further, in the case of a carboxylic acid (—COOH), esters may be employed, such as methyl esters, ethyl esters, and the like. Esters may be active in their own right and /or be hydrolysable under in vivo conditions in the human body. Suitable pharmaceutically acceptable in vivo hydrolysable ester groups include those which break down readily in the human body to leave the parent acid or its salt.

As used herein, the term "alkyl" refers to straight or branched hydrocarbon chains containing the specified number of carbon atoms. For example, $C_{1-6}$alkyl means a straight or branched alkyl containing at least 1,and at most 6,carbon atoms. Examples of "alkyl" as used herein include, but are not limited to, methyl, ethyl, n-propyl, n-butyl, n-pentyl, isobutyl, isopropyl, t-butyl and hexyl. A $C_{1-4}$alkyl group is preferred, for example methyl, ethyl or isopropyl. The said alkyl groups may be optionally substituted with one or more fluorine atoms, for example, trifluoromethyl.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2,and at most 6,carbon atoms and containing at least one double bond. Examples of "alkenyl" as used herein include, but are not limited to ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl.

As used herein, the term "alkoxy" refers to straight or branched chain alkoxy groups containing the specified.number of carbon atoms. For. example, $C_{1-6}$alkoxy means a straight or branched alkoxy containing at least 1,and at most 6,carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-5}$cycloalkyl group is preferred, for example cyclopropyl.

As used herein, the terms "heteroaryl ring" and "heteroaryl" refer to a monocyclic five- to seven- membered unsaturated hydrocarbon ring containing at least one heteroatom selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. A particularly preferred heteroaryl ring is pyridyl. The said ring may be optionally substituted by one or more substituents independently selected from $C_{1-6}$alkyl and oxy. The terms "heteroaryl ring" and "heteroaryl" also refer to fused aromatic rings comprising at least one heteroatom selected from oxygen, nitrogen and sulfur. Preferably, the fused ring each have five or six ring atoms. Examples of fused aromatic rings include, but are not limited to, indolyl, isoindolyl, azaindolyl, benzoxazolyl, benzimidazolyl, benzothiazolyl, benzofuranyl, benzothiophenyl, quinolyl, isoquinolyl, quinazolinyl, cinnolinyl and phthalazinyl, in particular benzofuranyl.

As used herein, the terms "heterocyclic rings" and "heterocyclyl" refer to a monocyclic three- to seven-membered saturated or non-aromatic, unsaturated hydrocarbon ring containing at least one heteroatom selected from oxygen, nitrogen and sulfur. Preferably, the heterocyclyl ring has five or six ring atoms. Examples of heterocyclyl groups include, but are not limited to, aziridinyl, pyrrolinyl, pyrrolidinyl, imidazolinyl, imidazolidinyl, pyrazolinyl, pyrazolidinyl, piperidyl, piperazinyl, morpholino and thiomorpholino. Particular examples include, but are not limited to, pyrrolinyl, pyrrolidinyl, imidazolinyl, imidazolidinyl, pyrazolinyl, pyrazolidinyl, piperidyl, piperazinyl, morpholino and thiomorpholino. The said ring may be optionally substituted by one or more substituents independently selected from $C_{1-6}$alkyl and oxy.

As used herein, the terms "halogen" or "halo" refer to the elements fluorine, chlorine, bromine and iodine. Preferred halogens are fluorine, chlorine and bromine. A particularly preferred halogen is fluorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

With regard to stereoisomers, the compounds of structure (I) may have one or more asymmetric carbon atom and may occur as racemates, racemic mixtures and as individual enantiomers or diastereomers. All such isomeric forms are included within the present invention, including mixtures thereof.

Cis (E) and trans (Z) isomerism may also occur. The present invention includes the individual stereolsomers of the compound of the invention and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. A stereoisomeric mixture of the agent may also be prepared from a corresponding optically pure intermediate or by resolution, such as H.P.L.C. of the corresponding racemate using a suitable chiral support or by fractional crystallisation of the diastereoisomeric salts formed by reaction of the corresponding racemate with a suitable optically active acid or base, as appropriate.

Furthermore, some of the crystalline forms of the compounds of structure (I) may exist as polymorphs, which are included in the present invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared In the working Examples.

A compound of formula (I) may be prepared by reacting a compound of (II)

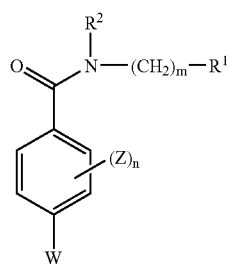

(II)

in which $R^1$, $R^2$, Z, m and n are as hereinbefore defined and W is halogen, in particular bromine or iodine, with a compound of formula (III)

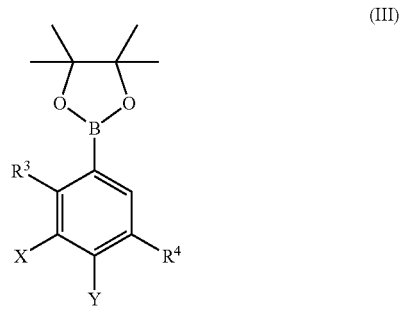

(III)

in which $R^3$, $R^4$, X and Y are as hereinbefore defined, in the presence of a catalyst, for example tetrakis(triphenylphosphine)palladium.

A compound of formula (II) may readily be prepared from a corresponding acid compound of formula (IV)

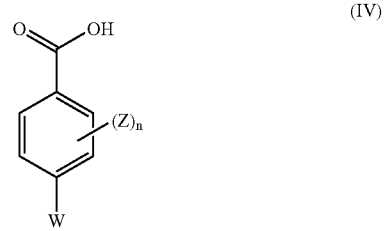

(IV)

in which Z, W and n are as hereinbefore defined, by converting the acid to an activated form of the acid, for example the acid chloride, by treatment with, for example, thionyl chloride, and then reacting the activated acid thus formed with an amine compound of formula (V)

(V)

in which $R^1$, $R^2$ and m are as hereinbefore defined, under amide forming conditions.

Suitable amide forming conditions are well known in the art and include treating a solution of the acid of formula (IV), or the activated form thereof, in for example acetone or dichloromethane, with an amine of formula (V) in the presence of sodium carbonate.

A compound of formula (III) may be prepared by reacting a compound of formula (VI)

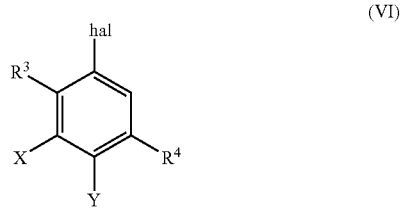

(VI)

in which $R^3$, $R^4$, X and Y are as hereinbefore defined and hal is halogen, in particular bromine or iodine, with bis(pinnacolato)diboron, $PdCl_2dppf$ and potassium acetate in a solvent such as DMF.

Alternatively, when $R^4$ is —CO—NH—$(CH_2)_p$—$R^8$, a compound of formula (III) may be prepared by reacting an acid compound of formula (VII)

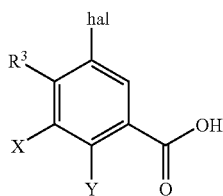

(VII)

in which $R^3$, hal, X and Y are as hereinbefore defined, with bis(pinnacolato)diboron, $PdCl_2dppf$ and potassium acetate in a solvent such as DMF, and then forming an amide by reaction with an amine compound of formula (V) as hereinbefore defined.

A compound of formula (I) may also be prepared by reacting a compound of formula (VIII)

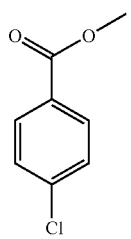

(VIII)

with a compound of formula (III) as hereinbefore defined and then reacting the acid thus formed with an amine of formula (V) as hereinbefore defined, under amide forming conditions.

Additionally, a compound of formula (I) may be prepared by reacting a compound of (II) as hereinbefore defined with a compound of formula (IX)

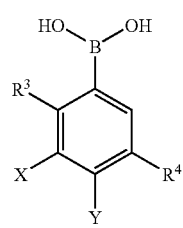

(IX)

in which $R^3$, $R^4$, X and Y are as hereinbefore defined, in the presence of a catalyst, for example tetrakis(triphenylphosphine)palladium.

Additionally, a compound of formula (I) may be prepared by reacting a compound of formula (X)

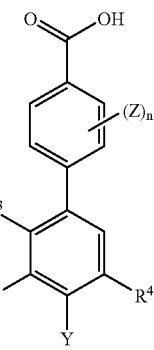

(X)

in which $R^3$, $R^4$, X, Y, Z and n are as hereinbefore defined, with an amine compound of formula (V) as hereinbefore defined, under amide forming conditions.

A compound of formula (X) may be prepared by reacting a compound of formula (XI)

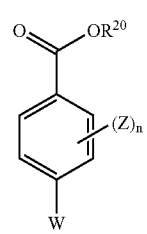

(XI)

in which W, Z and n are as hereinbefore defined and $R^{20}$ is $C_{1-6}$alkyl, in particular methyl or ethyl, with a compound of formula (III) or a compound of formula (IX) as hereinbefore defined, in the presence of a catalyst, for example tetrakis(triphenylphosphine)palladium, and removing the $R^{21}$ group, if necessary, by treatment with a base such as sodium hydroxide in a solvent such as methanol.

A further general method comprises final stage modification of one compound of formula (I) into another compound of formula (I). Suitable functional group transformations for converting one compound of formula (I) into another compound of formula (I) are well known in the art and are described in, for instance, *Comprehensive Heterocyclic Chemistry II*, eds. A. R. Katritzky, C. W. Rees and E. F. V. Scriven (Pergamon Press, 1996), *Comprehensive Organic Functional Group Transformations*, eds. A. R. Katritzky, O. Meth-Cohn and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989).

Alternatively, a compound of formula (I) may be prepared from a compound of formula (XII)

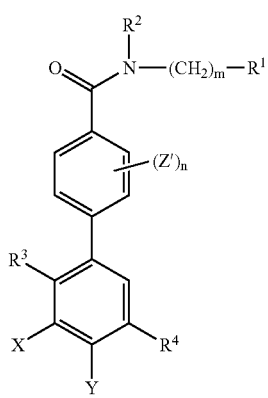

(XII)

in which Z' is a group convertible to Z as defined for formula (I). Conversion of a Z' group may arise if, for example, an alternative group such as a halogen group or a protecting group is present during the reactions described above. A comprehensive discussion of protecting groups and methods for cleaving protected derivatives is given in for example T. W. Greene and P. G. M Wuts in Protective Groups in Organic Synthesis $2^{nd}$ ed., John Wiley & Son, Inc 1991.

For example, one general method for preparing thte compounds of formula (I) comprises the reactions set out in Scheme 1 below.

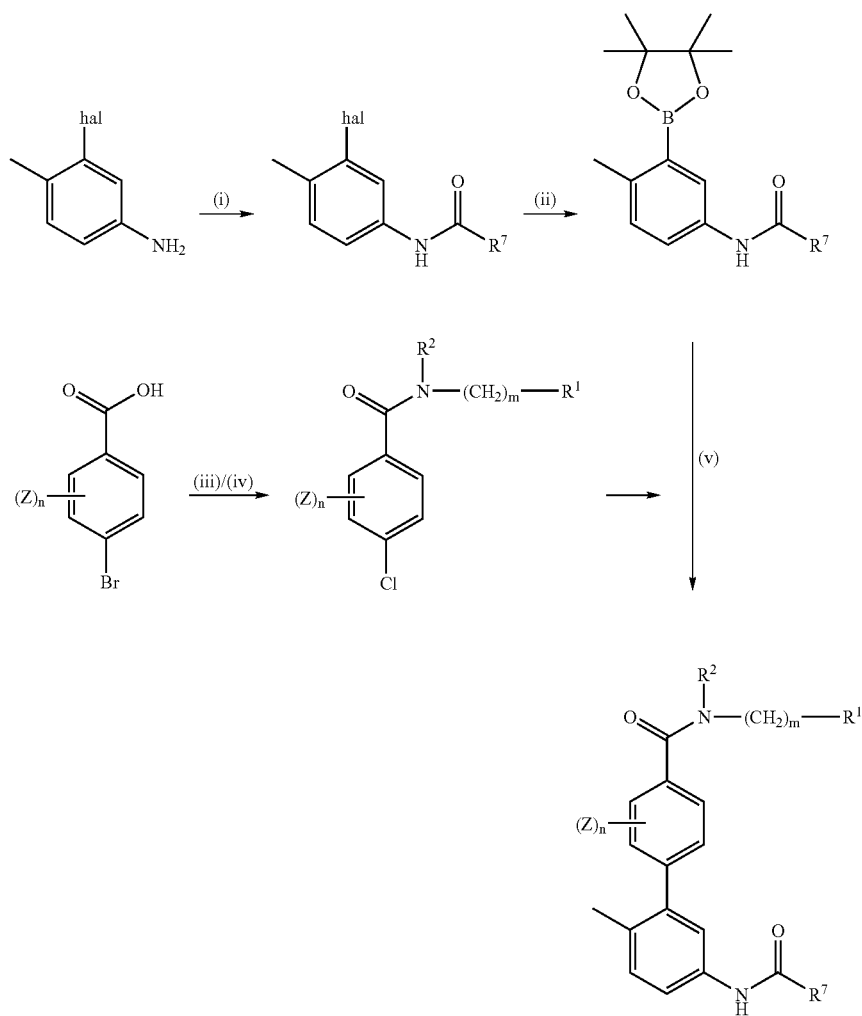

Scheme 1 i. R⁷CO₂H, HATU, DIPEA, DMF.
ii. Bis(pinnacolato)diboron, PdCl₂dppf, KOAc, DMF.
iii. SOCl₂.
iv. R¹(CH₂)$_m$NHR², Na₂CO₃, acetone.
v. Na₂CO₃, tetrakis(triphenylphosphine)palladium, propan-2-ol.

For example, another general method for preparing the compounds of formula (I) comprises the reactions set out in Scheme 2 below.

i. SOCl₂.
ii. R⁸(CH₂)$_p$NH₂, Na₂CO₃, acetone.
iii. Bis(pinnacolato)diboron, PdCl₂dppf, KOAc, DMF.
iv. SOCl₂.
v. R¹(CH₂)$_m$NHR², Na₂CO₃, acetone.
vi. Na₂CO₃, tetrakis(triphenylphosphine)palladium, propan-2-ol.

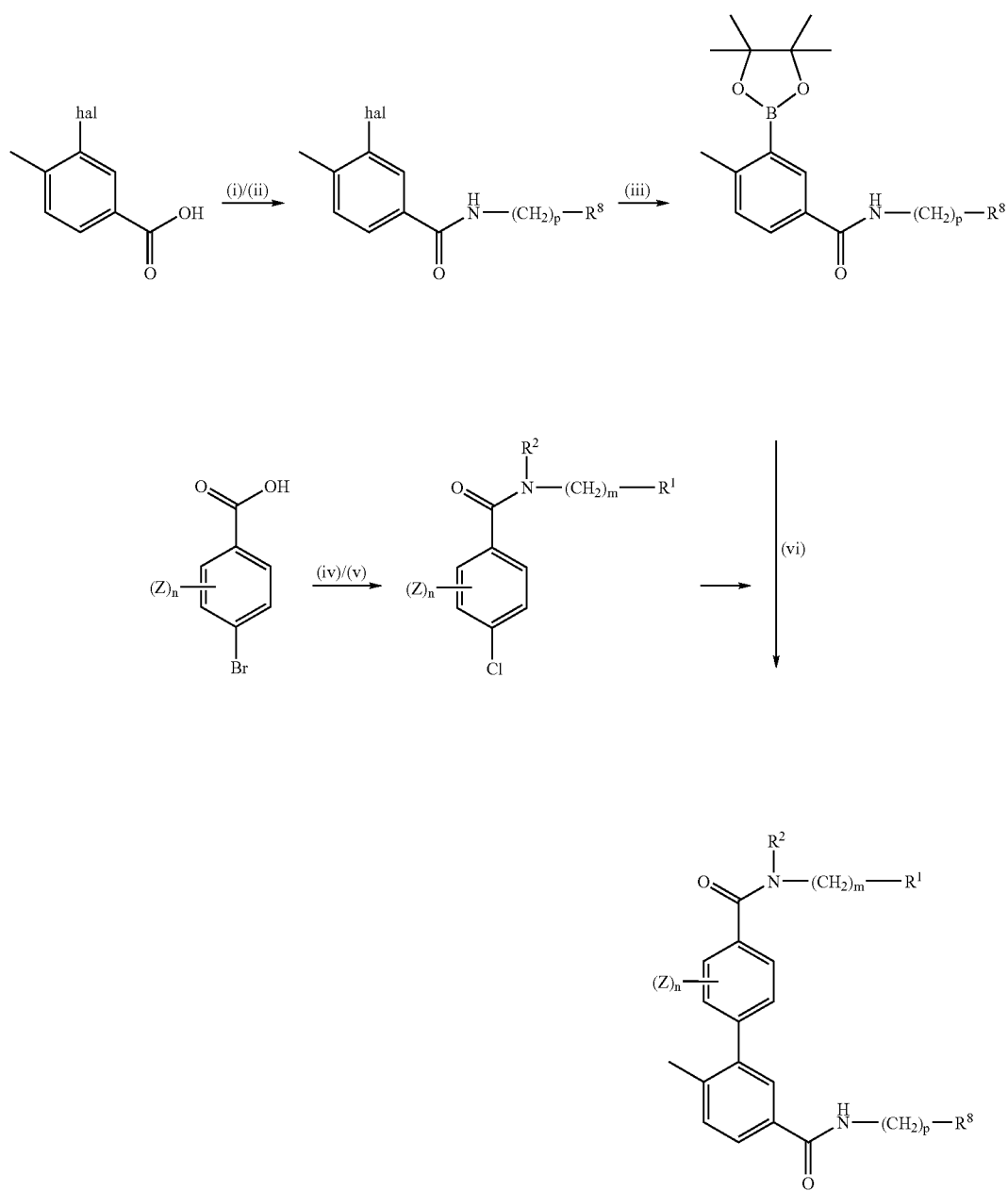

Scheme 2

For example, another general method for preparing the compounds of formula (I) comprises the reactions set out in Scheme 3 below.

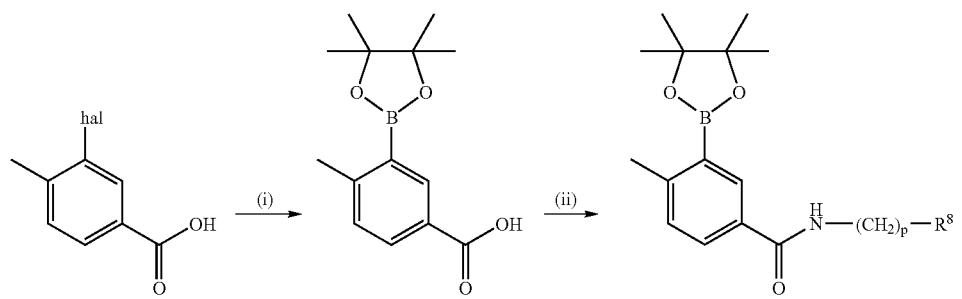

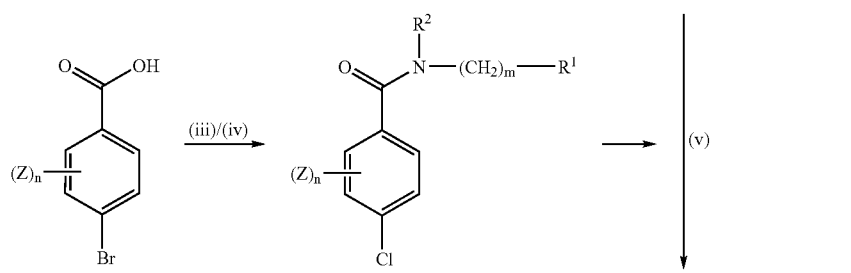

i. Bis(pinnacolato)diboron, PdCl$_2$dppf, KOAc, DMF.
ii. R$^8$(CH$_2$)$_p$NH$_2$, HATU, DIPEA, DMF.
iii. SOCl$_2$.
iv. R$^1$(CH$_2$)$_m$NHR$^2$, Na$_2$CO$_3$, DCM.
v. Na$_2$CO$_3$, tetrakis(triphenylphosphine)palladium, propan-2-ol.

For example, another general method for preparing the compounds of formula (I) comprises the reactions set out in Scheme 4 below.

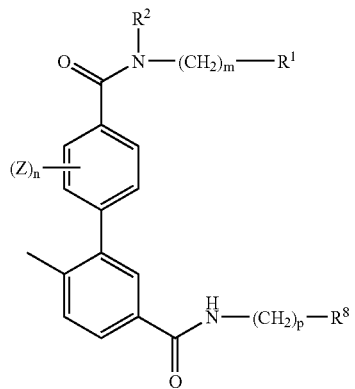

Scheme 4

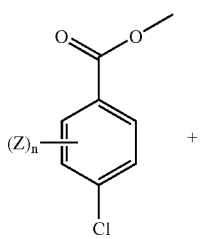

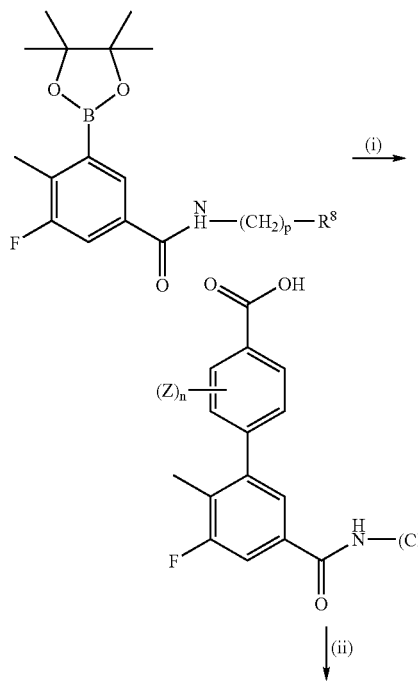
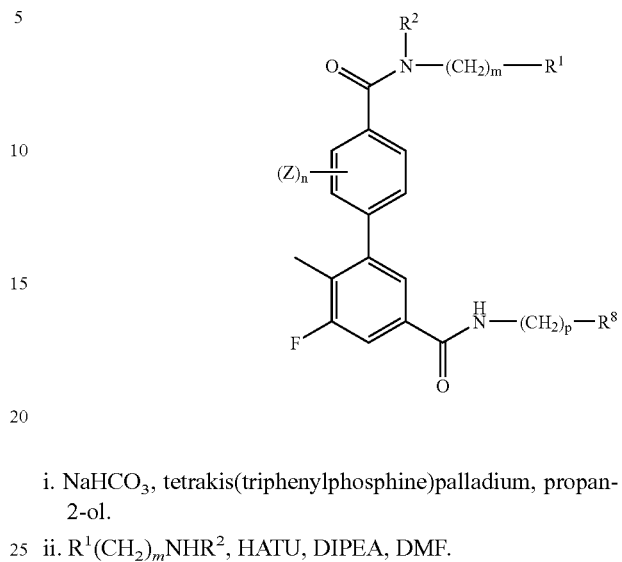
i. NaHCO$_3$, tetrakis(triphenylphosphine)palladium, propan-2-ol.
ii. R$^1$(CH$_2$)$_m$NHR$^2$, HATU, DIPEA, DMF.
For example, another general method for preparing the compounds of formula (I) comprises the reactions set out in Scheme 5 below.
Scheme 5
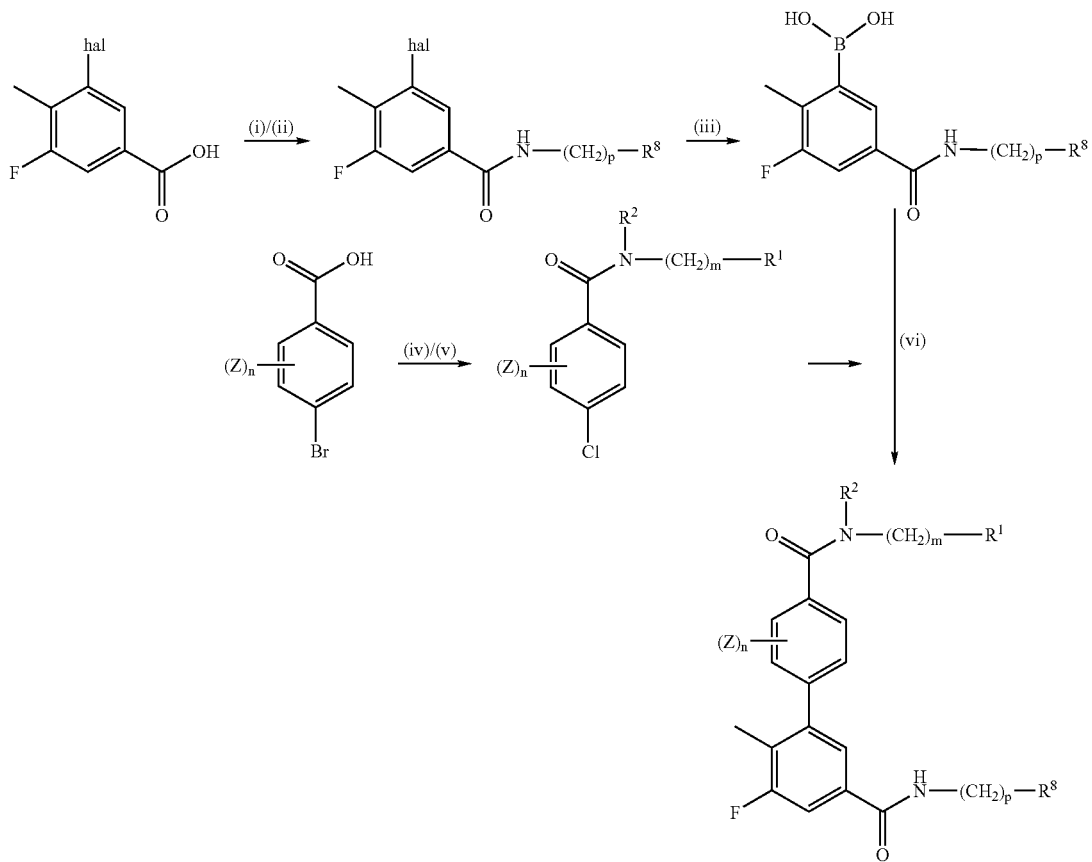

i. $SOCl_2$.
ii. $R^8(CH_2)_pNH_2$, $Na_2CO_3$, DCM.
iii. NaH, n-BuLi, THF, $(iPrO)_3B$.
iv. $SOCl_2$.
v. $R^1(CH_2)_mNHR^2$, $Na_2CO_3$, DCM.
vi. $NaHCO_3$, tetrakis(triphenylphosphine)palladium, propan-2-ol.

For example, another method for preparing the compounds of formula (I) comprises the reactions set out in Scheme 6 below.

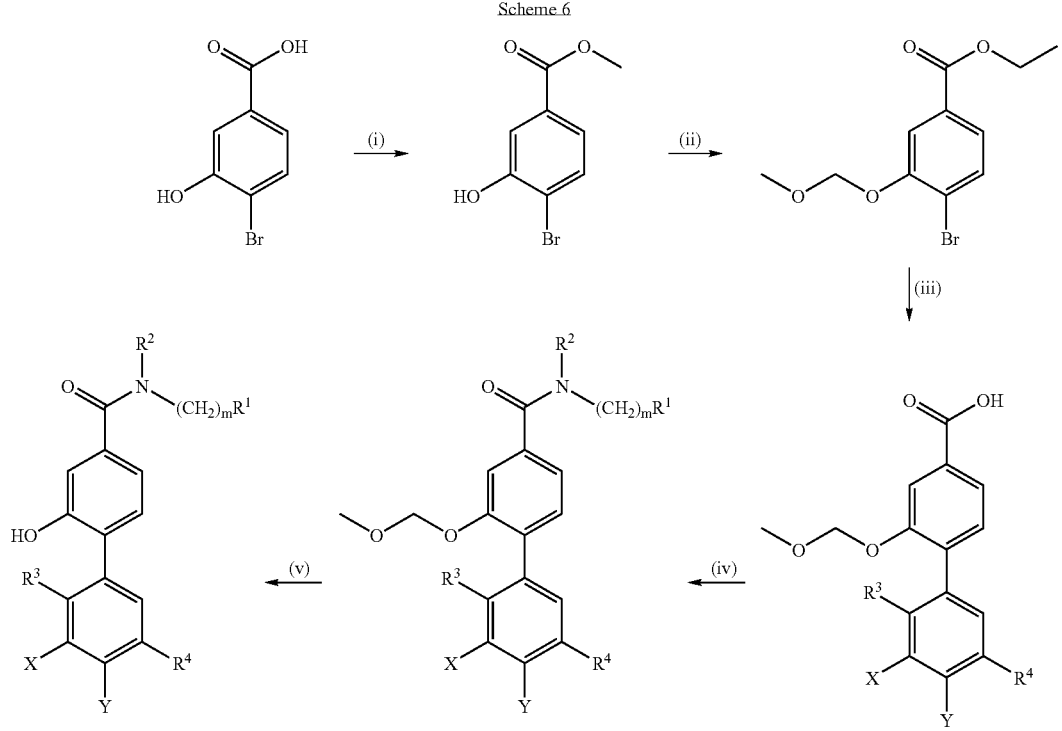

(i) conc. $H_2SO_4$, EtOH
(ii) $(MeO)_2CH_2$, $P_2O_5$, DCM
(iii) (III) or (IX), $(Ph_4P)_3Pd$, $NaHCO_3$, IPA
(iv) $R^1(CH_2)_mNHR^2$, HATU, DIPEA, DMF
(v) HCl, dioxane For example, another method for preparing the compounds of formula (I) comprises the reactions set out in Scheme 7 below.

Scheme 7

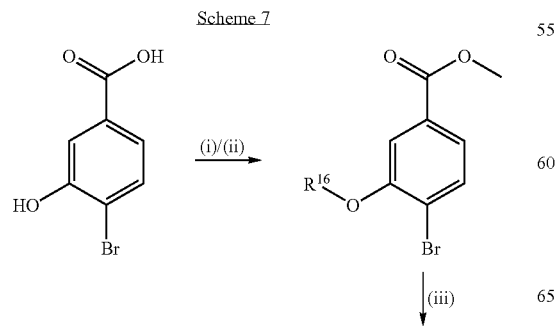

-continued

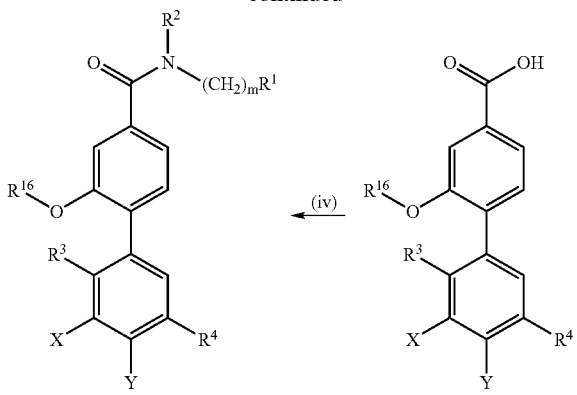

(i) conc. $H_2SO_4$, MeOH
(ii) $R^{16}I$, $K_2CO_3$, Acetone
(iii) (III) or (IX), $(Ph_3P)_4Pd$, $NaHCO_3$, IPA
(iv) NaOH, MeOH
(v) $R^1(CH_2)_mNHR^2$, HATU, DIPEA, DMF For example, another method for preparing the compounds of formula (I) comprises the reactions set out in Scheme 8 below.

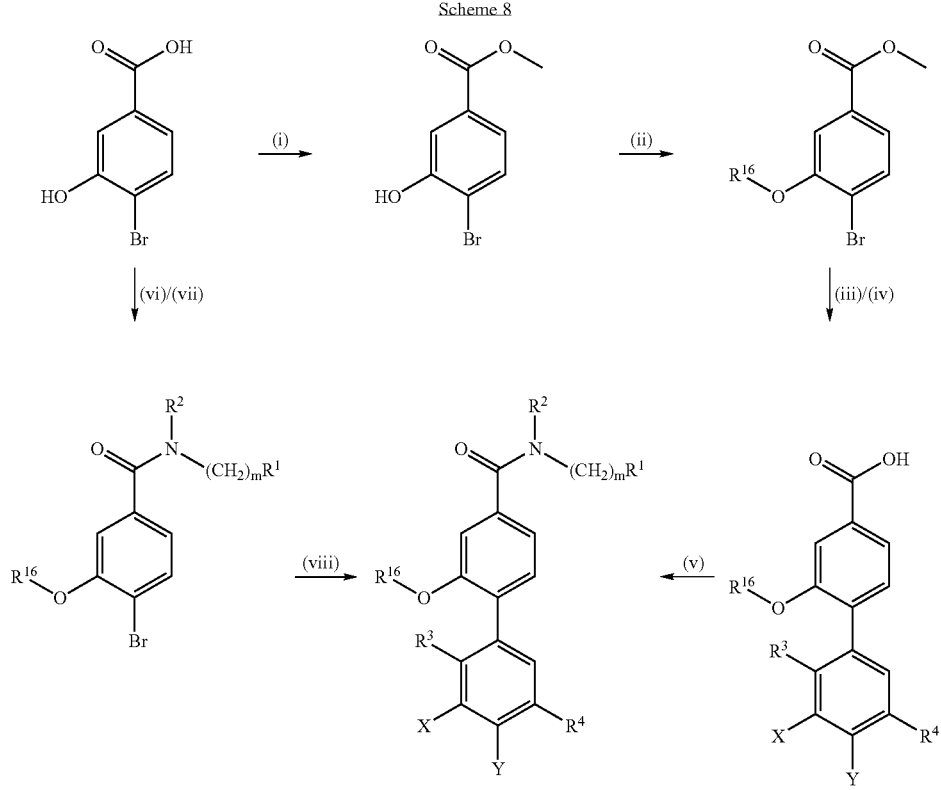

Scheme 8

(i) conc. $H_2SO_4$, MeOH
(ii) $R^{18}OH$, ADDP, $Bu_3P$, toluene
(iii) (III) or (IX), $(Ph_3P)_4Pd$, $NaHCO_3$, IPA
(iv) NaOH, MeOH
(v) $R^1(CH_2)_mNHR^2$, HATU, DIPEA, DMF
(vi) $R^1(CH_2)_mNHR^2$, HATU, DIPEA, DMF
(vii) $R^{16}OH$, ADDP, $Bu_3P$, toluene
(viii) (III) or (IX), $(Ph_3P)_4Pd$, $NaHCO_3$, IPA For example, another method for preparing the compounds of formula (I) comprises the reactions set out in Scheme 9 below.

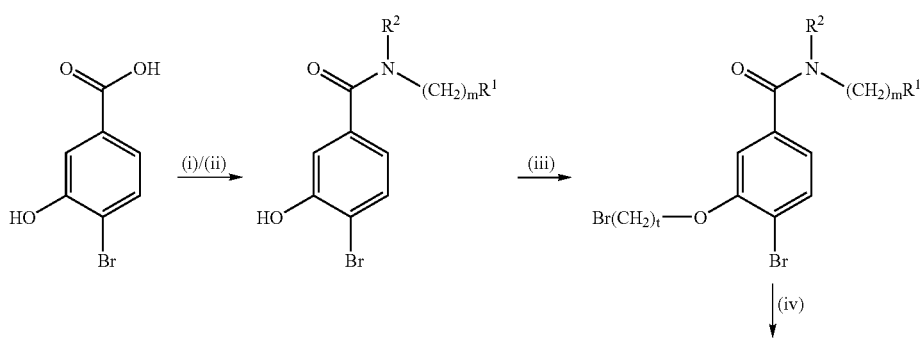

Scheme 9

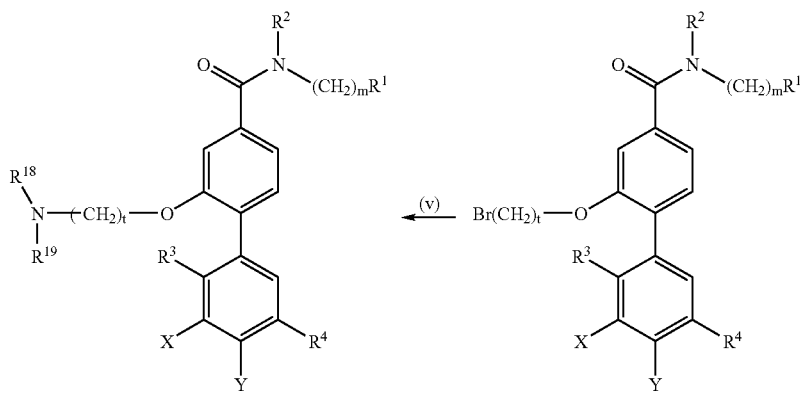

(i) SOCl$_2$
(ii) R$^1$(CH$_2$)$_m$NHR$^2$, Na$_2$CO$_3$, DCM
(iii) Br(CH$_2$)$_t$OH, ADDP, BU$_3$P, toluene
(iv) (III) or (IX), (Ph$_3$P)$_4$Pd, NaHCO$_3$, IPA
(v) R$^{18}$NHR$^{19}$, CHCl$_3$ For example, another method for preparing the compounds of formula (I) comprises the reactions set out in Scheme 10 below.

(i) I(CH$_2$)$_t$CO$_2$Me, NaH, DMF
(ii) (III) or (IX), (Ph$_3$P)$_4$Pd, NaHCO$_3$, IPA
(iii) NaOH, MeOH
(iv) R$^{18}$NHR$^{19}$, HATU, DIPEA, DMF For example, another method for preparing the compounds of formula (I) comprises the reactions set out in Scheme 11 below.

Scheme 10

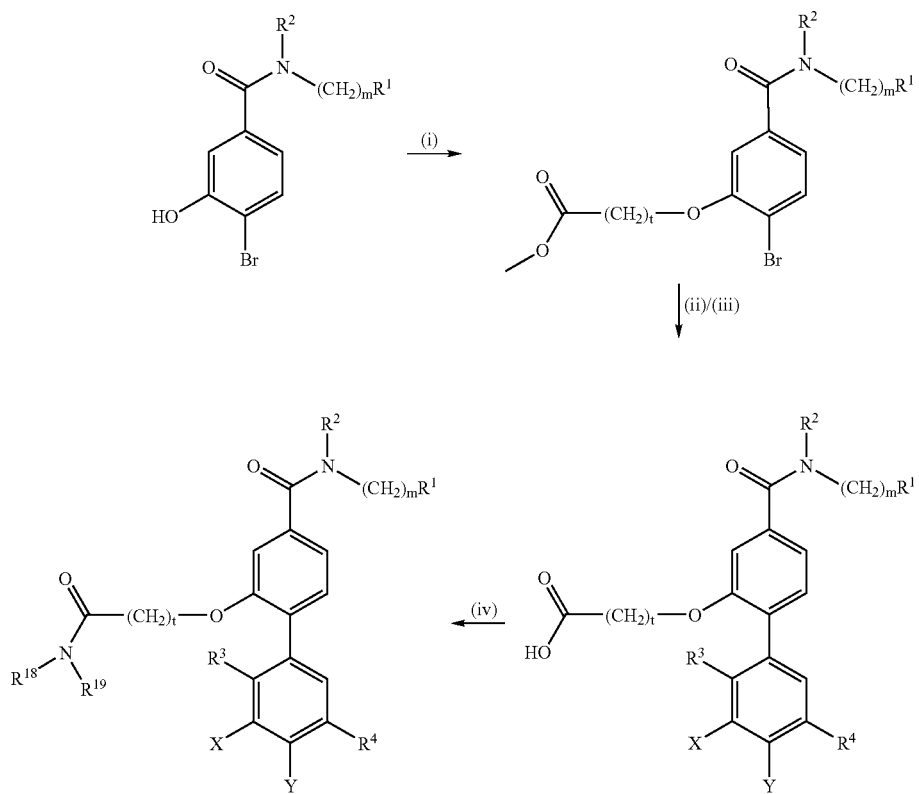

Scheme 11
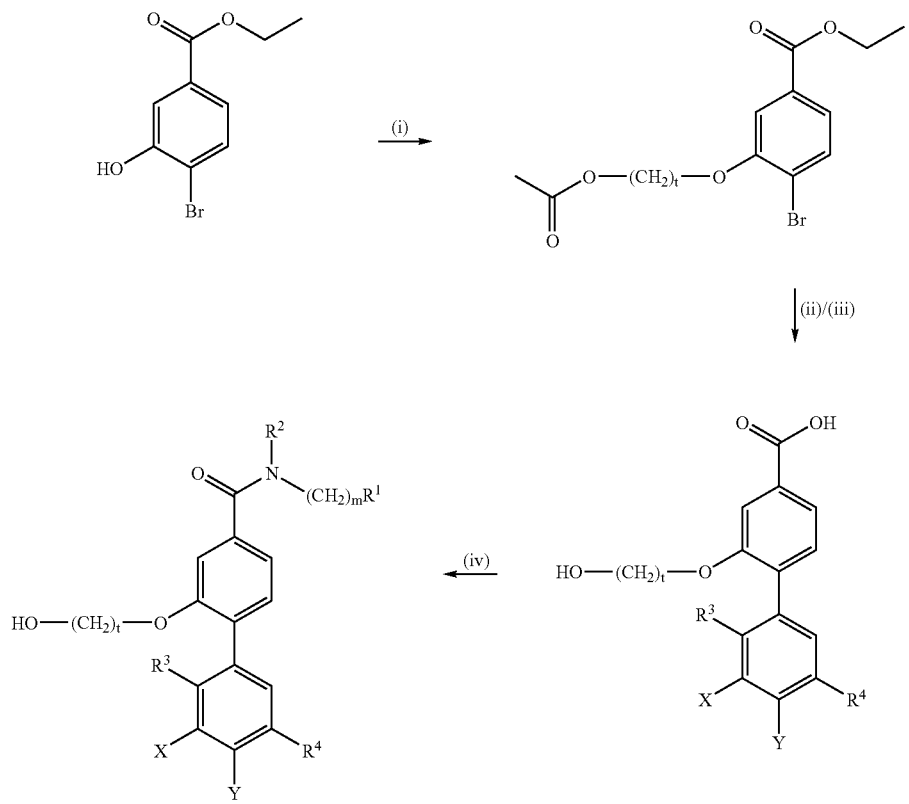
(I) AcO(CH$_2$)$_t$OH, NaH, DMF
(ii) (III) or (IX), (Ph$_3$P)$_4$Pd, NaHCO$_3$, IPA
(iii) NaOH, MeOH
(iv) R$^1$(CH$_2$)$_m$NHR$^2$, HATU, DIPEA, DMF
For example, another method for preparing the compounds of formula (I) comprises the reactions set out in Scheme 12 below.
Scheme 12
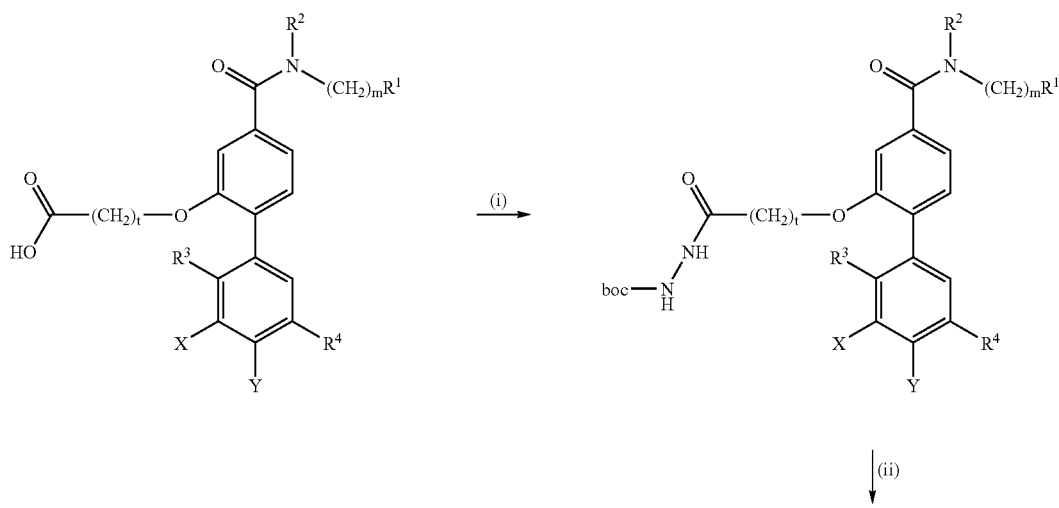

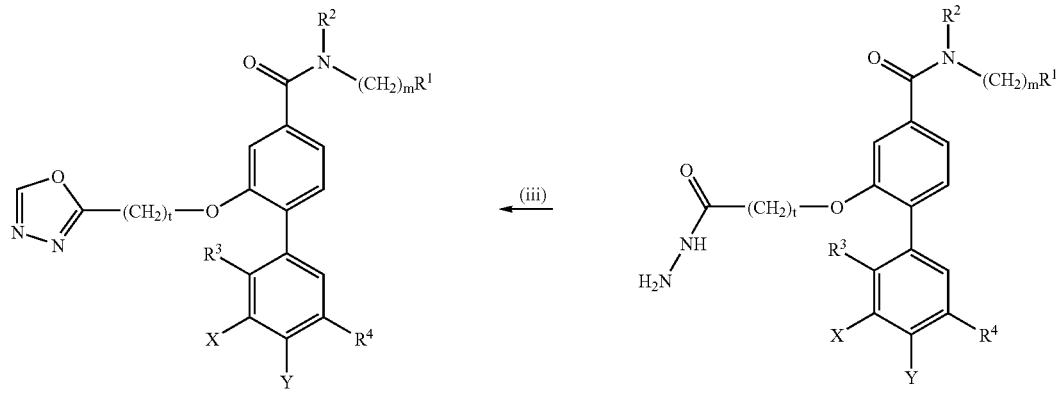

(i) bocNHNH₂, HATU, DIPEA, DMF
(ii) HCl, dioxane
(iii) Triethylorthoformate

For example, another method for preparing the compounds of formula (I) comprises the reactions set out in Scheme 13 below.

(i) NaH, DMF
(ii) (III) or (IX), (Ph₃P)₄Pd, NaHCO₃, IPA
(iii) HCl, dioxane

For example, another method for preparing the compounds of formula (I) comprises the reactions set out in Scheme 14 below.

Scheme 13

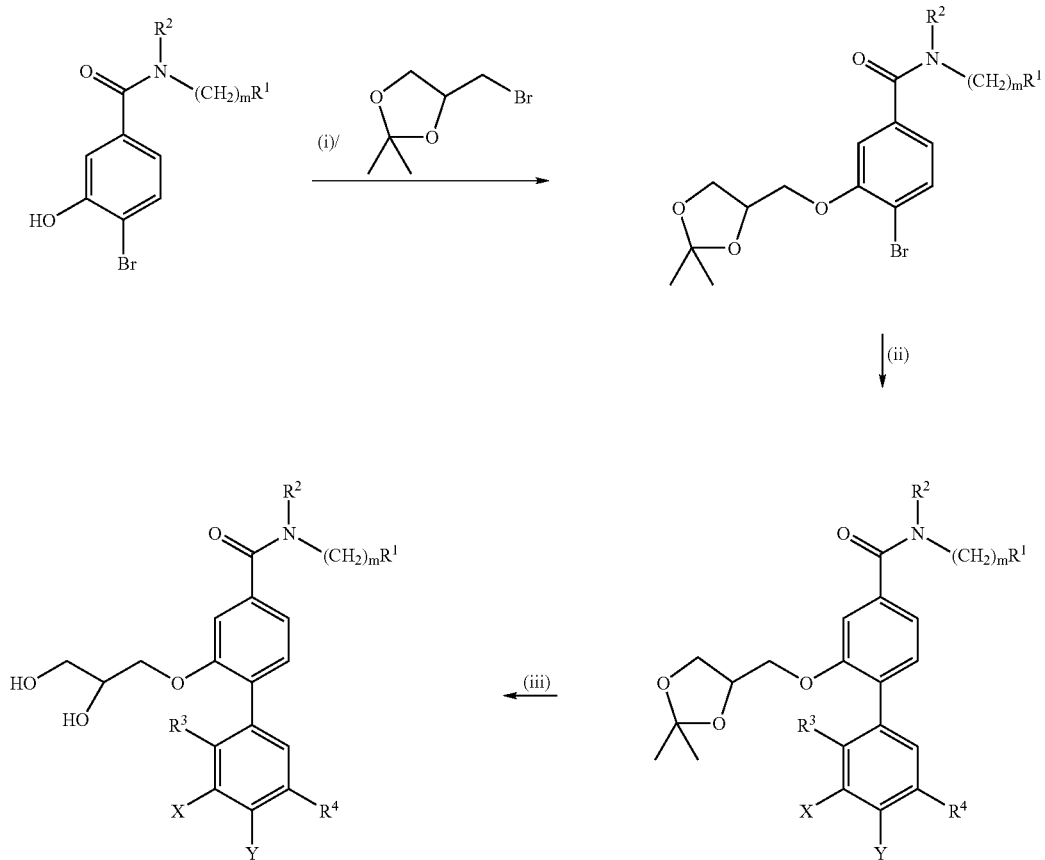

Scheme 14
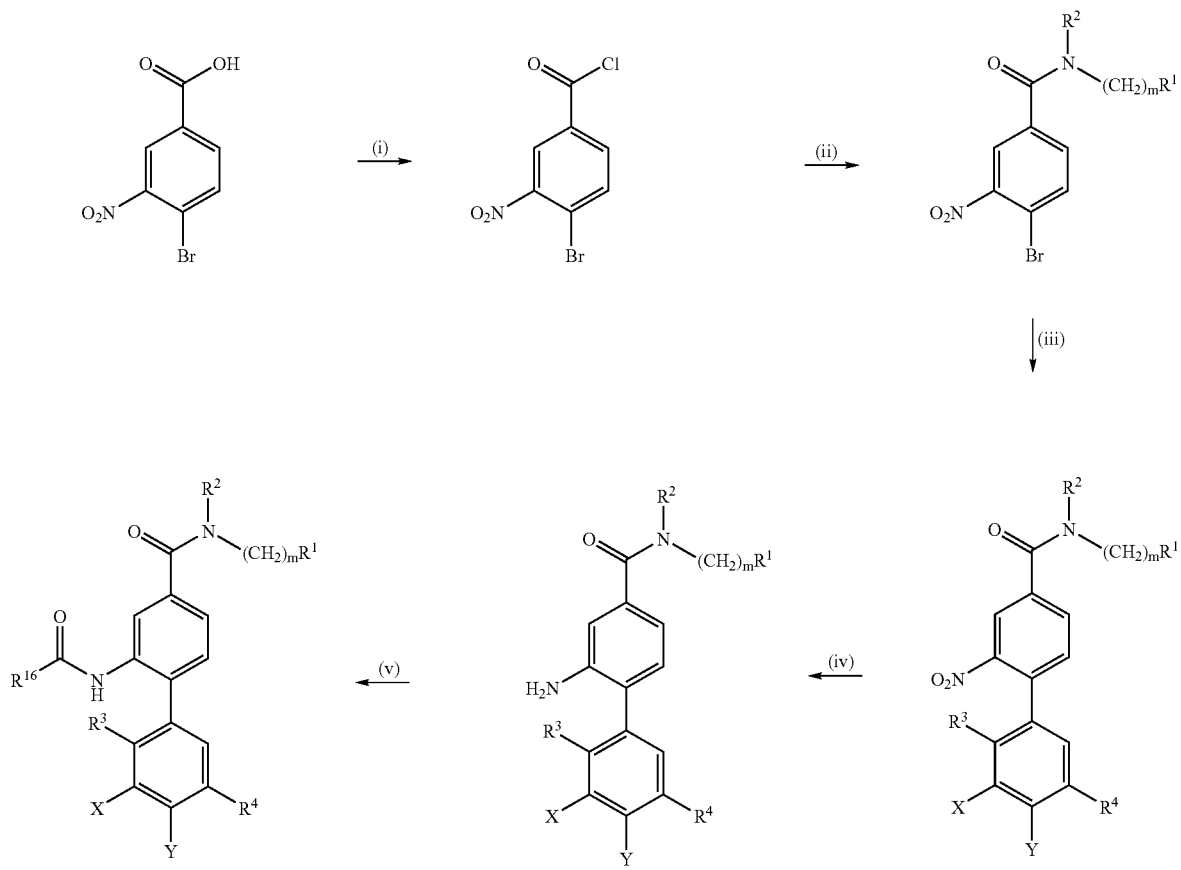
(I) SOCl₂
(ii) R¹(CH₂)ₘNHR², Na₂CO₃, DCM
(iii) (III) or (IX), (Ph₃P)₄Pd, NaHCO₃, IPA
(iv) Pd/C, EtOH, H₂
(v) R¹⁶COCl, Na₂CO₃, DCM
For example, another method for preparing the compounds of formula (I) comprises the reactions set out in Scheme 15 below.
Scheme 15
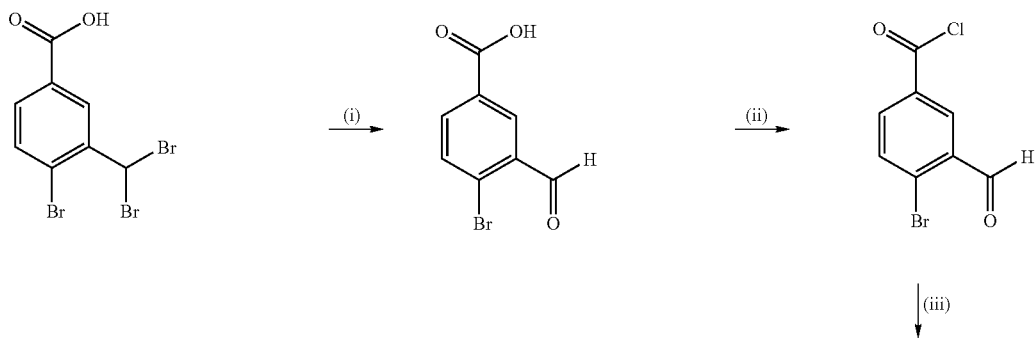

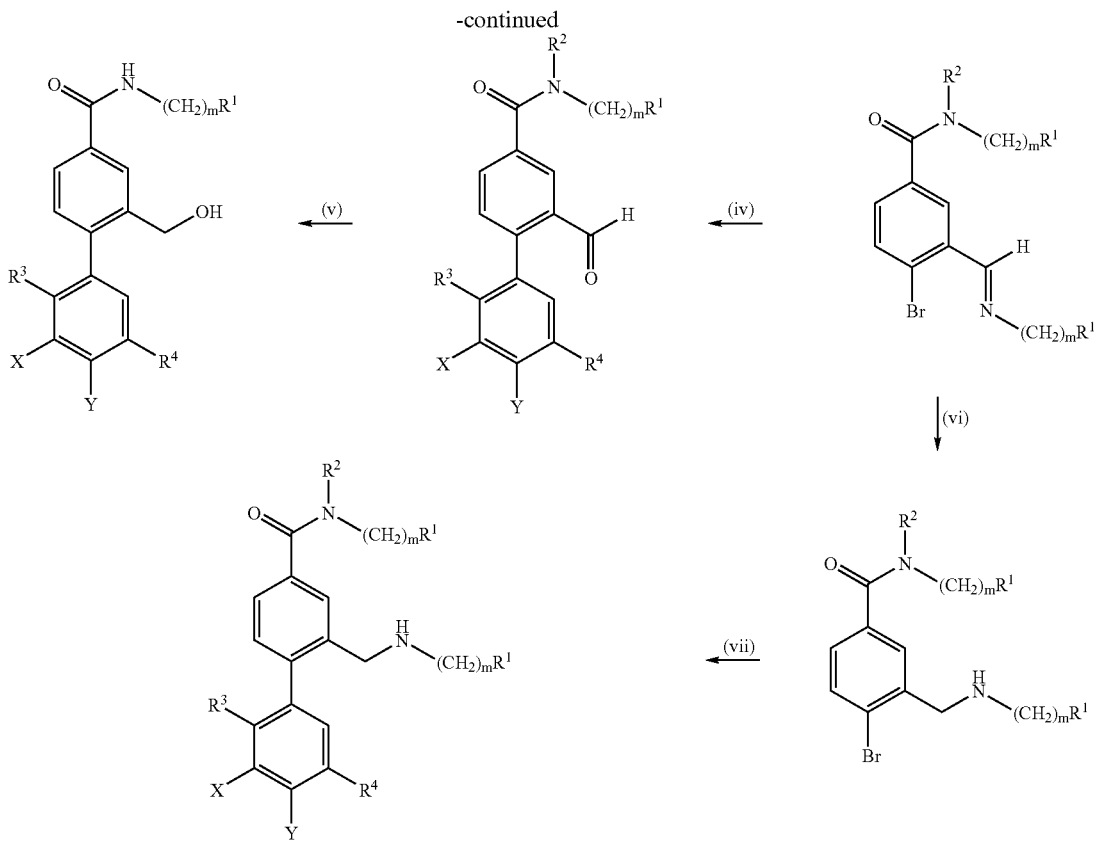
(i) Na$_2$CO$_3$, H$_2$O
(ii) SOCl$_2$
(iii) R$^1$(CH$_2$)$_m$NHR$^2$, Et$_3$N, DCM
(iv) (III) or (IX), (Ph$_3$P)$_4$Pd, NaHCO$_3$, IPA
(v) NaBH$_4$, EtOH
(vi) Na(AcO)$_3$BH, THF
(vi) (III) or (IX), (Ph$_3$P)$_4$Pd, NaHCO$_3$, IPA
For example, a further method for preparing the compounds of formula (I) comprises the reactions set out in Scheme 16 below.
Scheme 16
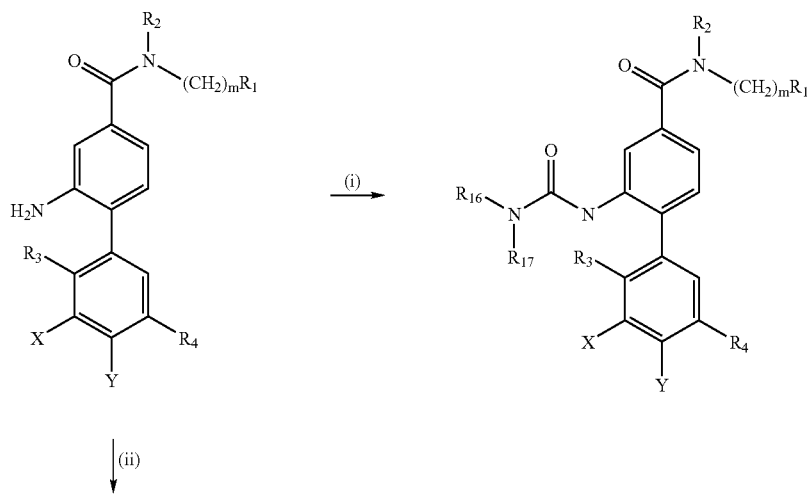

-continued

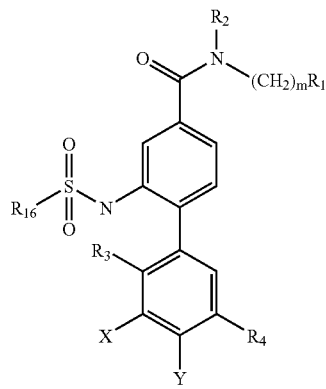

(i) CDI, DIPEA, DMAP, $R^{16}R^{17}NH$, DCM
(ii) $R^{16}SO_2NH_2$, DIPEA, DMAP, pyridine.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyidimethylsilyl; alkyl ethers such as tetrahydropyranyl or tert-butyl; or esters such as acetate.

Whilst it is possible for the compounds of the present invention to be administered as the raw chemical, the compounds of formula (I) and their pharmaceutically acceptable derivatives are conveniently administered in the form of pharmaceutical compositions eg when the agent is in admixture with a suitable pharmaceutical excipient, diluent and/or carrier selected with regard to the Intended route of administration and standard pharmaceutical practice.

Thus, in another aspect of the invention, we provide a pharmaceutical composition comprising at least one compound of formula (I) or a pharmaceutically acceptable derivatve thereof, in association with one or more pharmaceutically acceptable excipients, diluents and/or carriers. The excipient, diluent or carrier must be "acceptable" in the sense of being compatible with the other ingredients of the formulation and not deleterious to the receipient thereof.

According to a further aspect, the invention provides a pharmaceutical composition comprising, as active ingredient, at least one compound of the invention or a pharmaceutically acceptable derivative thereof, in association one or more pharmaceutically acceptable excipients, diluents and/or carriers for use in therapy, and in particular in the treatment of human or animal subjects suffering from a condition susceptible to amelioration by an inhibitor of p38 kinase.

The present invention also provides a pharmaceutical composition comprising a therapeutically effective amount of the compounds of the present invention and a pharmaceutically acceptable excipient, diluent and/or carrier (including combinations thereof).

There is further provided by the present invention a process of preparing a pharmaceutical composition, which process comprises mixing at least one compound of the invention or a pharmaceutically acceptable derivative thereof, together with a pharmaceutically acceptable excipient, diluent and/or carrier.

The pharmaceutical compositions may be for human or animal usage in human and veterinary medicine and will typically comprise any one or more of a pharmaceutically acceptable excipient, diluent or carrier. Acceptable carriers or diluents for therapetic use are well known in the pharmaceutical art, and are described, for example, in Remington's Pharmaceutical Sciences, Mack Publishing Co. (A. R. Gennaro edit. 1985). The choice of pharmaceutical excipient, diluent or carrier can be selected with regard to the intended route of administration and standard pharmaceutical practice. The pharmaceutical compositions may comprise as—or in addition to—the excipient, diluent or carrier any suitable binder(s), lubricant(s), suspending agent(s), coating agent(s) and solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e. g. as a carrier, diluent or solubiliser. Alpha-, beta- and gamma-cyclodextrins are most commonly used and suitable examples are described in WO 91/11172, WO 94/02518 and WO 98/55148.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see WO 02/00196 (SmithKline Beecham).

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solubon, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The routes for administration (delivery) include, but are not limited to, one or more of: oral (e. g. as a tablet, capsule, or as an ingestable solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. It is to be understood that not all of the compounds need be administered by the same route. Likewise, if the composition comprises more than one active component, then those components may be administered by different routes.

The compounds of formula (I) and their pharmaceutically acceptable salts and solvates may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives. In a preferred embodiment, the agents of the present invention are delivered systemically such as orally, buccally or sublingually. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), ovules, pills, powders, granules, elixirs, tinctures, emulsions, solutions, syrups or suspensions prepared by conventional means with acceptable excipients for immediate-, delayed-, modified-, sustained-, pulsed- or controlled-release applications.

For instance, for oral administration in the form of a tablet or capsule, the active drug component can be combined with an oral, non-toxic pharmaceutically acceptable inert carrier such as ethanol, glycerol, water and the like. The tablets may also contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent; and/or by using infusion techniques. For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle. For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compositions of the present invention may be administered by direct injection.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water.

Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, a hydrofluoroalkane such as tetrafluoroethane or heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or Insufflator may be formulated containing a powder mix of a compound of the invention and a suitable powder base such as lactose or starch.

Alternatively, the compound of the present invention can be administered in the form of a suppository or pessary, or it may be applied topically in the form of a gel, hydrogel, lotion, solution, cream, ointment or dusting powder.

The compounds of the present invention may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The pharmaceutical compositions generally are administered in an amount effective for treatment or prophylaxis of a specific condition or conditions. Initial dosing in humans is accompanied by clinical monitoring of symptoms, such symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the activity of the specific compound to be employed, the metabolic stability and length of action of that compound, age, weight, general health, sex, diet, mode and time of administration, rate of excretion, drug combination, severity of the particular condition and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial. For oral and parenteral administration to humans, the daily dosage level of the agent may be in single or divided doses.

In another aspect, the present invention provides a compound of formula (I) or a pharmaceutically acceptable derivative thereof, for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β isoforms. Assays for determining the selectivity of compounds for the p38 isoforms are described in, for example, WO 99/61426, WO 00/71535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I) or a pharmaceutically acceptable derivative thereof. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments. It will be appreciated that reference to treatment includes acute treatment or prophylaxis as well as the alleviation of established symptoms.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivibs, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, chronic pulmonary inflammation, chronic obstructive pulmonary disease, neurodegenerative disease, Alzheimer's disease, Parkinson's disease and epilepsy which comprises administering to said subject a therapeutically effective amount of a compound of formula (I) or a pharmaceutically acceptable derivative thereof.

A further aspect of the invention provides a method of treatment of a human or animal subject suffering from any type of pain including chronic pain, rapid onset of analgesia, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable derivative thereof.

A further aspect of the invention provides the use of a compound of formula (I), or a pharmaceutically acceptable derivative thereof, in the manufacture of a medicament for use in the treatment of a condition or disease state mediated by p38 kinase activity or mediated by cytokines produced by p38 kinase activity.

The compounds of formula (I) and their derivatives may be employed alone or in combination with other therapeutic agents for the treatment of the above-mentioned conditions. The invention thus provides, in a further aspect, a combination comprising a compound of the invention or a pharmaceutically acceptable derivative thereof together with a further therapeutic agent.

In particular, in rheumatoid arthritis therapy, combination with other chemotherapeutic or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) or pharmaceutically acceptable salt(s) or solvate(s) thereof and the other pharmaceutically active agent(s) may be administered together or separately and, when administered separately, this may occur separately or sequentially in any order. The amounts of the compound(s) of formula (I) or pharmaceutically acceptable salt(s) or solvate(s) thereof and the other pharmaceutically active agent(s) and the relative timings of administration will be selected in order to achieve the desired combined therapeutic effect. Appropriate doses will be readily appreciated by those skilled in the art. It will be appreciated that the amount of a compound of the invention required for treatment will vary with the nature of the condition. being treated and the age and condition of the patient and will ultimately be at the discretion of the attendant physician or veterinarian. Examples of other pharmaceutically adtive agents which may be employed in combination with compounds of formula (I) and their salts and solvates for rheumatoid arthritis therapy include: immunosuppresants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1Receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention.

The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

EXAMPLES

The following examples are an illustrative embodiment of the invention, not limiting the scope of the invention in any way. Reagents are commercially available or are prepared according to procedures in the literature.

N-(2-Iodoethyl)methanesulfonamide was prepared according to the procedure described in Bioorganic & Medicinal Chemistry Letters (1995), 5(18), 2119-22.

4-(2-Iodoethyl)morpholine was prepared according to the procedure described in Journal of Antibiotics (1989), 42(7), 1133-44.

4-(Bromoacetyl)morpholine was prepared according to the procedure described in Journal of Organic Chemistry (2003), 68(6), 2143-2150.

4-(Bromomethyl)-2,2-dimethyl-1,3-dioxolane was prepared according to the procedure described in Catalysis Letters (2001), 75(3-4), 205-207.

4Bromo-3-hydroxybenzoic acid and ethyl 4-bromo-3-hydroxybenzoate were prepared according to the procedures described by Dawson, Marcia I.; Fontana, Joseph A.; Zhang, Xiao-Kun; Leid, Mark; Jong, Ling; and Hobbs, Peter in WO 03/048101.

Neopentylamine may be purchased from Fluorochem Ltd.

(R)-(−)-3-Methyl-2-butylamine may be purchased from ABCR and Lancaster.

R-3,3-Dimethyl-2-butylamine may be purchased from commercial suppliers including ABCR and Lancaster.

Methyl 4-bromo-3-hydroxybenzoate was prepared according to the procedure described by Nazare, Marc; Will, David William; Peyman, Anuschirwan; Matter, Hans; Zoller, Gerhard; and Gerlach, Uwe in EP 1 217 000 A1.

Methyl 4-Iodobutyrate may be purchased from Aldrich and Ubichem.

{5-[(Cyclopropylamino)carbonyl]-3-fluoro-2-methylphenyl}boronic acid was prepared according to the procedure described in WO 03/068747.

4-Bromo-3-(dibromomethyl)benzoic acid was prepared by the procedure described in WO 02/032884.

4-Bromo-3-nitrobenzoic acid was prepared by the procedure described in WO 01/027088.

LCMS was conducted on a column (3.3 cm×4.6 mm ID, 3um ABZ+PLUS), at a Flow Rate of 3 ml/min, Injection Volume of 5 µl, at room temperature and UV Detection Range at 215 to 330 nm.

Intermediate 1

N-Cyclopropylmethyl-3-[2-(N,N-dimethylamino)ethoxy]-4-iodobenzamide

3-[2-(N,N-Dimethylamino)ethoxy]-4-iodobenzoic acid (Intermediate 2) (100 mg) was heated at 90° C. in thionyl chloride (2 ml) for 2.5 hours. The excess thionyl chloride was evaporated under vacuum and the residue dissolved in DCM (5 ml). Sodium carbonate (148 mg) and cyclopropylmethylamine (0.126 ml) were added to the DCM solution and the mixture stirred at room temperature for 22 hours. The reaction was filtered and the filtrate reduced to dryness in vacuo. The resulting solid was suspended in chloroform (10 ml), sodium hydroxide solution (2N, 5 ml) added and the mixture stirred for 30 minutes. The organic phase was separated and reduced to dryness under vacuum to give N-cyclopropylmethyl-3-[2-(N,N-dimethylamino)ethoxy]4-iodobenzamide.

LC-MS: MH$^+$ 389, Rt 2.22 min.

Intermediate 2

3-[2-(N,N-Dimethylamino)ethoxyl]-4-iodobenzoic acid

Methyl 3-[2-(N,N-dimethylamino)ethoxy]-4-iodobenzoate (Intermediate 3) (100 mg) was stirred in methanol (2 ml) and sodium hydroxide solution (2N, 2 ml) for 6 hours at room temperature. The methanol was evaporated under vacuum and the remaining solution neutralised with hydrochloric acid (2M). The mixture was extracted with ethyl acetate/chloroform (1:1) and the organic extracts reduced to dryness under vacuum to give 3-[2-(N,N-Dimethylamino)ethoxy]-4-iodobenzoic acid.

LC-MS: [M-H]$^-$ 334, Rt 1.94 min.

Intermediate 3

Methyl 3-[2-(N,N-dimethylamino)ethoxy]-4-iodobenzoate

Sodium hydride (60%, 90.6 mg) was added to methyl 3-hydroxy4-iodobenzoate (525 mg) in DMF (200 ml) and the reaction stirred for 10 minutes at room temperature. 2-Chloro-N,N-dimethylethylamine (244 mg) was added, and the reaction heated at 80° C. for 16 hours. The DMF was evaporated from the cooled reaction in vacuo and the residue partitioned between DCM and water. The organic phase was dried and reduced to dryness under vacuum. The residue was purified on a silica column eluting with a DCM/methanol gradient to give, after evaporation of the solvents, methyl 3-[2-(N,N-dimethylamino)ethoxy]4-iodobenzoate.

Rf (DCM/methanol 95:5) 0.25.

Intermediate 4

Ethyl 4-bromo-3-hydroxybenzoate

4-Bromo-3-hydroxybenzoic acid (100 mg) was dissolved in absolute ethanol (10 ml) and concentrated sulfuric acid (60 µl) added. The reaction was heated at reflux under nitrogen for 22 hours. The solvent was evaporated and the residue was partitioned between ethyl acetate/chloroform (1:1) and water. The organic layers were combined, dried using a hydrophobic filter and the solvent evaporated leaving ethyl 4-bromo-3-hydroxybenzoate as a white solid (109 mg).

LC-MS: Rt 3.12 min.

Intermediate 5

Ethyl 4-bromo-3-{[(methyloxy)methyl]oxy}benzoate

Intermediate 4 (108 mg) was dissolved in DCM (2.5 ml) and dimethoxymethane (2.5 ml) was added. Phosphorous pentoxide (230 mg) was added portion wise over one hour. The mixture was stirred at 20° C. under nitrogen for 16 hours. The reaction mixture was poured onto ice-cooled aqueous sodium hydrogen carbonate (1M, 10 ml) and extracted with diethyl ether (2×10 ml). The organic layers were combined, dried using a hydrophobic filter and the solvent evaporated, to leave ethyl 4-bromo-3-{[(methyloxy)methyl]oxy}benzoate as a yellow liquid (108 mg).

LC-MS: Rt 3.22 min.

Intermediate 6

5'-[(Cyclopropylamino)carbonyl]-3'-fluoro-2'-methyl-2-{[(methyloxy)methyl]oxy}-4-biphenylcarboxylic acid Intermediate 5 (108 mg), {5-[(cyclopropylamino)carbonyl]-3-fluoro-2-methylphenyl}boronic acid (97 mg) and tetrakis(triphenylphosphine) palladium (0) (5 mg) were combined in isopropanol (3.4 ml). Aqueous sodium hydrogen carbonate solution (1M, 1.1 ml) was added and the reaction heated at 90° C. under nitrogen for 18 hours. The solvent was evaporated, ethyl acetate added and the reaction mixture filtered. The solution was taken and the solvent evaporated. The residue was dissolved in methanol (2 ml), aqueous sodium hydroxide (2M, 2 ml) added, and the reaction stirred at 20° C. for three hours. The methanol was removed under vacuum and the remaining aqueous washed with ethyl acetate/chloroform (1:1). The aqueous layer was neutralised using aqueous ammonium chloride (1 M) and extracted using ethyl acetate/chloroform (1:1). The organic extract was washed with water, dried using a hydrophobic filter, and evaporated under vacuum to leave 5'-[(cyclopropylamino)carbonyl]-3'-fluoro-2'-methyl-2-{[(methyloxy)methyl]oxy}-4-biphenylcarboxylic acid as a cream gel (41 mg).

LC-MS: Rt 3.02 min.

Intermediate 7

Methyl 4-bromo-3-(methyloxy)benzoate

4-Bromo-3-hydroxybenzoic add (1 g) was dissolved in methanol (50 ml), concentrated sulphuric acid (330 µl) was added, and the reaction mixture heated at reflux for 16 hours. The reaction mixture was neutralised to pH7 using aqueous sodium hydroxide solution (2M) and the methanol evaporated under vacuum. The mixture was partitioned between water (50 ml) and ethyl acetate/chloroform (1:1, 2×100 ml). The organics were combined, dried using a hydrophobic filter and the solvent evaporated to give a pale brown solid (1 g). This solid was dissolved in acetone (25 ml) and potassium carbonate (680 mg) added. Methyl iodide (366 µl) was added dropwise and the mixture stirred under nitrogen at 20° C. for 22 hours. The reaction was quenched with aqueous sodium hydroxide solution (2M, 1.1 ml) and the solvent evaporated. The resulting solid was partitioned between water (100 ml) and ethyl acetate/chloroform (1:1, 2×100 ml). The organic layers were combined, washed with water (100 ml), dried over a hydrophobic filter, and the solvent evaporated to leave methyl 4-bromo-3-(methyloxy)benzoate as a green-brown solid (980 mg).

LC-MS: Rt 3.13 min.

Intermediate 8

5'-[(Cyclopropylamino)carbonyl]-3'-fluoro-2'-methyl-2-(methyloxy)-4-biphenylcarboxylic acid Intermediate 7 (980 mg), {5-[(cyclopropylamino)carbonyl]-3-fluoro-2-methylphenyl}boronic acid (1.14 g) and tetrakis(triphenylphosphine) palladium (0) (231 mg) were combined in isopropanol (36 ml) and aqueous sodium hydrogen carbonate (1 M, 12 ml) was added. The reaction was stirred under nitrogen for 3 hours at 90° C. The solvent was evaporated under vacuum and the resulting gel dissolved in ethyl acetate/chloroform (1:1, 150 ml) and washed with water (2×100 ml). The organic layer was dried using a hydrophobic filter and evaporated in vacuo. The solid was purified using biotage (40 g, Si), eluting with a gradient of ethyl acetate in cyclohexane (10-20%) to give 5'-[(cyclopropylamino)carbonyl]-3'-fluoro-2'-methyl-2-(methyloxy)-4-biphenylcarboxylic acid (791 mg).

LC-MS: Rt 3.03 min, MH$^+$ 344;

Intermediate 9

Methyl 4-bromo-3-hydroxybenzoate

4-Bromo-3-hydroxybenzoic acid (1 g) was dissolved in methanol (25 ml), concentrated sulphuric acid (165 µl) added and the reaction heated at reflux for 16 hours under nitrogen. The solvent was evaporated and ethyl acetate:chloroform (1:1, 100 ml) added. The solution was neutralised using aqueous sodium hydroxide solution (2M), washed with water (2×100 ml), dried using a hydrophobic filter and the solvent evaporated to leave methyl 4-bromo-3-hydroxybenzoate as a white solid (1.04 g).

LC-MS: Rt 2.92 min.

Intermediate 10

Methyl 4-bromo-3-(propyloxy)benzoate

Intermediate 9 (100 mg) was added to toluene (5 ml) followed by propan-1-ol (49 µl), tributylphosphine (162 µl) and 1,1-azadicarbonyldipiperadine (164 mg) and the mixture stirred under nitrogen for 16 hours at 20° C. The solvent was evaporated and the resulting gel triturated with ether and a white solid removed by filtration. The solvent was evaporated from the ether layer and the residue purified by SPE (5 g, Si), eluting with an ethyl acetate/cyclohexane gradient 1-10%). The solvent was evaporated in vacuo to leave methyl 4-bromo-3-(propyloxy)benzoate as a white solid (75 mg).

LC-MS: Rt 3.58 min.

Intermediate 11

5'-[(Cyclopropylamino)carbonyl]-3'-fluoro-2'-methyl-2-(propyloxy)-4-biphenylcarboxylic acid Intermediate 10 (75 mg), {5-[(cyclopropylamino)carbonyl]-3-fluoro-2-methylphenyl}boronic acid (79 mg) and tetrakis(triphenylphosphine) palladium (0) (10 mg) were combined in isopropanol (2.5 ml). Aqueous sodium hydroxide solution (1M, 0.81 ml) was added and the reaction stirred under nitrogen at 90° C. for 5 hours. The solvent was evaporated in vacuo and the residue partitioned between ethyl acetate/chloroform (1:1, 5 ml) and water (5 ml) and the aqueous extracted with ethyl acetate/chloroform (1:1, 2×5 ml). The organic layers were combined, dried using a hydrophobic filter, and evaporated to leave a yellow gel. The residue was stirred in methanol (1) and aqueous sodium hydroxide solution (2M, 1 ml) under nitrogen at 20° C. for 16 hours. The solvent was evaporated and the residue partitioned between ethyl acetate/chloroform (1:1, 2×10 ml) and water (10 ml). The aqueous layer was acidified to pH1 using concentrated hydrochloric acid, and extracted with ethyl acetate/chloroform (1:1). The organic layers were combined, dried using a hydrophobic filter, and evaporated to leave a white solid. This material was applied to an SPE cartridge (1 g aminopropyl), the cartridge washed with methanol/chloroform (1:9), and the product eluted with acetic acid/rethanollchloroform (1:1:8); to give, after evaporation of the solvents under vacuum, 5'-[(cyclopropylamino)carbonyl]-3'-fluoro-2'-methyl-2-(propyloxy)-4-biphenylcarboxylic acid as a colourless gel (47 mg).

LC-MS: Rt 3.31 min.

Intermediate 12

4-Bromo-N-2,2-dimethylpropyl)-3-hydroxybenzamide

4-Bromo-3-hydroxybenzoic acid (1 g) was heated at 85° C. in thionyl chloride (10 ml) under nitrogen for 4 hours. The excess thionyl chloride was evaporated under vacuum and the reaction mixture dissolved in DCM (10 ml). Sodium carbonate (975 mg) and neopentylamine (800 µl) were added and the reaction stirred at 20° C. for 18 hours. The solvent was evaporated in vacuo and the residue partitioned between ethyl acetate/chloroform (1:1, 100 ml) and water (2×100 ml). The organic layer was dried using a hydrophobic filter and evaporated to leave a 4-bromo-N-(2,2-dimethylpropyl)-3-hydroxybenzamide as white solid (738 mg).

LC-MS: Rt 2.91 min.

Intermediate 13

4-Bromo-3-{[3-(dimethylamino)propyl]oxy}-N-(2,2-dimethylpropyl)benzamide

Intermediate 12 (150 mg) was dissolved In toluene (8 ml), 3-dimethylamino-1-propanol (92 µl), tributylphosphine (194 µl) and 1,1-azadicarbonyldipiperadine (198 mg) were added and the mixture stirred under nitrogen at 20° C. for 17 hours. The solvent was evaporated in vacuo and the residue triturated with ether. A white solid was removed by filtration and the filtrate was reduced to dryness. The residue was purified by SPE (10 g, Si), eluting with an ethyl acetatelcyclohexane gradient (50-100%) and then with methanol/ethyl acetate (1:9). Solvent was evaporated in vacuo from the product fractions to leave 4-bromo-3{[3-(dimethylamino)propyl]oxy}-N-(2,2-dimethylpropyl)benzamide as a yellow gel (108 mg).

LC-MS: Rt 2.26 min.

Intermediate 14

4-Bromo-3-[(3-bromopropyl)oxyl]-N-(2,2-dimethylpropyl)benzamide

Intermediate 12 (250 mg) was suspended in toluene (20 ml). 3-Bromo-propan-1-ol (118 µl), tributylphosphine (326 µl) and 1,1-azadicarbonyidipiperadine (331 mg) were added and the reactior, mixture stirred at 20° C. under nitrogen for 18 hours. The solvent was evaporated under vacuum and residue triturated with ether. A white solid was removed by filtration, the solvent evaporated from the filtrate and the residue purified by SPE (50 g, Si), eluting with a ethyl acetate/cyclohexane gradient (0-100%). The solvent was evaporated from the product fractions to give 4-bromo-3-[(3-bromopropyl)oxy]-N-(2,2-dimethylpropyl)benzamide as a white solid (274 mg).

LC-MS: Rt 3.59 min.

Intermediate 15

2'-[(3-Bromopropyl)oxy]-$N^3$-cyclopropyl-$N^{4'}$-(2,2-dimethylpropyl)-6-methyl-3,4'-biphenyldicarboxamide Intermediate 14 (270 mg), N-cyclopropyl-4-methyl-3-(4,4,5,5-tetramethyl-1,3,2-dioxaborolanyl)benzamide (239 mg) and tetrakis(triphenylphosphine) palladium (0) (35 mg) were combined in isopropanol (6 ml) and aqueous sodium hydrogen carbonate solution (1M, 2 ml) added. The reaction was stirred under nitrogen at 90° C. for 5 hours. The solvent was evaporated in vacuo and residue partitioned between water (50 ml) and ethyl acetate/chloroforrm (1:1, 50 ml). The organic layer was dried using a hydrophobic filter and solvent evaporated under vacuum to leave a brown solid. The residue was purified by SPE (70 g, Si) eluting with an ethyl acetate/cyclohexane gradient (0-100%). The solvent was evaporated from the product fractions to give 2'-[(3-bromopropyl)oxy]-$N^3$-cyclopropyl-$N^{4'}$-(2,2-dimethylpropyl)-6-methyl-3,4'-biphenylidicarboxamide as a yellow gel (205 mg).

LC-MS: Rt 3.43 min, MH$^+$ 501/503.

Intermediate 16

Methyl 4-bromo-3-({2-[(methylsulfonyl)amino]ethyl}oxy)benzoate

Methyl 4-bromo-3-hydroxybenzoate (231 mg) and N-(2-iodoethyl)methanesulfonamide (274 mg) were dissolved in DMF (10 ml), sodium hydride (64 mg, 60% dispersion in mineral oil) was added and the reaction heated at 80° C. for 20 hours. The solvent was evaporated in vacuo and the residue purified by SPE (5 g, Si), eluting with a chloroform/methanol gradient (0-5% methanol). The solvents were evaporated under vacuum from the product fractions to give methyl 4-bromo-3-({2-[(methylsulfonyl)amino]ethyl}oxy)benzoate as a colourless gel (83 mg).

LC-MS: Rt 2.80 min.

Intermediate 17

5'-[(Cyclopropylamino)carbonyl]-3'-fluoro-2'-methyl-2-({2-[(methylsulfonyl)amino]ethyl}oxy)-4-biphenylcarboxylic acid Intermediate 16 (80 mg), {5-[(cyclopropylamino)carbonyl]-3-fluoro-2-methylphenyl}boronic acid (65 mg) and tetrakis(triphenylphosphine) palladium (0) (10 mg) were combined in isopropanol (2 ml), aqueous sodium hydrogen carbonate solution (1 M, 690 µl) added and the reaction heated under nitrogen for 18 hours at 90° C. The solvent was evaporated in vacuo and the residue partitioned between ethyl acetate chloroform (1:1, 2×10 ml) and water. The organic layers were combined, dried using a hydrophobic filter and the solvent evaporated under vacuum to give a white foam. The foam was dissolved in methanol (7.5 ml), aqueous sodium hydroxide solution (2M, 7.5 ml) added and the reaction stirred for 3 hours at 20° C. under nitrogen. The solvents were evaporated under vacuum and the residue partitioned between ethyl acetate/chloroform (1:1, 30 ml) and water (2×30 ml). The aqueous layer was acidified to pH1 using concentrated hydrochloric acid and extracted with ethyl acetate/chloroform (1:1, 3×30 ml). The organic phases were combined, dried using a hydrophobic filter and evaporated to give 5'-[(cyclopropylamino)carbonyl]-3'-fluro-2'-methyl-2-

({2-[(methylsulfonyl)amino]ethyl}oxy)-4-biphenylcarboxylic acid as a colourless gel (79 mg).
LC-MS: Rt 2.83 min.

Intermediate 18

Methyl 4-bromo-3-{[2-(4-morpholinyl)ethyl]oxy}benzoate

Methyl 4-bromo-3-hydroxybenzoate (143 mg) and 4-(2-iodoethyl)morpholine.HCl (189 mg) were combined in DMF (10 ml). Sodium hydride (55 mg, 60% dispersion in mineral oil) was added and the reaction heated at 80° C. under nitrogen for 5 hours. The reaction was quenched with water (10 ml) and the solvent evaporated under vacuum. Ethyl acetate/chloroform (1:1, 30 ml) and water (30 ml) were added to the residue resulting in precipitation of a solid, which was filtered off and washed with ether. The solid was partitioned between ethyl acetate/chloroform (1:1, 2×50 ml) and aqueous sodium hydrogen carbonate solution (1 M, 50 ml). The organic layers were combined, dried over a hydrophobic filter and evaporated to give methyl 4-bromo-3-{[2-(4-morpholinyl)ethyl]oxy}benzoate as a yellow gel (103 mg).
LC-MS: Rt 2.11 min.

Intermediate 19

5'-[(Cyclopropylamino)carbonyl]-3'-fluoro-2'-methyl-2-{[2-(4-morpholinyl)ethyl]oxy}-4-biphenylcarboxylic acid Intermediate 18 (100 mg), {5-[(cyclopropylamino)carbonyl]-3-fluoro-2-methylphenyl}boronic acid (83 mg) and tetrakis(triphenylphosphine) palladium (0) (15 mg) were combined in isopropanol (2.6 ml). Aqueous sodium hydrogen carbonate solution (1 M, 0.87 ml) was added and the reaction heated under nitrogen for 17 hours at 90° C. The solvent was evaporated and residue partitioned between water (15 ml) and ethyl acetate/chloroform (1:1, 15 ml). The aqueous layer was acidified to pH7 using hydrochloric acid (2M) and extracted with ethyl acetate/chloroform (1:1, 2×15 ml). The organic layers were combined, dried using a hydrophobic filter, and evaporated in vacuo. The residue was purified by SPE (2 g Si), eluting with a methanol/chloroform gradient (0-10%). The solvent was evaporated from the product fractions to give 5'-[(cyclopropylamino)carbonyl]-3'-fluoro-2'-methyl-2-{[2-(4-morpholinyl)ethyl]oxy}-4-biphenylcarboxylic acid as a white solid (25 mg).
LC-MS: Rt 2.28 min.

Intermediate 20

Methyl 4-bromo-3-{[2-(4-morpholinyl)-2oxoethyl]oxy}benzoate

Methyl 4-bromo-3-hydroxybenzoate (71 mg) and 4-(bromoacetyl)morpholine (71 mg) were combined in DMF (5 ml). Sodium hydride (14 mg, 60% dispersion in mineral oil) was added and the reaction heated at 80° C. under nitrogen for 16 hours. The reaction was quenched with water (2 ml) and solvent the evaporated in vacuo. The residue was partitioned between water (10 ml) and ethyl acetate/chloroform (1:1, 2×10 ml). The organic layers were combined, dried using a hydrophobic filter and evaporated under vacuum. The residue was partially purified by SPE (2 g, Si), eluting with a methanol/chloroform gradient (0.5% to 5%), and the product fractions further purified by mdap, to give methyl 4bromo-3-{[2-(4-morpholinyl)-2-oxoethyl]oxy}benzoate as a white solid (16 mg).
LC-MS: Rt 2.72 min.

Intermediate 21

5'-[(Cyclopropylamino)carbonyl]-3'-fluoro-2'-methyl-2{[2-(4 morpholinyl)-2-oxoethyl]oxy}-4-biphenylcarboxylic acid Intermediate 20 (16 mg), {5-[(cyclopropylamino)carbonyl]-3-fluoro-2-methylphenyl}boronic acid (13 mg) and tetrakis(triphenylphosphine) palladium (0) (3 mg) were combined in Isopropanol (0.4 ml). Aqueous sodium hydrogen carbonate (1M, 135 µl) was added and the reaction heated under nitrogen at 90° C. for 6 hours. The solvent was evaporated and residue partitioned between ethyl acetate/chloroform (1:1) and water. The aqueous layer was acidified to pH1 using 2M aqueous hydrochloric acid and extracted with ethyl acetate/chloroform (1:1). The organic layer was dried using a hydrophobic filter and evaporated in vacuo to give 5'-[(cyclopropylamino)carbonyl]-3'-fluoro-2'-methyl-2-{[2-(4-morpholinyl)-2-oxoethyl]oxy}-4-biphenylcarboxylic acid as a colourless gel (11 mg).
LC-MS: Rt 2.75 min.

Intermediate 22

Methyl 4-[(2-bromo-5-{[(2,2-dimethylpropyl)amino]carbonyl}phenyl)oxy]butanoate

Intermediate 12 (200 mg) and methyl 4-iodobutyrate (157 µl) were combined in DMF (10 ml). Sodium hydride (37 mg, 60% dispersion in mineral oil) was added and the reaction heated at 80° C. under nitrogen for 6 hours. The reaction was quenched with water (5 ml) and the solvent evaporated in vacuo. The residue was partitioned between ethyl acetate/chloroform (1:1) and water. The organics were dried using a hydrophobic filter and the solvent evaporated to give methyl 4-[(2-bromo-5-{[(2,2-dimethylpropyl)amino]carbonyl}phenyl)oxy]butanoate as a brown gum (368 mg).
LC-MS: Rt 3.33 min.

Intermediate 23

Ethyl 3-{[4-(acetyloxy)butyl]oxy}-4-bromobenzoate

Ethyl 4-bromo-3-hydroxybenzoate (200 mg) was dissolved in DMF (10 ml) and 4-iodo-butyl acetate (195 µl) and sodium hydride (56 mg, 60% dispersion in mineral oil) were added and the reaction stirred at 80° C. under nitrogen for 3 hours. The reaction was quenched with water (5 ml) and the solvents evaporated under vacuum. The residue was partitioned between ethyl acetate/chloroform (1:1) and water. The organic phase was dried using a hydrophobic filter and the solvent evaporated in vacuo to give ethyl 3-{[4-(acetyloxy)butyl]oxy}-4-bromobenzoate as a yellow gel (318 mg).
LC-MS: Rt 3.47 min.

Intermediate 24

5'-[(Cyclopropylamino)carbonyl]-3'-fluoro-2-[(4-hydroxybutyl)oxy]-2'-methyl-4-biphenylcarboxylic acid Intermediate 23 (318 mg), {5-[(cyclopropylamino)carbonyl]-3-fluoro-2-methylphenyl}boronic acid (252 mg) and tetrakis(triphenylphosphine) palladium (0) (45 mg) were combined in isopropanol and aqueous sodium hydrogen carbonate solution (1M, 2.7 ml) added. The reaction was stirred under nitrogen at 90° C. for 6 hours. The solvent was evaporated in vacuo and the residue partitioned between ethyl acetate/chloroform (1:1) and water. The organic phase was dried using a hydrophobic filter, the solvent evaporated under vacuum. The residue was dissolved in methanol (10 ml), aqueous sodium hydroxide solution (2M, 10 ml) added and the reaction stirred at 20° C. for 18 hours. The solvents were evaporated and residue partitioned between ethyl acetate/chloroform (1:1) and water. The aqueous layer was acidified to pH1 using concentrated hydrochloric acid and extracted with ethyl acetate/chloroform (1:1). The organic phase was dried using a hydrophobic filter and evaporated, and the residue purified using SPE (5 g, Si), eluting with a methanol/chloroform gradient (1-10%). The solvents were evaporated from the product fraction in vacuo to give 5'-[(cyclopropylamino)carbonyl]-3'-fluoro-2-[(4-hydroxybutyl)oxy]-2'-methyl-4-biphenylcarboxylic acid as a cream solid (140 mg).

LC-MS: Rt 2.85 min.

Intermediate 25

1,1-Dimethylethyl 2-{4-[(5'-[(cyclopropylamino)carbonyl]-4-{[(2,2-dimethylpropyl)amino]carbonyl}-3'-fluoro-2'-methyl-2-biphenylyl)oxy]butanoyl}hydrazinecarboxylate Example 33 (45 mg), HATU (33 mg) and diisopropylethylamine (49 μl) were combined in DMF (5 ml) and the reaction stood for 10 minutes. t-Butyl carbazate (25 mg) was added and the reaction stirred at 20° C. for 5 hours under nitrogen. The solvent was evaporated under vacuum and the residue purified by SPE (2 g, aminopropyl), eluting with 10% methanol in chloroform. The product was further purified was by SPE (2 g, Si), elutng with a ethyl acetate/cyclohexane gradient (10-50%). Evaporation of the solvents gave 1,1-dimethylethyl 2-{4-[(5'-[(cyclopropylamino)carbonyl]-4-{[(2,2-dimethylpropyl)amino]carbonyl}-3'-fluoro-2'-methyl-2-biphenylyl)oxy]butanoyl}hydrazinecarboxylate as a white foam (41 mg).

LC-MS: Rt 3.28 min, MH+ 599.

Intermediate 26

$N^3$-Cyclopropyl-$N^{4'}$-(2,2-dimethylpropyl)-5-fluoro-2'-[(4-hydrazino-4-oxobutyl) oxy]-6-methyl-3,4'-biphenyldicarboxamide Intermediate 25 (40 mg) was dissolved in hydrochloric acid in 1,4-dioxane (4M, 2.5 ml) and stirred at 20° C. under nitrogen for 4 hours. The solvent was evaporated and the residue was partitioned between ethyl acetatelchloroform (1:1) and water. The organic phase was dried using a hydrophobic filter and evaporated to give $N^3$-cyclopropyl-$N^{4'}$-(2,2-dimethylpropyl)-5-fluoro-2'-[(4-hydrazino-4-oxobutyl) oxy]-6-methyl-3,4'-biphenylidicarboxamide as a white solid (24 mg).

LC-MS: 2.94 min, MH+ 499.

Intermediate 27

4-Bromo-3-{[(2,2-dimethyl-1,3-dioxolan-4-yl)methyl]oxy}-N-(2,2-dimethylpropyl)benzamide Intermediate 12 (46 mg), 4(bromomethyl)-2,2-dimethyl-1,3-dioxolane (62 mg) were combined in DMF (0.5 mg ), sodium hydride (12 mg, 60% dispersion in mineral oil) was added and the reaction heated under nitrogen at 80° C. for 40 hours. The reaction was quenched with water (10 ml) and extracted with ethyl acetate/chloroform (1:1, 2×10 ml). The organic phases were combined, dried using a hydrophobic filter and the solvents evaporated under vacuum. The residue was dissolved in 2,2-dimethyloxypropane (2 ml), pyridinium p-toluene sulfonate (5 mg) added and the reaction and stirred for 8 days. The solvent was evaporated in vacuo and the residue partitioned between water (10 ml) and ethyl acetate/chloroform (1:1, 10 ml). The organic phase was dried using a hydrophobic filter and solvent evaporated to give 4-bromo-3-{[(2,2-dimethyl-1,3-dioxolan-4-yl)-methyl]oxy}-N-(2,2-dimethylpropyl)benzamide as a yellow gel (43 mg).

LC-MS: Rt 3.29 min.

Intermediate 28

4-Bromo-3-formylbenzoic acid

4-Bromo-3-(dibromomethyl)benzoic acid (3.7 g) was added to a solution of aqueous sodium carbonate (16 g in 100 ml) and the mixture heated at 70° C. for 12 hrs. The pH of the cooled reaction was adjusted to pH5 using hydrochloric acid (2N) and the mixture extracted with ethyl acetate, to give, after evaporation of the solvent in vacuo, 4-bromo-3-formylbenzoic acid.

NMR: δH $D_6$-DMSO 13.53, (1H, b), 10.23, (1H, s), 8.31, (1H, d), 8.08, (1H, dd), 7.94, (1H, d).

Intermediate 29

4-Bromo-3-formylbenzoyl chloride

Intermediate 28 (886 mg) and thionyl chloride (4 ml) were heated at reflux under nitrogen for 1 hr. The excess thionyl chloride was evaporated in vacuo and the residue azeotroped with toluene (5 ml×3) to give 4bromo-3-formylbenzoyl chloride as a yellow/white solid.

NMR: δH $CDCl_3$ 10.41, (1H, s), 8.64, (1H, d),-8.15, (1H, dd), 7.86, (1H, d).

Intermediate 30

4-Bromo-N-(2,2-dimethylpropyl)-3-{(E)-[(2,2-dimethylpropyl)imino]methyl}benzamide Triethylamine (1.55 ml) and neopentylamine (1.09 ml) were added to a solution of Intermediate 29 (914 mg) in DCM (16 ml). The reaction was then cooled in an ice-bath and stirred for 1 hr. The reaction mixture was partitioned between aqueous sodium carbonate and ethyl acetate. The aqueous phase was extracted with ethyl acetate and the combined organic phases reduced to dryness under vacuum to give 4-bromo-N-(2,2-dimethylpropyl)-3-{(E)-[(2,2-dimethylpropyl)imino]methyl}benzamide.

LC-MS: Rt 3.07 min.

Intermediate 31

4-Bromo-N-(2,2-dimethylpropyl)-3-{[(2,2-dimethylpropyl)amino]methyl}benzamide

Sodium triacetoxyborohydride (318 mg) was added dropwise to a solution of Intermediate 30 (110 mg) in anhydrous THF (2 ml) and the reaction stirred under nitrogen for 2 hrs.

Methanol was added to the reaction, the mixture stirred and the solvents evaporated in vacuo. The resulting solid was partitioned between water and ethyl acetate, the organic phase was with water (×2) and reduced to dryness under vacuum. The residue was dissolved in the minimum volume of DCM and applied to an SPE (silica, 2 g) and eluted with a methanol/DCM gradient (1-2% methanol), which gave after evaporation of the solvents in vacuo, 4-bromo-N-(2,2-dimethylpropyl)-3-{[(2,2-dimethylpropyl)amino]methyl}benzamide as a white solid.

LC-MS: Rt 2.38 min, MH+ 369/371.

Intermediate 32

$N^3$-Cyclopropyl-$N^{4'}$-(2,2-dimethylpropyl)-5-fluoro-2'-formyl-6-methyl-3,4'-biphenyldicarboxamide Intermediate 30 (36.7 mg), {5-[(cyclopropylamino)carbonyl]-3-fluoro-2-methylphenyl}boronic acid (23.7 mg), tetrakis(triphenylphosphine)palladium (1 mg) and sodium hydrogencarbonate (1M, 0.3 ml) in isopropanol (0.6 ml) were heated by microwave in a sealed vessel at 150° C. for 15 mins. The cooled reaction was partitioned between water and ethyl acetate and the organic phase reduced to dryness. The residue was purified by preparative HPLC (mdap) to give, after evaporation of the solvents, $N^3$-cyclopropyl-$N^{4'}$-(2,2-dimethylpropyl)-5-fluoro-2'-formyl-6-methyl-3,4'-biphenylidicarboxamide.

LC-MS: Rt 3.26 min, MH+ 411.

Intermediate 33

4-Bromo-3-nitrobenzoyl chloride

4-Bromo-3-nitrobenzoic acid (500 mg) in thionyl chloride (3 ml) was heated at 110° C. for 2 hrs. The excess thionyl chloride was evaporated in vacuo to give 4-bromo-3-nitrobenzoyl chloride as a yellow solid (502 mg).

NMR: δH CDCl₃ 8.56, (1H, d), 8.15, (1H, dd), 7.96, (1H, d).

Intermediate 34

4-Bromo-N-(2,2-dimethylpropyl)-3-nitrobenzamide

Neopentylamine (265 µl) was added to a mixture of Intermediate 33 (500 mg) and sodium carbonate (240 mg) in DCM (5 ml) and the reaction stirred for 5 hours at room temperature. The reaction was filtered and the filtrate passed through an SPE (SCX). The eluent was reduced to dryness under vacuum to give 4-bromo-N-(2,2-dimethylpropyl)-3-nitrobenzamide as a yellow solid (615 mg).

LC-MS: Rt 3.19 min.

Intermediate 35

$N^3$-Cyclopropyl-$N^{4'}$-(2,2-dimethylpropyl)-6-methyl-2'-nitro-3,4'-biphenyldicarboxamide Intermediate 34 (350 mg), N-cyclopropyl-4-methyl-3-(4,4,5,5-tetramethyl-1,3,2-dioxaborolan-2-yl)benzamide (334 mg), tetrakis(triphenylphosphine)palladium (26 mg) and sodium hydrogen carbonate (1M, 4.4 ml) were heated in isopropanol (30 ml) at 85° C. for 18 hours. The reaction was reduced to dryness under vacuum and the residue partitioned between chloroform/ethyl acetate (1:1) and water. The organic phase was washed with water (2×50 ml), dried (hydrophobic frit) and the solvents evaporated under vacuum. The residue was purified on a silica gel column eluting with an ethyl acetate / cyclohexane gradient (0-100% ethyl acetate), which gave after evaporation of the solvents in vacuo $N^3$-cyclopropyl-$N^{4'}$-(2,2-dimethylpropyl)-6-methyl-2'-nitro-3,4'-biphenyldicarboxamide (360 mg) as a yellow solid.

LC-MS: MH+ 310, Rt 3.15 min.

Example 1

$N^3$-Cyclopropyl-$N^{4'}$-(cyclopropylmethyl)-2'-[2-(dimethylamino)ethoxy]-5-fluoro-6-methyl-1,1'-biphenyl-3,4'-dicarboxamide

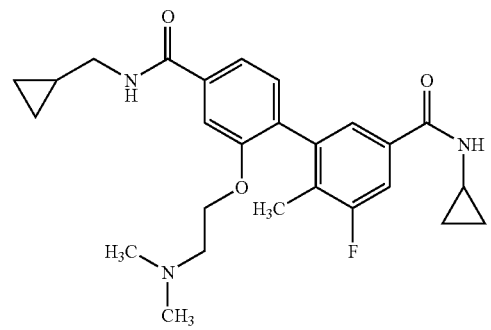

N-Cyclopropylmethyl-3-[2-(dimethylamino)ethoxy]4-iodobenzamide (Intermediate 1) (42 mg), N-cyclopropyl-5-fluoro-4-methyl-3-(4,4,5,5-tetramethyl-[1,3,2]dioxaborolan-2-yl)-benzamide (38 mg), tetrakis(triphenylphosphine) palladium (2 mg) and aqueous sodiumhydrogen carbonate (1M, 0.3 ml) were reacted in propan-2-ol (2 ml) at 9° C. for 20 hours. The solvent was evaporated under vacuum and the residue purified by bond-elut (silica, 10 g) eluting with a methanol/chloroform gradient (1-10% methanol) to give, after evaporation of the solvents, $N^3$-cyclopropyl-$N^{4'}$-(cyclopropylmethyl)-2'-[2-(dimethylamino)ethoxy]-5-fluoro-6-methyl-1,1 '-biphenyl-3,4'-dicarboxamide.

NMR: □H CDCl3 7.50-7.48, (2H, m), 7.35-7.31, (2H, m), 7.19, (1H, d), 6.57, (1H, bs), 6.36, (1H, bt), 4.12, (2H, q), 3.33, (2H, m), 2.88, (1H, m), 2.60, (2H, m), 2.19, (6H, s), 2.07, (3H, d), 1.09, (1H, m), 0.87, (2H, m), 0.62-0.57, (4H, m), 0.31, (2H, m). LCMS: MH+ 454,retention time 2.35 minutes.

General Method A (HATU Amide Coupling)

The bi-aryl acid (1 eq) and HATU (1.12 eq) were combined in DMF. Diisopropylethylamine (3eq) was added and the reaction mixture stood for 10 minutes. The amine (1.1 eq) was added and the reaction stirred for 16 hours under nitrogen at 20° C. The DMF was removed under vacuum and the reaction mixture purified by aminopropyl SPE, eluting with methanol/chloroform (1:9). The product containing fractions were combined and evaporated under vacuum.

Example 2

N³-Cyclopropyl-5-fluoro-2'-hydroxy-6-methyl-N⁴'-[(4-methylphenyl)methyl]-3,4'-biphenyldicarboxamide

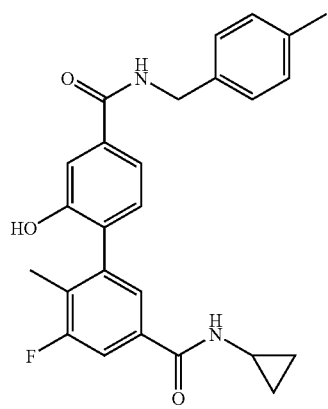

Intermediate 6 (38 mg) was reacted with 4-methylbenzylamine according to General Method A. The resulting yellow gel was stirred in hydrochloric acid in 1,4-dioxane (4M, 4 ml) at 20° C. for 17 hours. The solvent was evaporated to leave a white solid, which was purified by mdap, to give N³-cyclopropyl-5-fluoro-2'-hydroxy-6-methyl-N⁴'-[(4-methylphenylmethyl]-3,4'-biphenylidicarboxamide as a white solid (19 mg).

LC-MS: Rt 3.16 min, MH⁺ 433.

Example 3

N³-Cyclopropyl-N⁴'-(2,2-dimethylpropyl)-5-fluoro-6-methyl-2'-{[(methyloxy)methyl]oxy}-3,4'-biphenyldicarboxamide

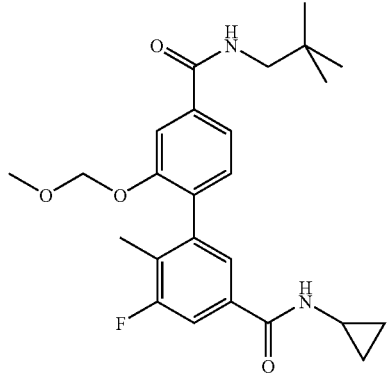

Intermediate 6 (48 mg) was reacted with neopentylamine according to General Method A. Further purification was done using mdap, to give N³-cyclopropyl-N⁴'-(2,2dimethylpropyl)-5-fluoro-6-methyl-2'-{[(methyloxy)methyl]oxy}-3,4'-biphenyldicarboxamide.

LC-MS: Rt 3.22 min, MH⁺ 443.

Example 4

N³-Cyclopropyl-5-fluoro-6-methyl-2'-{[(methyloxy)methyl]oxy}-N⁴'-(2-methylpropyl)-3,4'-biphenyldicarboxamide

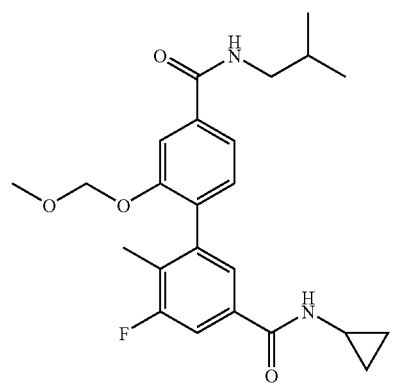

Intermediate 6 (48 mg) was reacted with isobutylamine according to General Method A. Further purification was done using mdap, to give N³-cyclopropyl-5fluoro-6-methyl-2'-{[(methyloxy)methyl]oxy}-N⁴'-(2-methylpropyl)-3,4'-biphenylidicarboxamide.

LC-MS: Rt 3.16 min, MH⁺ 429.

Example 5

N³-Cyclopropyl-N⁴'-(cyclopropylmethyl)-5-fluoro-6-methyl-2'-{[(methyloxy)methyl]oxy}-3,4'-biphenyldicarboxamide

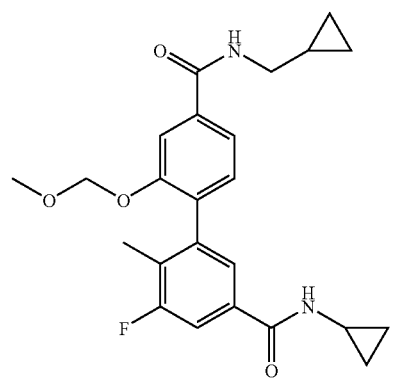

Intermediate 6 (48 mg) was reacted with cyclopropanemethylamine according to General Method A. Further purification was done using mdap, to give $N^3$-cyclopropyl-$N^{4'}$-(cyclopropylmethyl)-5fluoro-6-methyl-2'-{[(methyloxy)methyl]oxy}-3,4'-biphenylidicarboxamide.

LC-MS: Rt 3.08 min, MH$^+$ 427.

Example 6

$N^3$-Cyclopropyl-5-fluoro-6-methyl-2'-{[(methyloxy)methyl]oxy}-$N^{4'}$-{[4-(methyloxy)phenyl]methyl}-3,4-biphenyldicarboxamide

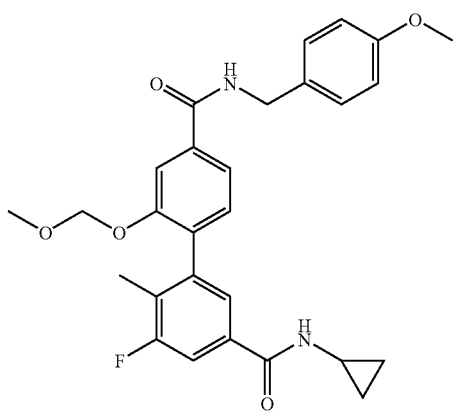

Intermediate 6 (48 mg) was reacted with para-methoxybenzylamine according to General Method A. Further purification was done using mdap, to give $N^3$-cyclopropyl-5-fluoro-6-methyl-2'-{[(methyloxy)methyl]oxy}-$N^{4'}$-{[4-(methyloxy)phenyl]methyl}-3,4'-biphenylidicarboxamide.

LC-MS: Rt 3.23 min, MH$^+$ 493.

Example 7: $N^3$-Cyclopropyl-5-fluoro-6-methyl-2'-{[(methyloxy)methyl]oxyy}-$N^{4'}$-[(1R)-1,2,2-trimethylpropyl]-3,4'-biphenyldicarboxamide

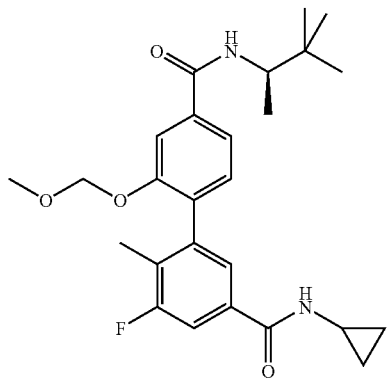

Intermediate 6 (48 mg) was reacted with (R)-3,3-dimethyl-2-butylamine according to General Method A. Further purificaton was done using mdap, to give $N^3$-cyclopropyl-5-fluoro-6-methyl-2'-{[(methyloxy)methyl]oxy}-$N^{4'}$-[(1R)-1,2,2-trimethylpropyl]-3,4'-biphenylidicarboxamide.

LC-MS: Rt 3.35 min, MH$^+$ 457.

Example 8

$N^3$-Cyclopropyl-$N^{4'}$-[(1R)-1,2-dimethylpropyl]-5-fluoro-6-methyl-2'-{[(methyloxy)methyl]oxy}-3,4'-biphenyldicarboxamide

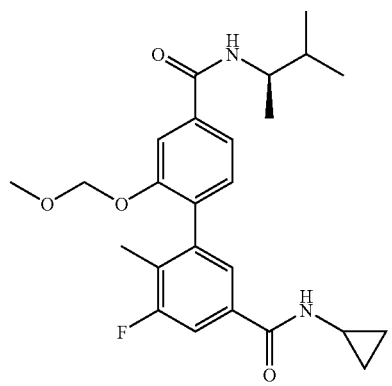

Intermediate 6 (48 mg) was reacted with (R)-(−)-3-methyl-2-butylamine according to General Method A. Further purification was done using mdap, to give $N^3$-cyclopropyl-$N^{4'}$-[(1R)-1,2-dimethylpropyl]-5-fluoro-6-methyl-2'-{[(methyloxy)methyl]oxy}-3,4'-biphenylidicarboxamide.

LC-MS: Rt 3.25 min, MH$^+$ 443.

Example 9

$N^3$-Cyclopropyl-$N^{4'}$-(2,2-dimethylpropyl)-5-fluoro-2'-hydroxy-6-methyl-3,4'-biphenyldicarboxamide

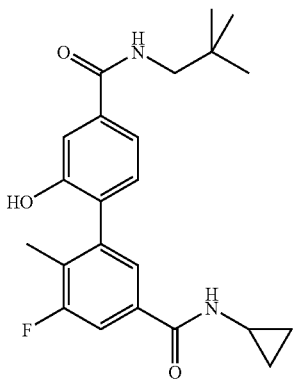

Example 3 was stirred in hydrochloric acid in 1,4-dioxane (4M, 1 ml) for 18 hours at 20° C. The solvent was evaporated and the sample purified by mdap to give $N^3$-cyclopropyl-$N^{4'}$-(2,2-dimethylpropyl)-5-fluoro-2'-hydroxy-6-methyl-3,4'-biphenyldicarboxamide.

LC-MS: Rt 3.11 min, MH$^+$ 398.

Example 10

N³-Cyclopropyl-5-fluoro-2'-hydroxy-6-methyl-N⁴'-(2-methylpropyl)-3,4'-biphenyldicarboxamide

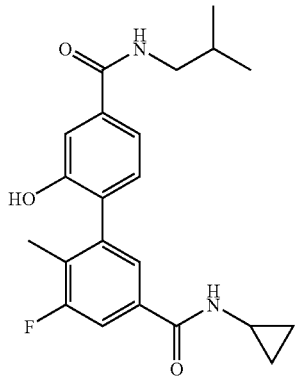

Example 4 was stirred in hydrochloric acid in 1,4-dioxane (4M, 1 ml) for 18 hours at 20° C. The solvent was evaporated and the sample purified by SPE (1 g, Si), eluting with one column volume of chloroform, diethyl ether, ethyl acetate and acetone. The ethyl acetate layer was evaporated to give N³-cyclopropyl-5-fluoro-2'-hydroxy-6-methyl-N⁴'-(2-methylpropyl)-3,4'-biphenyldicarboxamide.

LC-MS: Rt 2.99 min, MH⁺ 385.

Example 11

N³-Cyclopropyl-N⁴'-(cyclopropylmethyl)-5-fluoro-2'-hydroxy-6-methyl-3,4'-biphenyldicarboxamide

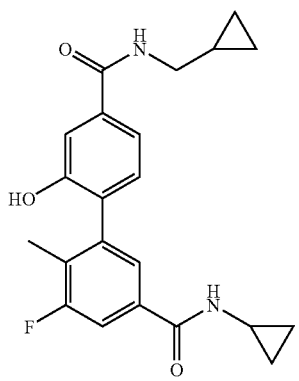

Example 5 was stirred in hydrochloric acid in 1,4-dioxane (4M, 1 ml) for 18 hours at 20° C. The solvent was evaporated and the sample purified by SPE (1 g, Si), eluting with one column volume of chloroform, diethyl ether, ethyl acetate and acetone. The ethyl acetate layer was evaporated to give N³-cyclopropyl-N⁴'-(cyclopropylmethyl)-5-fluoro-2'-hydroxy-6-methyl-3,4'-biphenyldicarboxamide.

LC-MS: Rt 2.90 min, MH⁺ 382.

Example 12

N³-Cyclopropyl-5-fluoro-2'-hydroxy-6-methyl-N⁴'-{[4-(methyloxy)phenyl]methyl}-3,4'-biphenyldicarboxamide

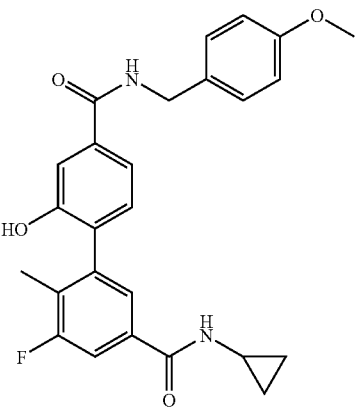

Example 6 was stirred in hydrochloric acid in 1,4-dioxane (4M, 1 ml) for 18 hours at 20° C. The solvent was evaporated and the sample purified by SPE (1 g, Si), eluting with one column volume of chloroform, diethyl ether, ethyl acetate and acetone. The ethyl acetate and ether layers were evaporated to give N³-cyclopropyl-5-fluoro-2'-hydroxy-6-methyl-N⁴'-{[4-(methyloxy)phenyl]methyl}-3,4'-biphenyldicarboxamide.

LC-MS: 3.08 min, MH⁺ 449.

Example 13

N³-Cyclopropyl-5-fluoro-2'-hydroxy-6-methyl-N⁴'-[(1R)-1,2,2-trimethylpropyl]-3,4'-biphenyldicarboxamide

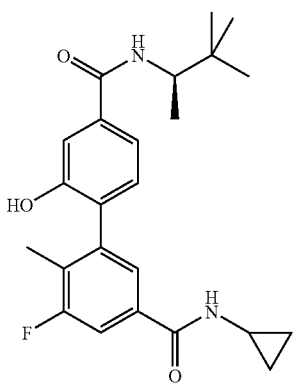

Example 7 was stirred in hydrochloric acid in 1,4-dioxane (4M, 1 ml) for 18 hours at 20° C. The solvent was evaporated and the sample purified by mdap to give N³-cyclopropyl-5-fluoro-2'-hydroxy-6-methyl-N⁴'-[(1R)-1,2,2-trimethylpropyl]-3,4'-biphenylidicarboxamide.

LC-MS: 3.19 min, MH⁺ 413.

Example 14

N³-Cyclopropyl-N⁴'-[(1R)-1,2-dimethylpropyl]-5-fluoro-2'-hydroxy-6-methyl-3,4'-biphenyldicarboxamide

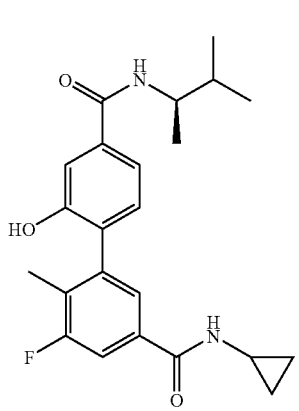

Example 8 was stirred in hydrochloric acid in 1,4-dioxane (4M, 1 ml) for 18 hours at 20° C. The solvent was evaporated and the sample purified by SPE (1 g, Si), eluting with one column volume of chloroform, diethyl ether, ethyl acetate and acetone. The ethyl acetate layer was evaporated to give to give N³-cyclopropyl-N⁴'-[(1R)-1,2-dimethylpropyl]-5-fluoro-2'-hydroxy-6-methyl-3,4'-biphenylidicarboxamide.

LC-MS: Rt 3.08 min, MH⁺ 398.

Example 15

N³-Cyclopropyl-N⁴'-(2,2-dimethylpropyl)-5-fluoro-6-methyl-2'-(methyloxy)-3,4'-biphenyldicarboxamide

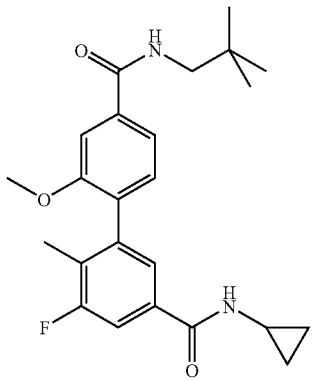

Intermediate 8 was reacted with neopentylamine according to General Method A. The residue was further purified using SPE (500 mg, SCX), eluting with chloroform. The solvent was evaporated to leave a colourless gel, which was triturated with ether to give N³-cyclopropyl-N⁴'-(2,2-dimethylpropyl)-5-fluoro-6-methyl-2'-(methyloxy)-3,4'-biphenylidicarboxamide as a white solid (32.2 mg).

LC-MS: Rt 3.34 min, MH⁺ 413.

Example 16

N³-Cyclopropyl-5-fluoro-6-methyl-2'-(methyloxy)-N⁴'-(2-methylpropyl)-3,4'-biphenyldicarboxamide

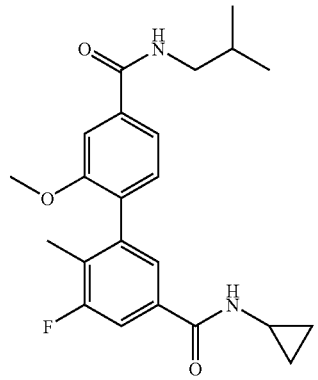

Intermediate 8 was reacted with isobutylamine according to General Method A. The residue was further purified using SPE (500 mg, SCX), eluting with chloroform. The solvent was evaporated to leave a colourless gel, which was triturated with ether to give N³-cyclopropyl-5-fluoro-6-methyl-2'-(methyloxy)-N⁴'-(2-methylpropyl-3,4'-biphenyldicarboxamide as a white solid (33.1 mg).

LC-MS: Rt 3.22 min, MH⁺ 399.

Example 17

N³-Cyclopropyl-N⁴'-(cyclopropylmethyl)-5-fluoro-6-methyl-2'-(methyloxy)-3,4'-biphenyldicarboxamide

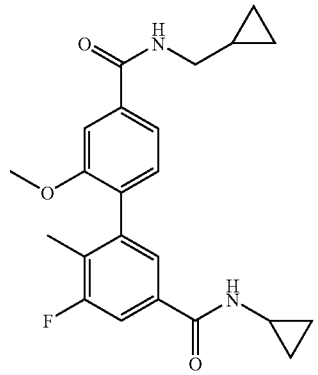

Intermediate 8 was reacted with cyclopropylmethylamine according to General Method A. The residue was further purified using SPE (500 mg, SCX), eluting with chloroform. The solvent was evaporated to leave a colourless gel, which was triturated with ether to give N³-cyclopropyl-N⁴'-(cyclopropylmethyl)-5-fluoro-6-methyl-2'-(methyloxy)-3,4'-biphenylidicarboxamide as a white solid (31.2 mg).

LC-MS: Rt 3.13 min, MH⁺ 397.

Example 18

N³-Cyclopropyl-5-fluoro-6-methyl-2'-(methyloxy)-N⁴'-{[4-(methyloxy)phenyl]methyl}-3,4-biphenyldicarboxamide

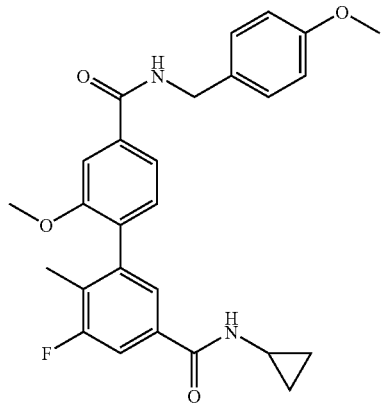

Intermediate 8 was reacted with 4-methoxybenzylamine according to General Method A. The residue was further purified using SPE (500 mg, SCX), eluting with chloroform. The solvent was evaporated to leave a colourless gel, which was triturated with ether to give N³-cyclopropyl-5-fluoro-6-methyl-2'-(methyloxy)-N⁴'-{[4-(methyloxy)phenyl]methyl}-3,4'-biphenylidicarboxamide as a white solid (17.5 mg).

LC-MS: Rt 3.30 min, MH⁺ 463.

Example 19

N³-Cyclopropyl-5-fluoro-6-methyl-2'-(methyloxy)-N⁴'-[(1R)-1,2,2-trirhethylpropyl]-3,4'-biphenyldicarboxamide

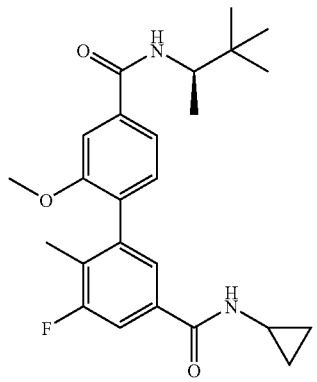

Intermediate 8 was reacted with (R)-3,3-dimethyl-2-butylamine according to General Method A. The residue was further purified using SPE (500 mg, SCX), eluting with chloroform. The solvent was evaporated to leave a colourless gel, which was triturated with ether to give N³-cyclopropyl-5-fluoro-6-methyl-2'-(methyloxy)-N⁴'-[(1R)-1,2,2-trimethylpropyl]-3,4'-biphenyldicarboxamide as a white solid (20.0 mg).

LC-MS: Rt 3.41 min, MH⁺ 427.

Example 20

N³-Cyclopropyl-N⁴'-[(1R)-1,2-dimethylpropyl]-5-fluoro-6-methyl-2'-(methyloxy)-3,4'-biphenyldicarboxamide

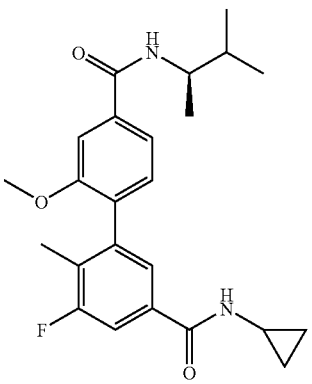

Intermediate 8 was reacted with (R)-(–)-3-methyl-2-butylamine according to General Method A. The residue was further purified using SPE (500 mg, SCX), eluting with chloroform. The solvent was evaporated to leave a colourless gel, which was triturated with ether to give N³-cyclopropyl-N⁴'-[(1R)-1,2-dimethylpropyl]-5-fluoro-6-methyl-2'-(methyloxy)-3,4'-biphenylidicarboxamide as a white solid (24.0 mg).

LC-MS: Rt 3.31 min, MH⁺ 413.

Example 21

N³-Cyclopropyl-N⁴'-(2,2-dimethylpropyl)-5-fluoro-6-methyl-2'-(propyloxy)-3,4'-biphenyldicarboxamide

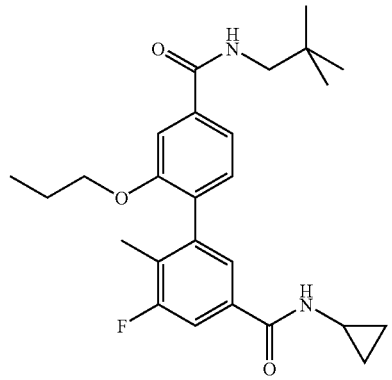

Intermediate 11 (47 mg) and HATU (67 mg) were combined in DMF (5 ml), diisopropylethylamine (83 μl) added and the reaction mixture left at room temperature for minutes. Neopentylamine (30 μl) was added and the mixture stirred at 20° C. under nitrogen for 19 hours. The solvent was evaporated and residue purified by mdap to leave N³-cyclopropyl-N⁴'-(2,2-dimethylpropyl)-5-fluoro-6-methyl-2'-(propyloxy)-3,4'-biphenylidicarboxamide as a white solid (10 mg).

LC-MS: Rt 3.50 min, MH⁺ 441.

Example 22

N³-Cyclopropyl-2'-{[3-(dimethylamino)propyl]oxy}-N⁴'-(2,2-dimethylpropyl)-5-fluoro-6-methyl-3,4'-biphenyldicarboxamide

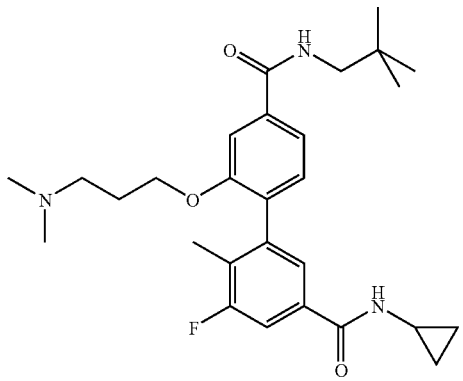

Intermediate 13 (30 mg), {5-[(cyclopropylamino)carbonyl]-3-fluoro-2-methylphenyl}boronic acid (23 mg) and tetrakis(triphenylphosphine) palladium (0) (5 mg) were combined in isopropanol (0.7 ml). Aqueous sodium hydrogen carbonate solution (1M, 243 µl) was added and the reaction heated at 90° C. under nitrogen for 4 hours. The solvent was evaporated and the residue partitioned between ethyl acetate/chloroform (1:1, 2×5 ml) and water (5 ml). The organic layers were combihed, dried using a hydrophobic filter, and the solvent evaporated in vacuo. The resulting gel was purified by mdap to give N³-cyclopropyl-2'-{[3-(dimethylamino)propyl]oxy}-N⁴'-(2,2-dimethylpropyl)-5-fluoro-6-methyl-3,4'-biphenylidicarboxamide as a colourless gel (20 mg).

LC-MS: Rt 2.53 min, MH⁺ 484.

Example 23

N³-Cyclopropyl-2'-{[3-(diethylamino)propyl]oxy}-N⁴'-(2,2-dimethylpropyl)-6-methyl-3A,-biphenyldicarboxamide

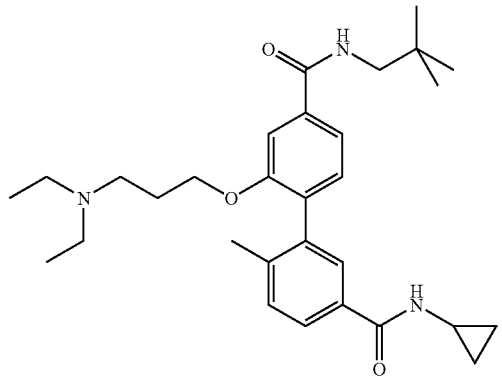

Intermediate 15 (20 mg) was dissolved in chloroform (0.5 ml), diethylamine (42 µl) added and the reaction left for 16 hours at 20° C. The solvent was removed and the residue purified by mdap to give N³-cyclopropyl-2'-{[3-(diethylamino)propyl]oxy}-N⁴'-(2,2-dimethylpropyl)-6-methyl-3,4'-biphenylidicarboxamide as a colourless gel (15.4 mg).

LC-MS: Rt 2.44 min, MH⁺ 494.

Example 24

N³-cyclopropyl-N⁴'-(2,2-dimethylpropyl)-6-methyl-2'-{[3-(4-morpholinyl)propyl]oxy}-3,4'-biphenyldicarboxamide

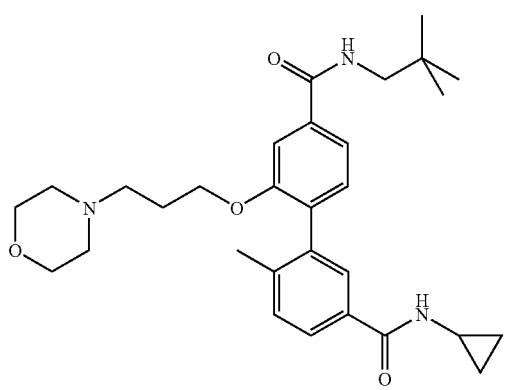

Intermediate 15 (20 mg) was dissolved in chloroform (0.5 ml), morpholine (35 µl) added and the reaction left for 16 hours at 20° C. The solvent was evaporated and the residue purified by mdap to give N³-cyclopropyl-N⁴'-(2,2-dimethylpropyl)-6-methyl-2'-{[3-(4-morpholinyl)propyl]oxy}-3,4'-biphenyldicarboxamide as a colourless gel (17.4 mg).

LC-MS: Rt 2.40 min, MH⁺ 508.

Example 25

N³-Cyclopropyl-N⁴'-(2,2-dimethylpropyl)-6-methyl-2'-({3-[(1-methylethyl)amino]propyl}oxy)-3,4'-biphenyldicarboxamide

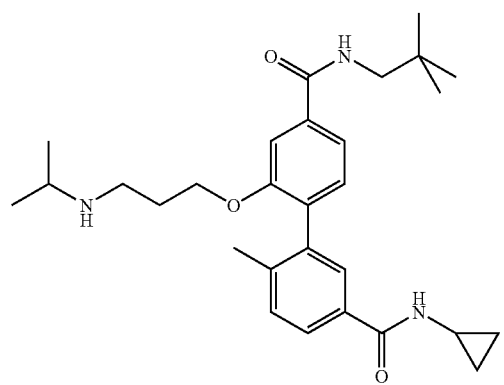

Intermediate 15 (20 mg) was dissolved in chloroform (0.5ml), isopropylamine (68 µl) added and the reaction left for 19 hours at 20° C. The solvent was evaporated and the residue purified by mdap to give N³-cyclopropyl-N⁴'-(2,2-dimethyl-propyl)-6-methyl-2'-({3-[(1-methylethyl)amino]propyl}oxy)-3,4'-biphenyldicarboxamide as a colourless gel (0.7 mg).

LC-MS: Rt 2.44 min, MH⁺ 480.

Example 26

N³-Cyclopropyl-N⁴'-(2,2-dimethylgropyl)-2'-({3-[(2-hydroxyethyl)amino]propyl}oxy)-6-methyl-3,4'-biphenyldicarboxamide

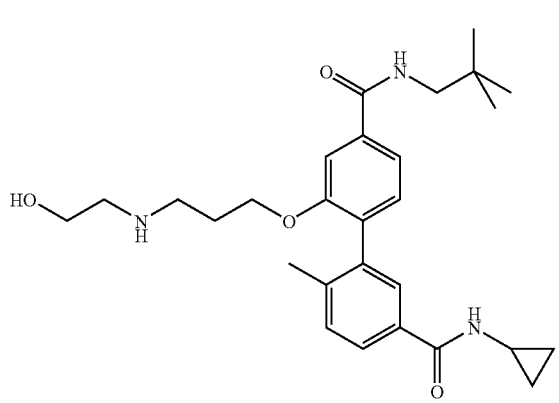

Intermediate 15 (20 mg) was dissolved in chloroform (0.5 ml), 2-(methylamino)-ethanol (32 µl) added and the reaction left for 16 hours at 20° C. The solvent was evaporated and the residue purified by mdap to give N³-cyclopropyl-N⁴'-(2,2-dimethylpropyl)-2'-({3-[(2-hydroxyethyl)amino]propyl}oxy)-6-methyl-3,4'-biphenyldicarboxamide as a colourless gel (14.7 mg).

LC-MS: Rt 2.38 min, MH⁺ 496.

Example 27

N³-Cyclopropyl-N⁴'-(2,2-dimethylpropyl)-6-methyl2'-({3-[methyl(1-methylethyl)amino]propyl}oxy)-3,4'-biphenyldicarboxamide

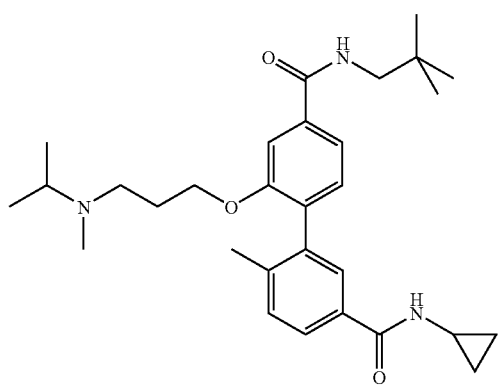

Intermediate 15 (20 mg) was dissolved in chloroform (0.5 ml), N-methyl-isopropylamine (41 µl) added and the reaction left for 16 hours at 20° C. The solvent was evaporated and the residue purified by mdap to give N³-cyclopropyl-N⁴'-(2,2-dimethylpropyl)-6-methyl-2'-({3-[methyl(1-methylethyl)amino]propyl}oxy)-3,4'-biphenyldicarboxamide as a colourless gel (13.8 mg).

LC-MS: Rt 2.44 min, MH⁺ 494.

Example 28

N³-Cyclopropyl-N⁴'-(2,2-dimethylpropyl)-6-methyl-2'-{[3-(1-pyrrolidinyl)propyl]oxy}-3,4'-biphenyldicarboxamide

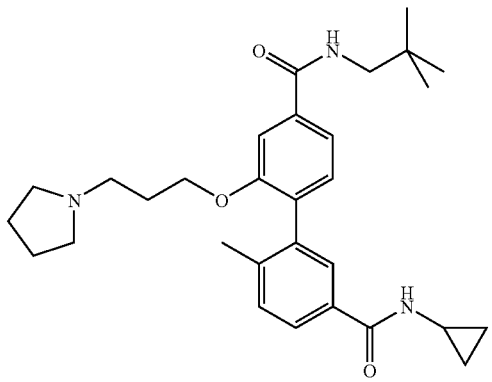

Intermediate 15 (20 mg) was dissolved in chloroform (0.5 ml), pyrrolidine (34 µl) added and the reaction left for 18 hours at 20° C. The solvent was evaporated and the residue purified by mdap to give N³-cyclopropyl-N⁴'-(2,2-dimethylpropyl)-6-methyl-2'-{[3-(1-pyrrolidinyl)propyl]oxy}-3,4'-biphenyldicarboxamide as a colourless gel (10.9 mg).

LC-MS: Rt 2.43 min, MH⁺ 492.

Example 29

N³-Cyclopropyl-N⁴'-(2,2-dimethylpropyl)-5-fluoro-6-methyl-2'-({2-[(methylsulfonyl)amino]ethyl}oxy)-3,4'-biphenyldicarboxamide

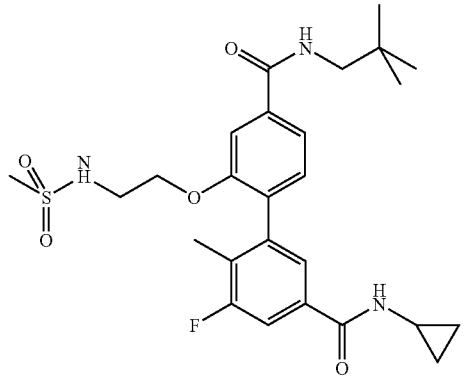

Intermediate 17 (34 mg), HATU (27 mg) and diisopropylamine (39 µl) were combined in DMF (2 ml) and the reaction mixture stood for 10 minutes. Neopentylamine (39 µl) was added and the reaction mixture stirred under nitrogen for 21 hours at 20° C. The solvent was evaporated and the residue purified by SPE (1 g, aminopropyl), eluting with 20% methanol in chloroform. The solvent was evaporated in vacuo to leave a yellow gel, which was purified by mdap, to give N³-cyclopropyl-N⁴'-(2,2-dimethylpropyl)-5-fluoro-6-methyl-2'-({2-[(methylsulfonyl)amino]ethyl}oxy)-3,4'-biphenyldicarboxamide as a white solid (22 mg).

LC-MS: Rt 3.08 min, MH⁺ 520.

Example 30

N³-Cyclopropyl-N⁴'-(2,2-dimethylpropyl)-5-fluoro-6-methyl-2'-{[2-(4-morpholinyl)ethyl]oxy}-3,4'-biphenyldicarboxamide

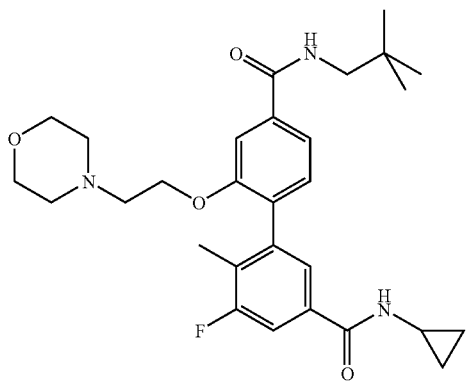

Intermediate 19 (20 mg), HATU (16 mg) and diisopropylamine (23 µl) were combined in DMF (1 ml) and the mixture stood for five minutes at 20° C. Neopentylamine (8 µl) was added and the reaction stood for 19 hours at 20° C. The solvent was evaporated in vacuo and residue purified by SPE (1 g aminopropyl), eluting with 10% methanol in chloroform. The solvent was evaporated and the residue purified by mdap to give N³-cyclopropyl-N⁴'-(2,2-dimethylpropyl)-5-fluoro-6-methyl-2'-{[2-(4-morpholinyl)ethyl]oxy}3,4'-biphenylidicarboxamide as a cblouriess gel (16 mg).

LC-MS: Rt 2.42 min, MH⁺ 512.

Example 31

N³-Cyclopropyl-N⁴'-(2,2-dimethylpropyl)-5-fluoro-6-methyl-2'-{[2-(4-morpholinyl)-2-oxoethyl]oxy}-3,4'-biphenyldicarboxamide

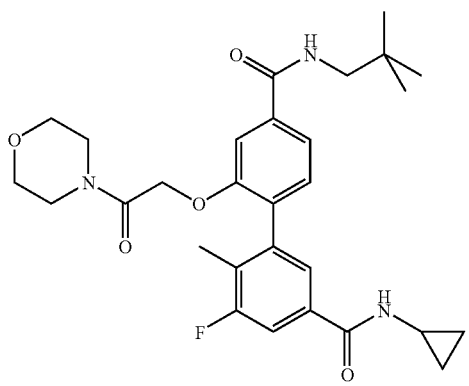

Intermediate 21 (11 mg), HATU (9 mg) and diisbpropylamine (13 µl) were combined in dry DMF (0.5 ml) and stood at 20° C. for 5 minutes. Neopentylamine (10 µl) was added and the reaction stood at 20° C. for 16 hours with occasional shaking. The solvent was evaporated in vacuo and the residue purified using an SPE (1 g, aminopropyl), eluting with 10% methanol in chloroform. The solvents were evaporated to leave a colourless gel, which was further purified by mdap, to give N³-cyclopropyl-N⁴'-(2,2-dimethylpropyl)-5-fluoro-6-methyl-2'-{[2-(4-morpholinyl)-2-oxoethyl]oxy}-3,4'-biphenylidicarboxamide as a colourless gel (6.4 mg).

LC-MS: Rt 3.02 min, MH⁺ 526.

Example 32

4-[(5'-[(Cyclopropylamino)carbonyl]-4-{[(2,2-dimethylpropyl)amino]carbonyl}-3'-fluoro-2'-mathyl-2-biphenylyl)oxy]butanoic acid

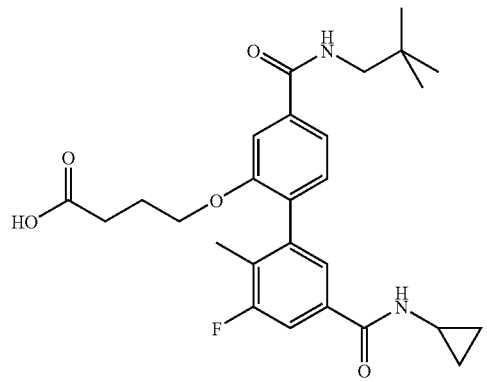

Intermediate 22 (368 mg), {5-[(cyclopropylamino)carbonyl]-3-fluoro-2-methylphenyl}boronic acid (270 mg) and tetrakis(triphenylphosphine) palladium (0) (50 mg) were combined in isopropanol (8.5 ml) and aqueous sodium hydrogen carbonate solution (1M, 2.85 ml) added. The reaction was stirred under nitrogen for 19 hours at 90° C. The solvent was evaporated and the residue partitioned between ethyl acetate and water. The organic layer was evaporated and the residue stirred in methanol (10 ml) and aqueous sodium hydroxide (2M, 10 ml) for 3 hours under nitrogen. The solvents were evaporated and the residue partitioned between ethyl acetate/chloroform (1:1) and water. The aqueous layer was acidified to pH 1 using hydrochloric acid (2M) and extracted with ethyl acetate/chloroform (1:1). The organic phase was dried using a hydrophobic filter and evaporated to leave a brown gel, which was triturated in diethyl ether to give 4-[(5'-[(cyclopropylamino)carbonyl]-4-{[(2,2-dimethylpropyl)amino]carbonyl}-3'-fluoro-2'-methyl-2-biphenylyl)oxylbutanoic acid as a grey solid.

LC-MS: Rt 3.16 min, MH⁺ 485.

Example 33

2'-[(4-Amino-4-oxobutyl)oxy]-$N^3$-cyclopropyl-$N^{4'}$-(2,2-dimethylpropyl)-5-fluoro-6-methyl-3,4'-biphenyldicarboxamide

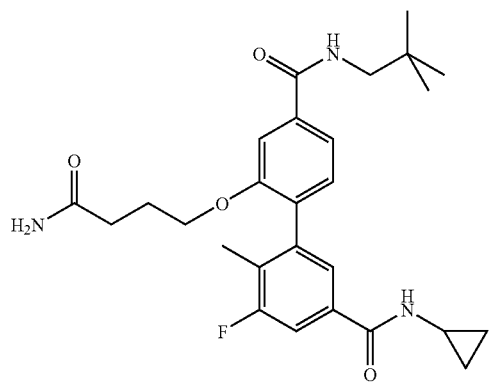

Example 32 (20 mg) was reacted with 0.880 aqueous ammonia solution (20 μl) according to General Method A. Further purification was done using mdap, to give 2'-[(4-amino-4-oxobutyl)oxy]-$N^3$-cyclopropyl-$N^{4'}$-(2,2-dimethylpropyl)-5-fluoro-6-methyl-3,4'-biphenylidicarboxamide.

LC-MS: Rt 2.99 min, MH$^+$ 484.

Example 34

$N^3$-Cyplopropyl-$N^{4'}$-(2,2-dimethylpropyl)-5-fluoro-6-methyl-2'-{[4-(methylamino)-4-oxobutyl]oxy}-3,4'-biphenyldicarboxamide

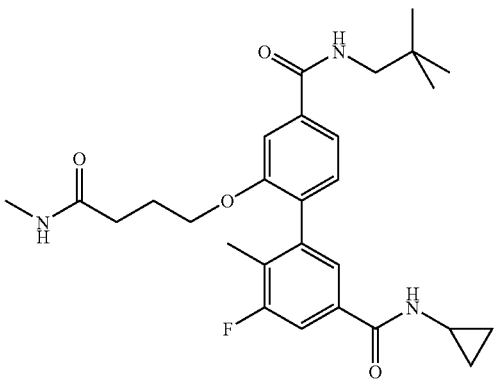

Example 32 (20 mg) was reacted with methylamine in THF (2M, 100 μl) according to General Method A. Further purification was done using mdap, to give $N^3$-cyclopropyl-$N^{4'}$-(2,2-dimethylpropyl)-5-fluoro6-methyl-2'-{[4-(methylamino)-4-oxobutyl]oxy}-3,4'-biphenylidicarboxamide.

LC-MS: Rt 3.06 min, MH$^+$ 498.

Example 35

$N^3$-Cyclopropyl-2'-{[4-(dimethylamino)-4-oxobutyl]oxy}-$N^{4'}$-(2,2dimethylpropyl)-5-fluoro-6-methyl-3,4'-biphenyldicarboxamide

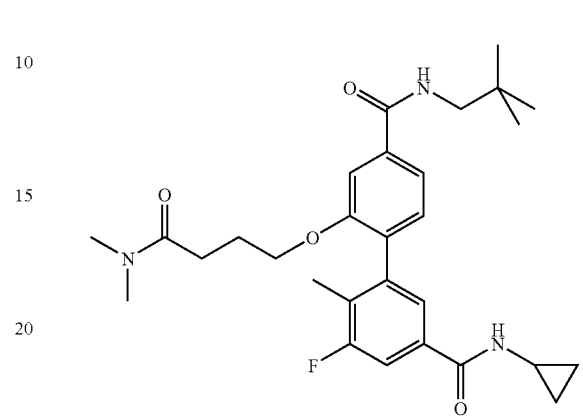

Example 32 (20 mg) was reacted with dimethylamine in THF (2M, 100 μl) according to General Method A. Further purification was done using mdap, to give $N^3$-cyclopropyl-2'-{[4-(dimethylamino)-4-oxobutyl]oxy}-$N^{4'}$-(2,2-dimethylpropyl)-5fluoro-6-methyl-3,4'-biphenylidicarboxamide.

LC-MS: Rt 3.13 min, MH$^+$ 512.

Example 36

$N^3$-Cylopropyl-$N^{4'}$-(2,2-dimethylpropyl)-2'-{[4-(ethylamino)-4-oxobutyl]oxy}-5-fluoro-6-methyl-3,4'-biphenyldicarboxamide

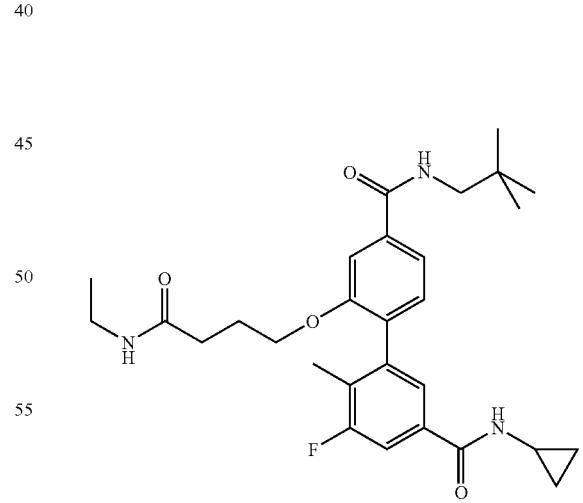

Example 32 (20 mg) was reacted with ethylamine in THF (2M, 100 μl) according to General Method A. Further purification was done using mdap, to give $N^3$-cyclopropyl-$N^{4'}$-(2,2-dimethylpropyl)-2'-{[4-(ethylamino)-4-oxobutyl]oxy}-5-fluoro-6-methyl-3,4'-biphenyldicarboxamide.

LC-MS: Rt 3.16 min, MH$^+$ 512.

Example 37

N³-Cyclopropyl-N⁴'-(2,2-dimethylpropyl)-5-fluoro-6-methyl-2'-{[4-oxo-4-(1-pyrrolidinyl)butyl]oxy}-3,4'-biphenyldicarboxamide

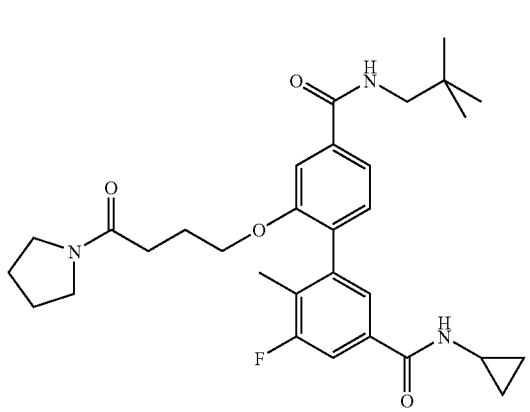

Example 32 (20 mg) was reacted with pyrrolidine (17 µl) according to General Method A. Further purification was done using mdap, to give N³-cyclopropyl-N⁴'-(2,2-dimethylpropyl)-5-fluoro-6-methyl-2'-{[4-oxo-4-(1-pyrrolidinyl)butyl]oxy}-3,4'-biphenyldicarboxamide.

LC-MS: Rt 3.19 min, MH⁺ 538.

Example 38

N³-Cyclopropyl-N⁴'-(2,2-dimethylpropyl)-5-fluoro-6-methyl-2'-{[4(4-morpholinyl)-4-oxobutyl]oxy}-3,4'-biphenyldicarboxamide

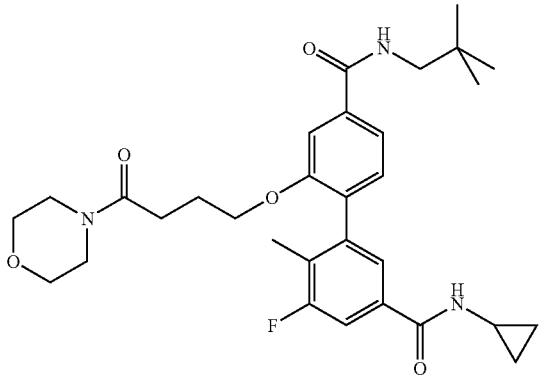

Example 32 (20 mg) was reacted with morpholine (18 µl) according to General Method A. Further purification was done using mdap, to give N³-cyclopropyl-N⁴'-(2,2-dimethylpropyl)-5-fluoro-6-methyl-2'-{[4-(4-morpholinyl)4-oxobutyl]oxy}-3,4'-biphenylidicarboxamide.

LC-MS: Rt 3.10 min, MH⁺ 554.

Example 39

N³-Cyclopropyl-N⁴'-(2,2-dimethylpropyl)-5-fluoro-2'-[(4-hydroxybutyl)oxy]-6-methyl-3,4'-biphenyldicarboxamide

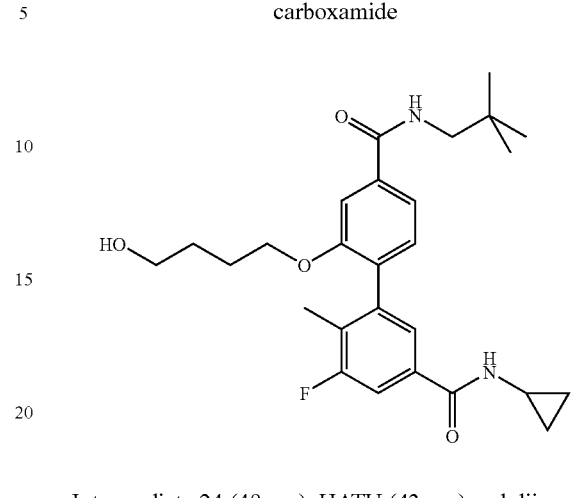

Intermediate 24 (49 mg), HATU (43 mg) and diisopropylamine (64 µl) were combined in DMF (3 ml) and stood for 5 minutes at 20° C. Neopentylamine (25 µl) was added and the reaction stirred at 20° C. under nitrogen for 5 hours. The solvent was evaporated under vacuum and residue partially purified using SPE (1 g, aminopropyl), eluting with 10% methanol in chloroform. The product was further purified using mdap, which gave, after evaporation of the solvent N³-cyclopropyl-N⁴'-(2,2-dimethylpropyl)-5-fluoro-2'-[(4-hydroxybutyl)oxy]-6-methyl-3,4'-biphenyldicarboxamide as a colourless gel (27 mg).

LC-MS: Rt 3.15 min, MH⁺ 471.

Example 40

N³-Cyclopropyl-N⁴'-(2,2-dimethylpropyl)-5-fluoro-6-methyl-2'-{[3-(1,3,4-oxadiazol-2-yl)propyl]oxy}-3,4'-biphenyldicarboxamide

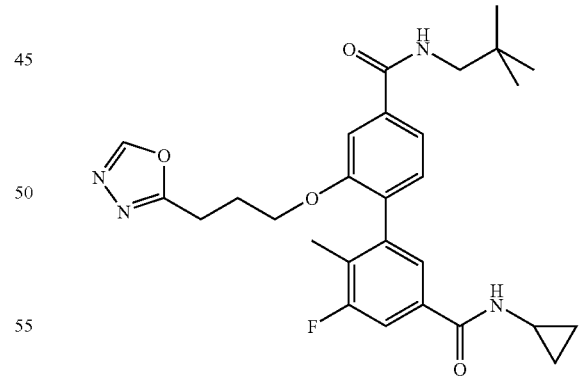

Intermediate 26 (20 mg) was added to triethylorthoformate (2 ml) and heated at 80° C. under nitrogen for 48 hours and subsequently at 130° C. for 3 hours without a condenser. The excess triethylorthoformate was evaporated in vacuo and the residue purified by mdap; which gave after evaporation of the solvents N³-cyclopropyl-N⁴'-(2,2-dimethylpropyl)-5-fluoro-6-methyl-2'-{[3-(1,3,4-oxadiazol-2-yl) propyl]oxy}-3,4'-biphenydicarboxamide as a white solid.

LC-MS: Rt 3.14 min, MH⁺ 509.

Example 41

N³-Cyclopropyl-2'-[(2.3-dihydroxypropyl)oxy]-N⁴'-(2,2-dimethvypropyl)-6-methyl-3,4'-biphenyldicarboxamide

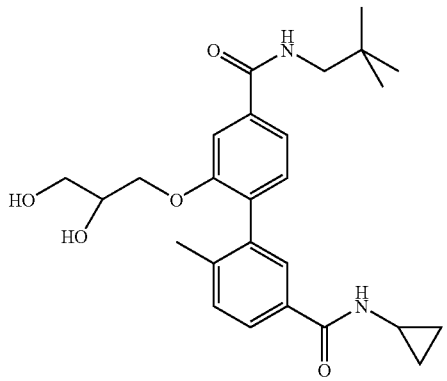

Intermediate 27 (43 mg), N-cyclopropyl-4-methyl-3-(4,4,5,5-tetramethyl-1,3,2-dioxaborolanyl)benzamide (39 mg) and tetrakis(triphenylphosphine) palladium (0) (5 mg) were combined in isopropanol (1 ml) and aqueous sodiumhydrogen carbonate (1M, 321 µl) added. The reaction was heated under nitrogen at 90° C. for 16 hours. The solvent was evaporated in vacuo and the residue partitioned between water (10 ml) and ethyl acetate:chloroform (1:1, 10 ml). The organic phase was dried using a hydrophobic filter and solvent evaporated under vacuum. The residue was stirred in hydrochloric acid in 1,4-dioxane (4M, 2 ml) for 3 hours at 20° C. The solvent was evaporated, the residue was purified by mdap and then further purified using SPE (1 g, Si) eluting with an ethyl acetate/cyclohexane gradient (0-100%). The product containing fractions were combined and evaporated in vacuo to give N³-cyclopropyl-2'-[(2,3-dihydroxypropyl)oxy]-N⁴'-(2,2-dimethylpropyl)-6-methyl-3,4'-biphenylidicarboxamide as a yellow gel (7 mg).

LC-MS: Rt 2.75 min, MH⁺ 455.

Example 42

N³-Cyclopropyl-N⁴'-(2,2-dimethylpropyl)-2'-{[(2,2-dimethylpropyl)amino]methyl}-5-fluoro-6-methyl-3,4'-biphenyldicarboxamide

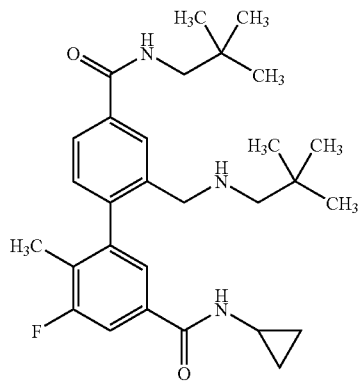

Intermediate 31 (28 mg), {5-[(cyclopropylamino)carbonyl]-3-fluoro-2-methylphenyl}boronic acid (20.5 mg), tetrakis(triphenylphosphine)palladium (2 mg) and aqueous sodium hydrogen carbonate (1M, 0.6 ml) in isopropanol (1.5 ml) were heated by microwave in a sealed vessel for 150° C. for 15 mins. The reaction was purified by preparative HPLC (mdap) to give after evaporation of the solvents N³-cyclopropyl-N⁴'-(2,2-dimethylpropyl)-2'-{[(2,2-dimethylpropyl)amino]methyl}-5-fluoro-6-methyl-3,4'biphenylidicarboxamide.

LCMS: Rt 2.45 mins, MH⁺ 482.

Example 43

N³-Cyclopropyl-N⁴'-(2,2-dimethylpropyl)-5-fluoro-2'-(hydroxymethyl)-6-methyl-3,4'-biphenyldicarboxamide

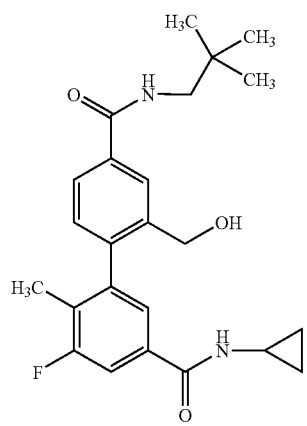

Sodium borohydride (10 mg) was added portionwise to a solution of Intermediate 32 (10 mg) in ethanol (0.5 ml). The reaction was stirred at 0° C. for 30 mins before methanol (2ml) was added to the reaction and stirring continued for 2 hrs at room temperature. The solvents were evaporated and the residue partitioned between chloroform and water. The organic phase was dried (hydrophobic frit) and evaporated to give N³-cyclopropyl-N⁴'-(2,2-dimethylpropyl)-5-fluoro-2'-(hydroxymethyl)-6-methyl-3,4'-biphenyldicarboxamide (4 mg).

LCMS: Rt 3.02 mins, MH⁺ 413.

Example 44

2'-Amino-N³-cyclopropyl-N⁴'-(2,2-dimethylpropyl)-6-methyl-3,4'-biphenyldicarboxamide

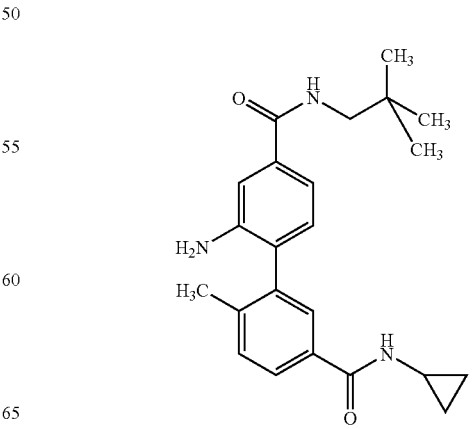

Intermediate 35 (350 mg) and palladium on carbon (10% w/w, wet) in ethanol (7 ml) were hydrogenated under 1 Atm. of hydrogen at room temperature for 18 hrs. The reaction was filtered through celite and the filtrate reduced to dryness under vacuum. The residue was dissolved in methanol and applied to an SPE (aminopropyl), and the column eluted with methanol and then ammonia/methanol (0.880 ammonia, 10% v/v). Evaporation of the solvents from the ammonia/methanol fractions in vacuo gave 2'-amino-$N^3$-cyclopropyl-$N^{4'}$-(2,2-dimethylpropyl)-6-methyl-3,4'-biphenyldicarboxamide (270 mg) as a white solid.

LCMS: MH$^+$ 380, Rt 2.89 min.

Example 45

$N^3$-Cyclopropyl-$N^{4'}$-(2,2-dimethylpropyl)-6-methyl-2'-(propanoylamino)-3,4'-biphenyldicarboxamide

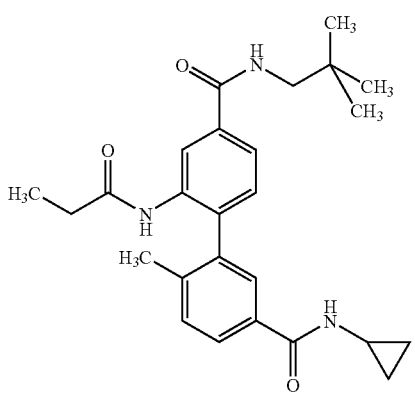

Example 44 (50 mg), sodium carbonate (17 mg) and propanoyl chloride (14.4 mg) were stirred for 18hrs in DCM (5 ml). Further sodium carbonate (17 mg) and propanoyl chloride (14.4 mg) were added and the reaction heated at 50° C. for 5 hours. The mixture was filtered and the filtrate reduced to dryness under vacuum. The residue was dissolved in methanol and filtered through an SPE (SCX), concentration of the eluent gave $N^3$-cyclopropyl-$N^{4'}$-(2,2-dimethylpropyl)-6-methyl-2'-(propanoylamino)-3,4'-biphenylidicarboxamide as a white solid (4.1 mg).

LCMS: Rt 2.85 min, MH$^+$ 436.

Example 46

2'-(Acetylamino)-$N^3$-cyclopropyl-$N^{4'}$-(2,2-dimethylpropyl)-6-methyl-3,4'-biphenyldicarboxamide

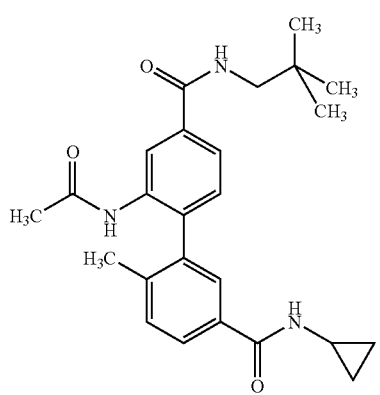

Example 44 (50 mg), sodium carbonate (17 mg) and acetyl chloride (12.2 mg) were stirred for 18 hrs in DCM (5 ml).

Further sodium carbonate (17 mg) and acetyl chloride (12.2 mg) were added and the reaction heated at 50° C. for 5 hours. The mixture was filtered and the filtrate reduced to dryness under vacuum. The residue was dissolved in methanol and filtered through an SPE (SCX), concentration of the eluent gave 2'-(acetylamino)-$N^3$-cyclopropyl-$N^{4'}$-(2,2dimethylpropyl)-6-methyl-3,4'-biphenyldicarboxamide as a white solid (20 mg).

LCMS: MH$^+$ 422, Rt 2.75 min.

Example 47

$N^3$-Cyclopropyl-$N^{4'}$-(2,2-dimethylpropyl)-2'-{[(ethylamino)carbonyl]amino}-6-methyl-3,4'-biphenyldicarboxamide

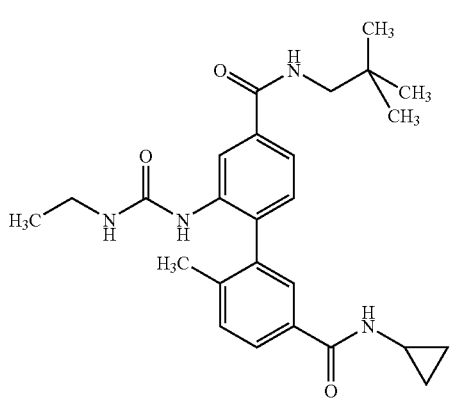

Example 44 (50 mg) in DCM (5 ml) was added dropwise to a solution of 1,1-carbonyldiimidazole (32 mg) in DCM (5 ml) at 020 C. The reaction was stirred at 0° C. for 1 hour and then at room temperature overnight and at 45° C. for 5 hours. DIPEA (45.8 µl) and DMAP (16 mg) were added to the reaction and the mixture stirred at room temperature for 18 hours. Ethylamine (2M in THF, 99 µl) was added and the solution stirred for 5 hours at room temperature. The solvents were evaporated under vacuum and methanol (10 ml) added to the residue. The resuling white solid was filtered off and washed with methanol to give $N^3$-cyclopropyl-$N^{4'}$-(2,2-dimethylpropyl)-2'-{[(ethylamino)carbonyl]amino}6-methyl-3,4'-biphenylidicarboxamide (25 mg).

LCMS: MH$^+$ 451, Rt 2.97 mins.

Example 48

$N^3$-Cyclopropyl-$N^{4'}$-(2,2-dimethylproiyl)-6-methyl-2'-[(methylsulfonyl) amino]-3,4'-biphenyldicarboxamide

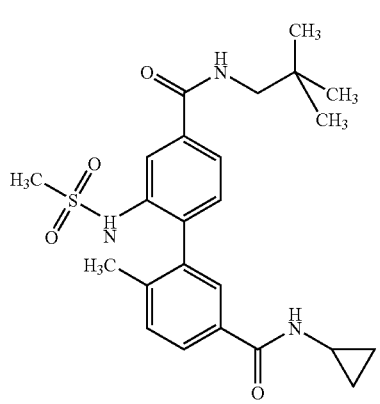

Methanesuiphonyl chloride (6.75 µl) was added to a solution of Example 44 (30 mg) in pyridine (3 ml) at 0° C. and the reaction stirred at 0° C. for 30 min and then at room temperature for 18 hours. Methanesulphonyl chloride (6.75 µl) was added and the reaction heated at 60° C. overnight. Methanesulphonyl chloride (6.75 µl), DMAP (9.7 mg) and DIPEA (13.8 µl) were added and the reaction stirred at room temperature overnight. The pyridine was evaporated in vacuo and the residuediluted with methanol and filtered through an SPE cartridge (SCX). The filtrate was reduced to dryness in vacuo and further purified by chromatography on an SPE cartridge (Si) elubng With ethyl acetate/cyclohexane (1:1) to give after evaporation of the solvents $N^3$-cyclopropyl-$N^{4'}$-(2,2-dimethylpropyl)-6-methyl-2'-[(methylsulfonyl)amino]-3,4'-biphenyldicarboxamide (20 mg) as a white solid.

LCMS: $MH^+$ 458, Rt 2.93 mins.

ABBREVIATIONS

Ac Acetyl
ADDP 1,1-Azadicarbonyldipiperadine
Boc t-Butoxycarbonyl
Bu Butyl
DCM Dichloromethane
DIPEA N,N-Diisopropylethylamine
DMAP 4-(Dimethylamino)pylpdine
DMF Dimethylformamide
EtOH Ethanol
Hal Halogen
HATU O-(7-Azabenzotidazol-1-yl)-N,N,N',N'-tetramethyluronium hexafluorophosphate
IPA isopropanol
iPr isopropyl
KOAc Potassium acetate
mDap Mass-directed autopreparative HPLC
MeOH Methanol
min Minutes
PdCl$_2$dppf [1,1'-bis(diphenylphosphino)ferrocene]dichloropalladium (II) complex with dichloromethane (1:1)
Ph Phenyl
Rt Retention time
SPE Solid phase extraction
THF Tetrahydrofuran

BIOLOGICAL EXAMPLES

The activity of compounds of formula (I) as p38 inhibitors may be determined by the following in vitro assays:

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurably different from the bound value.

The concentration of kinase enzyme should preferably be ≧1×$K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All components dissolved in Buffer of final composition 62.5 mM HEPES, pH 7.5, 1.25 mM CHAPS, 1.25 mM DTT, 12.5 mM MgCl$_2$ 3.3% DMSO.

p38 Enzyme concentration: 12 nM
Fluorescent ligand concentration: 5 nM
Test compound concentration: 0.1 nM -100 uM
Components incubated in 30 ul final volume in NUNC 384 well black microtitre plate until equilibrium reached (5-30 mins)
Fluorescence anisotropy read in LJL Acquest.

Definitions: $K_i$=dissociation constant for Inhibitor binding
$K_f$=dissociation constant for fluorescent ligand binding
The fluorescent ligand is the following compound:

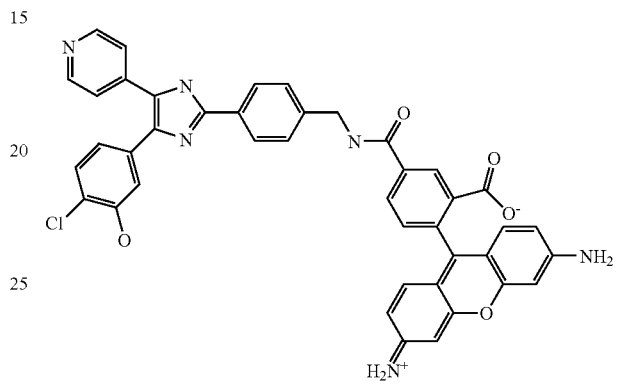

which is derived from 5-[2-(4-aminomethylphenyl)-5-pyridin-4-yl-1H-imidazol4-yl]-2-chlorophenol and rhodamine green.

Results

The compounds described in the Examples were tested as described above and had IC$_{50}$ values of <10 µM.

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims:

The invention claimed is:
1. A compound of formula (I):

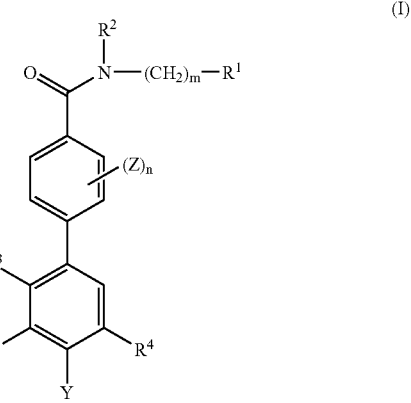

wherein
- $R^1$ is selected from hydrogen, $C_{1-6}$alkyl optionally substituted by up to three groups independently selected from $C_{1-6}$alkoxy, halogen and hydroxy, $C_{2-6}$alkenyl, $C_{3-7}$cycloalkyl optionally substituted by one or more $C_{1-6}$alkyl groups, phenyl optionally substituted by up to three groups independently selected from $R^5$ and $R^6$ or heteroaryl optionally substituted by up to three groups independently selected from $R^5$ and $R^6$,
- $R^2$ is selected from hydrogen, $C_{1-6}$alkyl or $—(CH_2)_p—C_{3-7}$ cycloalkyl optionally substituted by one or more $C_{1-6}$alkyl groups,
- or $(CH_2)_m R^1$ and $R^2$, together with the nitrogen atom to which they are bound, form a four- to six-membered heterocyclic ring optionally substituted by up to three $C_{1-6}$alkyl groups;
- $R^3$ is chloro or methyl;
- $R^4$ is the group $—NH—CO—R^7$ or $—CO—NH—(CH_2)_p—R^8$;
- $R^5$ is selected from $C_{1-6}$alkyl, $C_{1-6}$alkoxy, $—(CH_2)_p—C_{3-7}$ cycloalkyl optionally substituted by one or more $C_{1-6}$alkyl groups, $—CONR^9R^{10}$, $—NHCOR^{10}$, $—SO_2NHR^9$, $—(CH_2)_q NHSO_2R^{10}$, halogen, CN, OH, $—(CH_2)_q NR^{11}R^{12}$ or trifluoromethyl;
- $R^6$ is selected from $C_{1-6}$alkyl, $C_{1-6}$alkoxy, halogen, trifluoromethyl or $—(CH_2)_q NR^{11}R^{12}$;
- $R^7$ is selected from hydrogen, $C_{1-6}$alkyl, $—(CH_2)_p—C_{3-7}$ cycloalkyl optionally substituted by one or more $C_{1-6}$alkyl groups, trifluoromethyl, $—(CH_2)_r$heteroaryl optionally substituted by $R^{13}$ and/or $R^{14}$ or $—(CH_2)_r$phenyl optionally substituted by $R^{13}$ and/or $R^{14}$;
- $R^8$ is selected from hydrogen, $C_{1-6}$alkyl, $C_{3-7}$cycloalkyl optionally substituted by one or more $C_{1-6}$alkyl groups, $CONHR^9$, phenyl optionally substituted by $R^{13}$ and/or $R^{14}$ or heteroaryl optionally substituted by $R^{13}$ and/or $R^{14}$;
- $R^9$ and $R^{10}$ are each independently selected from hydrogen or $C_{1-6}$alkyl, or
- $R^9$ and $R^{10}$, together with the nitrogen atom to which they are bound, form a five- to six-membered heterocyclic ring optionally containing one additional heteroatom selected from oxygen, sulfur and $N—R^{15}$, wherein the ring is optionally substituted by up to two $C_{1-6}$alkyl groups;
- $R^{11}$ is selected from hydrogen, $C_{1-6}$alkyl or $—(CH_2)_p—C_{3-7}$cycloalkyl optionally substituted by one or more $C_{1-6}$alkyl groups;
- $R^{12}$ is selected from hydrogen or $C_{1-6}$alkyl, or
- $R^{11}$ and $R^{12}$, together with the nitrogen atom to which they are bound, form a five or six-membered heterocyclic ring optionally containing one additional heteroatom selected from oxygen, sulfur and $N—R^{15}$;
- $R^{13}$ is selected from $C_{1-6}$alkyl, $C_{1-6}$alkoxy, $—(CH_2)_p—C_{3-7}$ cycloalkyl optionally substituted by one or more $C_{1-6}$alkyl groups, $—CONR^9R^{10}$, $—NHCOR^{10}$, halogen, CN, $—(CH_2)_q NR^{11}R^{12}$, trifluoromethyl, phenyl optionally substituted by one or more $R^{14}$ groups or heteroaryl optionally substituted by one or more $R^{14}$ groups;
- $R^{14}$ is selected from $C_{1-6}$alkyl, $C_{1-6}$alkoxy, halogen, trifluoromethyl or $—NR^{11}R^{12}$;
- $R^{15}$ is selected from hydrogen or methyl;
- X and Y are each independently selected from hydrogen, methyl or halogen;
- Z is selected from $—(CH_2)_s OR^{16}$, $—(CH_2)_s NR^{16}R^{17}$, $—(CH_2)_s CH_2CH_2R^{16}$, $—(CH_2)_s COOR^{16}$, $—(CH_2)_s CONR^{16}R^{17}$, $—(CH_2)_s NHCONR^{16}R^{17}$, $—(CH_2)_s SO_2R^{16}$, $—(CH_2)_s SO_2NR^{16}R^{17}$ or $—(CH_2)_s NHSO_2R^{16}$;
- $R^{16}$ is selected from hydrogen, $C_{1-6}$alkyl optionally substituted by up to two hydroxy groups, $—(CH_2)_t OR^{18}$, $—(CH_2)_t NR^{18}R^{19}$, $—(CH_2)_t NHSO_2R^{18}$, $—(CH_2)_t CONR^{18}R^{19}$, $—(CH_2)_t COOR^{18}$, $—(CH_2)_t$heteroaryl optionally substituted by up to two groups independently selected from halogen, $C_{1-6}$alkyl or oxo, or $—(CH_2)_t$phenyl optionally substituted by up to two groups independently selected from halogen, $C_{1-6}$alkyl or $C_{1-6}$alkoxy,
- $R^{17}$ is selected from hydrogen or $C_{1-6}$alkyl, or
- $R^{16}$ and $R^{17}$, together with the nitrogen atom to which they are bound, form a five- to six-membered heterocyclic ring optionally containing one additional heteroatom selected from oxygen, sulfur and $N—R^{15}$, wherein the ring is optionally substituted by up to two groups independently selected from oxo, halogen or $C_{1-6}$alkyl;
- $R^{18}$ and $R^{19}$ are each independently selected from hydrogen or $C_{1-6}$alkyl optionally substituted by up to two hydroxy groups, or
- $R^{18}$ and $R^{19}$, together with the nitrogen atom to which they are bound, form a five- to six-membered heterocyclic ring optionally containing one additional heteroatom selected from oxygen, sulfur and $N—R^{15}$, wherein the ring is optionally substituted by up to two groups independently selected from oxo, halogen or $C_{1-6}$alkyl;
- m is selected from 0, 1, 2, 3 or 4, wherein each carbon atom of the resulting carbon chain may be optionally substituted with up to two groups independently selected from $C_{1-6}$alkyl or halogen;
- n is 1;
- p is selected from 0, 1 or 2;
- q is selected from 0, 1, 2 or 3;
- r is selected from 0 or 1;
- s is selected from 0, 1, 2, 3 and 4; and
- t is selected from 1, 2, 3 or 4;

or a pharmaceutically acceptable salt thereof.

2. A compound according to claim 1 wherein $R^1$ is selected from $C_{1-6}$alkyl, $C_{3-7}$cycloalkyl or phenyl optionally substituted by up to three groups selected from $R^5$ and $R^6$.

3. A compound according to claim 1 wherein $R^1$ is $C_{3-6}$cycloalkyl.

4. A compound according to claim 1 wherein $R^2$ is hydrogen.

5. A compound according to claim 1 wherein m is 0 or 1.

6. A compound according to claim 1 wherein m is 1.

7. A compound according to claim 1 wherein $R^8$ is $C_{3-6}$cycloalkyl.

8. A compound according to claim 1 wherein Z is selected from $—(CH_2)_s OR^{16}$, $—(CH_2)_s NR^{16}R^{17}$, $—(CH_2)_s NHCONR^{16}R^{17}$ and $—(CH_2)_s NHSO_2R^{16}$.

9. A compound according to claim 1
- $N^3$-cyclopropyl-5-fluoro-2'-hydroxy-6-methyl-$N^{4'}$-[(4-methylphenyl)methyl]-3,4'- biphenyldicarboxamide;
- $N^3$-cyclopropyl-$N^{4'}$-(2,2dimethylpropyl)5-fluoro-6-methyl-2'-{[(methyloxy)methyl]oxy}-3,4'-biphenyldicarboxamide;
- $N^3$-cyclopropyl-5-fluoro-6-methyl-2'-{[(methyloxy)methyl]oxy}-$N^{4'}$-(2-methylpropyl)-3,4'-biphenyldicarboxamide;
- $N^3$-cyclopropyl-$N^{4'}$-(cyclopropylmethyl)-5-fluoro-6-methyl-2'-{[(methyloxy)methyl]oxy}-3,4'-biphenyldicarboxamide;

N³-cyclopropyl-5-fluoro-6-methyl-2'-{[(methyloxy)methyl]oxy}-N⁴'-{[4-(methyloxy)phenyl]methyl}-3,4'-biphenyldicarboxamide;
N³-cyclopropyl-5-fluoro-6-methyl-2'-{[(methyloxy)methyl]oxy}-N⁴'-[(1R)-1,2,2-trimethylpropyl]-3,4'-biphenyldicarboxamide;
N³-cyclopropyl-N⁴'-[(1R)-1,2-dimethylpropyl]-5-fluoro-6-methyl-2'-{[(methyloxy)methyl]oxy}-3,4'-biphenyldicarboxamide;
N³-cyclopropyl-N⁴'-(2,2-dimethylpropyl)-5-fluoro-2'-hydroxy-6-methyl-3,4'-biphenyldicarboxamide;
N³-cyclopropyl-5-fluoro-2'-hydroxy-6-methyl-N⁴'-(2-methylpropyl)-3,4'-biphenyldicarboxamide;
N³-cyclopropyl-N⁴'-(cyclopropylmethyl)-5-fluoro-2'-hydroxy-6-methyl-3,4'-biphenyldicarboxamide;
N³-cyclopropyl-5-fluoro-2'-hydroxy-6-methyl-N⁴'-{[4-(methyloxy)phenyl]methyl}-3,4'-biphenyldicarboxamide;
N³-cyclopropyl-5-fluoro-2'-hydroxy-6-methyl-N⁴'-[(1R)-1,2,2-trimethylpropyl]-3,4'-biphenyldicarboxamide;
N³-cyclopropyl-N⁴'-[(1R)-1,2-dimethylpropyl]-5-fluoro-2'-hydroxy-6-methyl-3,4'-biphenyldicarboxamide;
N³-cyclopropyl-N⁴'-(2,2-dimethylpropyl)-5-fluoro-6-methyl-2'-(methyloxy)-3,4'-biphenyldicarboxamide;
N³-cyclopropyl-5-fluoro-6-methyl-2'-(methyloxy)-N⁴'-(2-methylpropyl)-3,4'-biphenyldicarboxamide;
N³-cyclopropyl-N⁴'-(cyclopropylmethyl)-5-fluoro-6-methyl-2'-(methyloxy)3,4'-biphenyldicarboxamide;
N³-cyclopropyl-5-fluoro-6-methyl-2'-(methyloxy)-N⁴'-{[4-(methyloxy)phenyl]methyl}-3,4'-biphenyldicarboxamide;
N³-cyclopropyl-5-fluoro-6-methyl-2'-(methyloxy)-N⁴'-[(1R)-1,2,2-trimethylpropyl]-3,4'-biphenyldicarboxamide;
N³-cyclopropyl-N⁴'-[(1R)-1,2-dimethylpropyl]-5-fluoro-6-methyl-2'-(methyloxy)-3,4'-biphenyldicarboxamide;
N³-cyclopropyl-N⁴'-(2,2-dimethylpropyl)-5-fluoro-6-methyl-2'-(propyloxy)-3,4'-biphenyldicarboxamide;
N³-cyclopropyl-2'-{[3-(dimethylamino)propyl]oxy}-N⁴'-(2,2-dimethylpropyl)5-fluoro-6-methyl-3,4'-biphenyldicarboxamide;
N³-cyclopropyl-N⁴'-(2,2dimethylpropyl)-5-fluoro-6-methyl-2'-({2-[(methylsulfonyl)amino]ethyl}oxy)-3,4'-biphenyldicarboxamide;
4-[(5'-[(cyclopropylamino)carbonyl]-4-{[(2,2-dimethylpropyl)amino]carbonyl}-3'-fluoro-2'-methyl-2-biphenylyl)oxy]butanoic acid;
2'-[(4-amino-4-oxobutyl)oxy]-N³-cyclopropyl-N⁴'-(2,2-dimethylpropyl)-5-fluoro-6-methyl-3,4'-biphenyldicarboxamide;
N³-cyclopropyl-N⁴'-(2,2-dimethylpropyl)-5-fluoro-6-methyl-2'-{[4-(methylamino)-4-oxobutyl]oxy}-3,4'-biphenyldicarboxamide;
N³-cyclopropyl-N⁴'-(2,2-dimethylpropyl)-5-fluoro-2'-[(4-hydroxybutyl)oxy]-6-methyl-3,4'-biphenyldicarboxamide;
N³-cyclopropyl-N⁴'-(2,2-dimethylpropyl)-5-fluoro-6-methyl-2'-{[3-(1,3,4-oxadiazol-2-yl)propyl]oxy}-3,4'-biphenyldicarboxamide; and
N³-cyclopropyl-N⁴'-(2,2-dimethylpropyl)-5-fluoro-2'-(hydroxymethyl)-6-methyl-3,4'-biphenyldicarboxamide;
or a pharmaceutically acceptable salt thereof.

10. A process for preparing a compound according to claim 1, or a pharmaceutically acceptable salt thereof, which comprises:

(a) reacting a compound of (II)

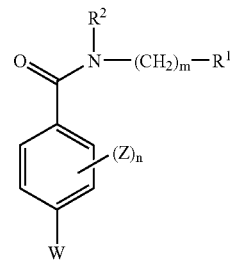

(II)

in which R¹, R², Z, m and n are as defined in claim 1 and W is halogen, with a compound of formula (III)

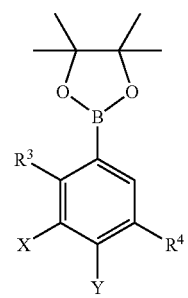

(III)

in which R³, R⁴, X and Y are as defined in claim 1, in the presence of a catalyst, or (b) reacting a compound of formula (VIII)

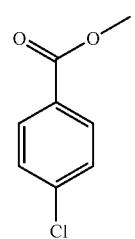

(VIII)

with a compound of formula (III) as hereinbefore defined and then reacting the acid thus formed with an amine of formula (V)

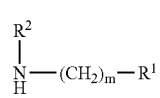

(V)

in which R¹, R² and m are as defined in claim 1, under amide forming conditions (c) reacting a compound of formula (II) as hereinbefore defined with a compound of formula (IX)

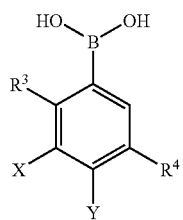

in which $R^3$, $R^4$, X and Y are as defined in claim 1, in the presence of a catalyst, (d) reacting a compound of formula (X)

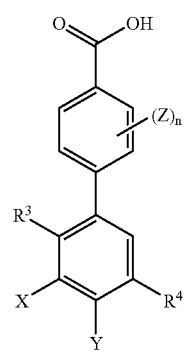

in which $R^3$, $R^4$, X, Y, Z and n are as defined in claim 1, with an amine compound of formula (V) as defined above, under amide forming conditions, (e) final stage modification of one compound of formula (I) into another compound of formula (I), or (f) conversion of a compound of formula (XII)

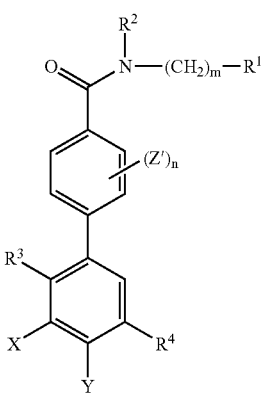

in which Z' is a group convertible to Z as defined in claim 1.

11. A pharmaceutical composition comprising at least one compound according to claim 1, or a pharmaceutically acceptable salt thereof, in association with one or more pharmaceutically acceptable excipients, diluents and/or carriers.

12. A method for treating inflammation in a human in need thereof comprising administering to said human an effective amount of a compound according to claim 1, or a pharmaceutically acceptable salt thereof.

13. A compound of formula (IA):

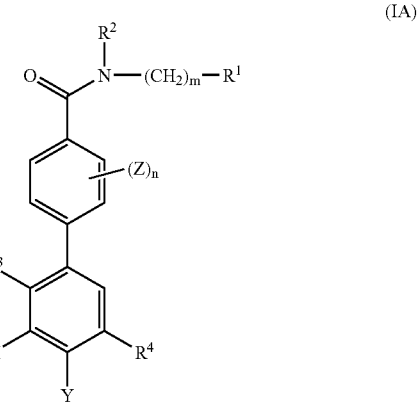

wherein $R^1$ is selected from hydrogen, $C_{1-6}$alkyl optionally substituted by up to three groups independently selected from $C_{1-6}$alkoxy, halogen or hydroxy, $C_{2-6}$alkenyl, $C_{3-7}$cycloalkyl optionally substituted by one or more $C_{1-6}$alkyl groups, phenyl optionally substituted by up to three groups independently selected from $R^5$ and $R^6$, or heteroaryl optionally substituted by up to three groups independently selected from $R^5$ and $R^6$, $R^2$ is selected from hydrogen, $C_{1-6}$alkyl or —$(CH_2)_p$—$C_{3-7}$ cycloalkyl optionally substituted by one or more $C_{1-6}$alkyl groups, or $(CH_2)_m R^1$ and $R^2$, together with the nitrogen atom to which they are bound, form a four- to six-membered heterocyclic ring optionally substituted by up to three $C_{1-6}$alkyl groups;

$R^3$ is chloro or methyl;

$R^4$ is the group —NH—CO—$R^7$ or —CO—NH—$(CH_2)_p$—$R^8$;

$R^5$ is selected from $C_{1-6}$alkyl, $C_{1-6}$alkoxy, —$(CH_2)_p$—$C_{3-7}$ cycloalkyl optionally substituted by one or more $C_{1-6}$alkyl groups, —$CONR^9R^{10}$, —$NHCOR^{10}$, —$SO_2NHR^9$, —$(CH_2)_qNHSO_2R^{10}$, halogen, CN, OH, —$(CH_2)_qNR^{11}R^{12}$ or trifluoromethyl;

$R^6$ is selected from $C_{1-6}$alkyl, $C_{1-6}$alkoxy, halogen, trifluoromethyl or —$(CH_2)_qNR^{11}R^{12}$;

$R^7$ is selected from hydrogen, $C_{1-6}$alkyl, —$(CH_2)_p$—$C_{3-7}$ cycloalkyl optionally substituted by one or more $C_{1-6}$alkyl groups, trifluoromethyl, —$(CH_2)_r$heteroaryl optionally substituted by $R^{13}$ and/or $R^{14}$ or —$(CH_2)_r$phenyl optionally substituted by $R^{13}$ and/or $R^{14}$;

$R^8$ is selected from hydrogen, $C_{1-6}$alkyl, $C_{3-7}$cycloalkyl optionally substituted by one or more $C_{1-6}$alkyl groups, $CONHR^9$, phenyl optionally substituted by $R^{13}$ and/or $R^{14}$ or heteroaryl optionally substituted by $R^{13}$ and/or $R^{14}$;

$R^9$ and $R^{10}$ are each independently selected from hydrogen or $C_{1-6}$alkyl, or $R^9$ and $R^{10}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two $C_{1-6}$alkyl groups;

$R^{11}$ is selected from hydrogen, $C_{1-6}$alkyl or —$(CH_2)_p$—$C_{3-7}$cycloalkyl optionally substituted by one or more $C_{1-6}$alkyl groups, $R^{12}$ is selected from hydrogen or $C_{1-6}$alkyl, or $R^{11}$ and $R^{12}$, together with the nitrogen atom to which they are bound, form a five or six-membered heterocyclic ring optionally containing one additional heteroatom selected from oxygen, sulfur and N—$R^{15}$;

$R^{13}$ is selected from $C_{1-6}$alkyl, $C_{1-6}$alkoxy, —$(CH_2)_p$—$C_{3-7}$ cycloalkyl optionally substituted by one or more $C_{1-6}$alkyl groups, —$CONR^9R^{10}$, —$NHCOR^{10}$, halogen, CN, —$(CH_2)_qNR^{11}R^{12}$, trifluoromethyl, phenyl optionally substituted by one or more groups or heteroaryl optionally substituted by one or more groups;

$R^{14}$ is selected from $C_{1-6}$alkyl, $C_{1-6}$alkoxy, halogen, trifluoromethyl or —$NR^{11}R^{12}$;

$R^{15}$ is selected from hydrogen or methyl;

X and Y are each independently selected from hydrogen, methyl or halogen;

Z is selected from —$(CH_2)_sOR^{16}$, —$(CH_2)_sNR^{16}R^{17}$, —$(CH_2)_sCH_2CH_2R^{16}$, —$(CH_2)_sCOOR^{16}$, —$(CH_2)_sCONR^{16}R^{17}$, —$(CH_2)_sNHCOR^{16}$, —$(CH_2)_sNHCONR^{16}R^{17}$, —$(CH_2)_sSO_2R^{16}$, —$(CH_2)_sSO_2NR^{16}R^{17}$ or —$(CH_2)_sNHSO_2R^{16}$;

$R^{16}$ is selected from hydrogen, $C_{1-6}$alkyl, —$(CH_2)_tOR^{18}$, —$(CH_2)_tNR^{18}R^{19}$, —$(CH_2)_tCOOR^{18}$, —$(CH_2)_t$heteroaryl optionally substituted by up to two groups independently selected from halogen or $C_{1-6}$alkyl, or is a —$(CH_2)_t$phenyl optionally substituted by up to two groups independently selected from halogen, $C_{1-6}$alkyl or $C_{1-6}$alkoxy, $R^{17}$ is selected from hydrogen or $C_{1-6}$alkyl, or $R^{16}$ and $R^{17}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two groups independently selected from oxo, halogen and $C_{1-6}$alkyl;

$R^{18}$ and $R^{19}$ are each independently selected from hydrogen or $C_{1-6}$alkyl, or $R^{18}$ and $R^{19}$, together with the nitrogen atom to which they are bound, form a five- to six-membered heterocyclic ring optionally containing one additional heteroatom selected from oxygen, sulfur and N—$R^{15}$, wherein the ring is optionally substituted by up to two groups independently selected from oxo, halogen or $C_{1-6}$alkyl;

m is selected from 0, 1, 2, 3 or 4, wherein each carbon atom of the resulting carbon chain may be optionally substituted with up to two groups independently selected from $C_{1-6}$alkyl or halogen;

n is 1;

p is selected from 0, 1 or 2;

q is selected from 0, 1, 2 or 3;

r is selected from 0 or 1;

s is selected from 0, 1, 2, 3 or 4; and t is selected from 2, 3 or 4;

or a pharmaceutically acceptable salt thereof.

14. A pharmaceutical composition comprising a compound according to claim 13, or a pharmaceutically salt thereof, in association with one or more pharmaceutically acceptable excipients, diluents and/or carriers.

15. The compound according to claim 1 which is:

$N^3$-Cyclopropyl-$N_4'$-(2,2-dimethylpropyl)-5-fluoro-2'-(hydroxymethyl)-6-methyl-3,4'-biphenyldicarboxamide, or a pharmaceutically acceptable salt thereof.

* * * * *